United States Patent
Price et al.

(10) Patent No.: US 9,449,785 B2
(45) Date of Patent: Sep. 20, 2016

(54) WORKPIECE TRANSPORT AND POSITIONING APPARATUS

(71) Applicant: Howard Hughes Medical Institute, Ashburn, VA (US)

(72) Inventors: John H. Price, Hingham, MA (US); Dravida Bock, Ashburn, VA (US)

(73) Assignee: Howard Hughes Medical Institute, Ashburn, VA (US)

( * ) Notice: Subject to any disclaimer, the term of this patent is extended or adjusted under 35 U.S.C. 154(b) by 0 days.

(21) Appl. No.: 14/538,391

(22) Filed: Nov. 11, 2014

(65) Prior Publication Data

US 2015/0243473 A1 Aug. 27, 2015

Related U.S. Application Data

(60) Provisional application No. 61/902,470, filed on Nov. 11, 2013.

(51) Int. Cl.

| | |
|---|---|
| *H01J 37/00* | (2006.01) |
| *H01J 37/20* | (2006.01) |
| *H01J 37/26* | (2006.01) |
| *H01J 37/02* | (2006.01) |

(Continued)

(52) U.S. Cl.
CPC ......... *H01J 37/20* (2013.01); *G01N 35/00732* (2013.01); *H01J 37/023* (2013.01); *H01J 37/185* (2013.01); *H01J 37/261* (2013.01); *G01N 1/32* (2013.01); *H01J 2237/201* (2013.01); *H01J 2237/204* (2013.01); *H01J 2237/2007* (2013.01); *H01J 2237/20278* (2013.01); *H01J 2237/2602* (2013.01)

(58) Field of Classification Search
USPC .................................................. 250/442.11
See application file for complete search history.

(56) References Cited

U.S. PATENT DOCUMENTS

| 4,183,614 A | 1/1980 | Feldman |
|---|---|---|
| 4,672,797 A | 6/1987 | Hagler |

(Continued)

FOREIGN PATENT DOCUMENTS

| WO | 9117941 | 11/1991 |
|---|---|---|
| WO | 2008049133 | 4/2008 |
| WO | 2014003557 | 1/2014 |

OTHER PUBLICATIONS

International Search Report, International Application No. PCT/US2014/065030, dated Apr. 1, 2015.

*Primary Examiner* — Phillip A Johnston
(74) *Attorney, Agent, or Firm* — Perman & Green, LLP

(57) ABSTRACT

An automated workpiece processing apparatus including a processing section including a processing module configured for processing a workpiece at a process location, a transport module including a first shuttle stage, a second shuttle stage independent of the first stage, and an end effector connected to at least one of the first and second stages, the end effector being configured to hold and transport the workpiece into and out of the processing module, and having a range of motion, defined by a combination of the first and second stage, extending from a workpiece holding station outside the processing module to the processing location inside the processing module so the end effector defines a processing stage of the processing module, and an automated loading and transport section including a load port module through which workpieces are loaded into the automated loading and transport section, and being communicably connected to the transport module.

20 Claims, 41 Drawing Sheets

(51) Int. Cl.
*H01J 37/18* (2006.01)
*G01N 35/00* (2006.01)
*G01N 1/32* (2006.01)

(56) References Cited

U.S. PATENT DOCUMENTS

| | | | |
|---|---|---|---|
| 4,917,556 A | 4/1990 | Stark et al. | |
| 5,246,524 A | 9/1993 | Kuroda et al. | |
| 5,326,971 A | 7/1994 | Theodore et al. | |
| 5,726,433 A | 3/1998 | Peng | |
| 5,753,924 A | 5/1998 | Swann | |
| 5,821,544 A | 10/1998 | Augustus et al. | |
| 6,002,136 A | 12/1999 | Naeem | |
| 6,068,437 A | 5/2000 | Boje et al. | |
| 6,242,737 B1 | 6/2001 | Ohnishi et al. | |
| 6,258,326 B1 | 7/2001 | Modlin | |
| 6,281,510 B1 | 8/2001 | Yoshitake et al. | |
| 6,495,838 B1 | 12/2002 | Yaguchi et al. | |
| 6,597,500 B1 | 7/2003 | Burke et al. | |
| 6,872,955 B1 | 3/2005 | Balcome et al. | |
| 6,891,170 B1 * | 5/2005 | Yu | H01J 37/20 250/442.11 |
| 6,902,703 B2 | 6/2005 | Marquiss et al. | |
| 6,927,400 B2 | 8/2005 | Rasmussen | |
| 6,946,654 B2 | 9/2005 | Gerlach et al. | |
| 6,963,068 B2 | 11/2005 | Asselbergs et al. | |
| 6,967,335 B1 * | 11/2005 | Dyer | G02B 21/32 250/442.11 |
| 6,995,380 B2 | 2/2006 | Rasmussen | |
| 7,034,316 B2 | 4/2006 | Wagner et al. | |
| 7,071,475 B2 | 7/2006 | Tomimatsu et al. | |
| 7,115,882 B2 | 10/2006 | Moore | |
| 7,126,133 B2 | 10/2006 | Moore | |
| 7,230,253 B2 | 6/2007 | Ham | |
| 7,253,408 B2 | 8/2007 | West | |
| 7,375,325 B2 | 5/2008 | Burkhardt et al. | |
| 7,381,968 B2 | 6/2008 | Tanaka et al. | |
| 7,390,458 B2 | 6/2008 | Burow et al. | |
| 7,474,419 B2 | 1/2009 | Tappel et al. | |
| 7,476,787 B2 | 1/2009 | Thomas et al. | |
| 7,511,282 B2 | 3/2009 | Agorio et al. | |
| 7,625,679 B2 | 12/2009 | Sullivan et al. | |
| 7,644,637 B2 | 1/2010 | Moore et al. | |
| 7,663,101 B2 | 2/2010 | Goodman | |
| 7,675,049 B2 | 3/2010 | Schmidt et al. | |
| 7,677,289 B2 | 3/2010 | Hayworth et al. | |
| 7,745,785 B2 | 6/2010 | Nishiyama | |
| 7,745,802 B2 | 6/2010 | Nishiyama et al. | |
| 7,851,769 B2 | 12/2010 | Schmid et al. | |
| 7,888,655 B2 | 2/2011 | van Gaasbeek et al. | |
| 7,906,762 B2 | 3/2011 | Bierhoff et al. | |
| 7,923,700 B2 | 4/2011 | Nishiyama | |
| 7,928,380 B2 | 4/2011 | Suga et al. | |
| 7,935,937 B2 | 5/2011 | Moore et al. | |
| 7,939,906 B2 | 5/2011 | Luo et al. | |
| 7,989,778 B2 | 8/2011 | Oetelaar et al. | |
| 8,011,259 B2 | 9/2011 | Dona | |
| 8,030,622 B2 | 10/2011 | Nishiyama et al. | |
| 8,058,627 B2 | 11/2011 | Zach | |
| 8,102,523 B1 | 1/2012 | Marsh et al. | |
| 8,139,213 B2 | 3/2012 | Bahatt et al. | |
| 8,143,593 B2 | 3/2012 | Milas et al. | |
| 8,148,685 B2 | 4/2012 | Qian et al. | |
| 8,164,057 B2 | 4/2012 | Shacal | |
| 8,207,431 B2 | 6/2012 | Feng et al. | |
| 8,222,618 B2 | 7/2012 | Tokuda et al. | |
| 8,227,781 B2 | 7/2012 | Zaykova-Feldman et al. | |
| 8,258,473 B2 | 9/2012 | Shaapur et al. | |
| 8,288,723 B2 | 10/2012 | Zhang et al. | |
| 8,294,098 B2 | 10/2012 | Zhang et al. | |
| 8,309,921 B2 | 11/2012 | Bierhoff et al. | |
| 8,334,510 B2 | 12/2012 | Shachal et al. | |
| 8,336,405 B2 | 12/2012 | Stabacinskiene et al. | |
| 8,346,574 B2 | 1/2013 | Chirica et al. | |
| 8,387,227 B2 | 3/2013 | Liu et al. | |
| 8,395,130 B2 | 3/2013 | Gatcher | |
| 8,410,457 B2 | 4/2013 | Terada et al. | |
| 8,436,303 B2 | 5/2013 | Zhang et al. | |
| 8,439,216 B1 | 5/2013 | Walck | |
| 8,455,821 B2 | 6/2013 | Arjavac et al. | |
| 8,455,842 B2 | 6/2013 | Zhang et al. | |
| 8,497,487 B2 | 7/2013 | Milas et al. | |
| 8,507,876 B2 | 8/2013 | Goodman et al. | |
| 8,524,139 B2 | 9/2013 | Toth et al. | |
| 8,524,450 B2 | 9/2013 | Moon et al. | |
| 8,569,719 B2 | 10/2013 | Tomimatsu et al. | |
| 8,581,205 B2 | 11/2013 | Wei et al. | |
| 8,598,485 B2 | 12/2013 | Adachi | |
| 8,618,520 B2 | 12/2013 | Tokuda et al. | |
| 8,623,227 B2 | 1/2014 | Lin et al. | |
| 8,629,416 B2 | 1/2014 | Straw et al. | |
| 8,639,463 B2 | 1/2014 | Kimba et al. | |
| 8,650,739 B2 | 2/2014 | Qian et al. | |
| 8,653,476 B2 | 2/2014 | Miyazaki | |
| 8,662,392 B2 | 3/2014 | Hagen et al. | |
| 8,676,509 B2 | 3/2014 | De La Torre-Bueno | |
| 8,704,175 B2 | 4/2014 | Sohda et al. | |
| 8,716,676 B2 | 5/2014 | Safar | |
| 8,742,344 B2 | 6/2014 | Hatakeyama et al. | |
| 8,754,384 B1 | 6/2014 | Persoon et al. | |
| 8,822,951 B2 * | 9/2014 | Sun | H01J 37/20 250/307 |
| 2001/0002986 A1 | 6/2001 | Fattinger et al. | |
| 2002/0028399 A1 | 3/2002 | Nakasuji et al. | |
| 2004/0237670 A1 | 12/2004 | Koo et al. | |
| 2004/0256570 A1 | 12/2004 | Wagner et al. | |
| 2005/0107917 A1 | 5/2005 | Smith et al. | |
| 2005/0200841 A1 * | 9/2005 | Talbot | G06T 7/0004 356/237.4 |
| 2007/0029503 A1 | 2/2007 | Jung | |
| 2007/0029504 A1 * | 2/2007 | Saito | H01J 37/18 250/441.11 |
| 2008/0068706 A1 | 3/2008 | Goodman | |
| 2008/0250881 A1 | 10/2008 | Dona | |
| 2010/0025580 A1 | 2/2010 | Hammer et al. | |
| 2010/0230584 A1 | 9/2010 | Niebel et al. | |
| 2010/0230590 A1 | 9/2010 | Bierhoff et al. | |
| 2011/0017922 A1 | 1/2011 | Amador | |
| 2011/0253905 A1 | 10/2011 | Moebus et al. | |
| 2011/0253908 A1 | 10/2011 | Feng et al. | |
| 2012/0006711 A1 | 1/2012 | Goodman et al. | |
| 2013/0099134 A1 | 4/2013 | Sun et al. | |
| 2013/0323829 A1 | 12/2013 | Torterella | |
| 2013/0328246 A1 | 12/2013 | Wells et al. | |
| 2014/0014835 A1 | 1/2014 | Hosoya et al. | |
| 2014/0042338 A1 | 2/2014 | Shibata et al. | |
| 2014/0233691 A1 | 8/2014 | Sheppard et al. | |

* cited by examiner

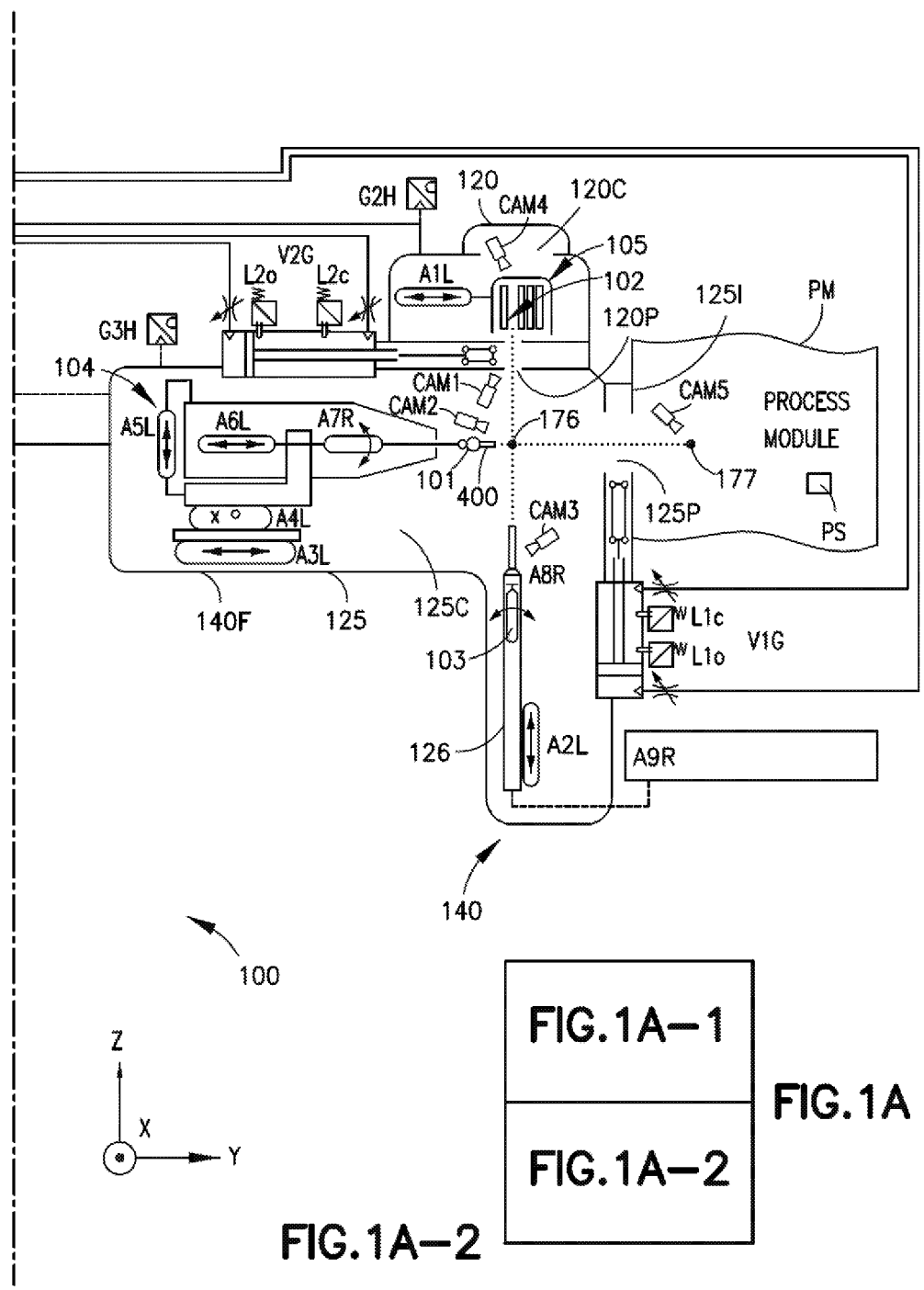

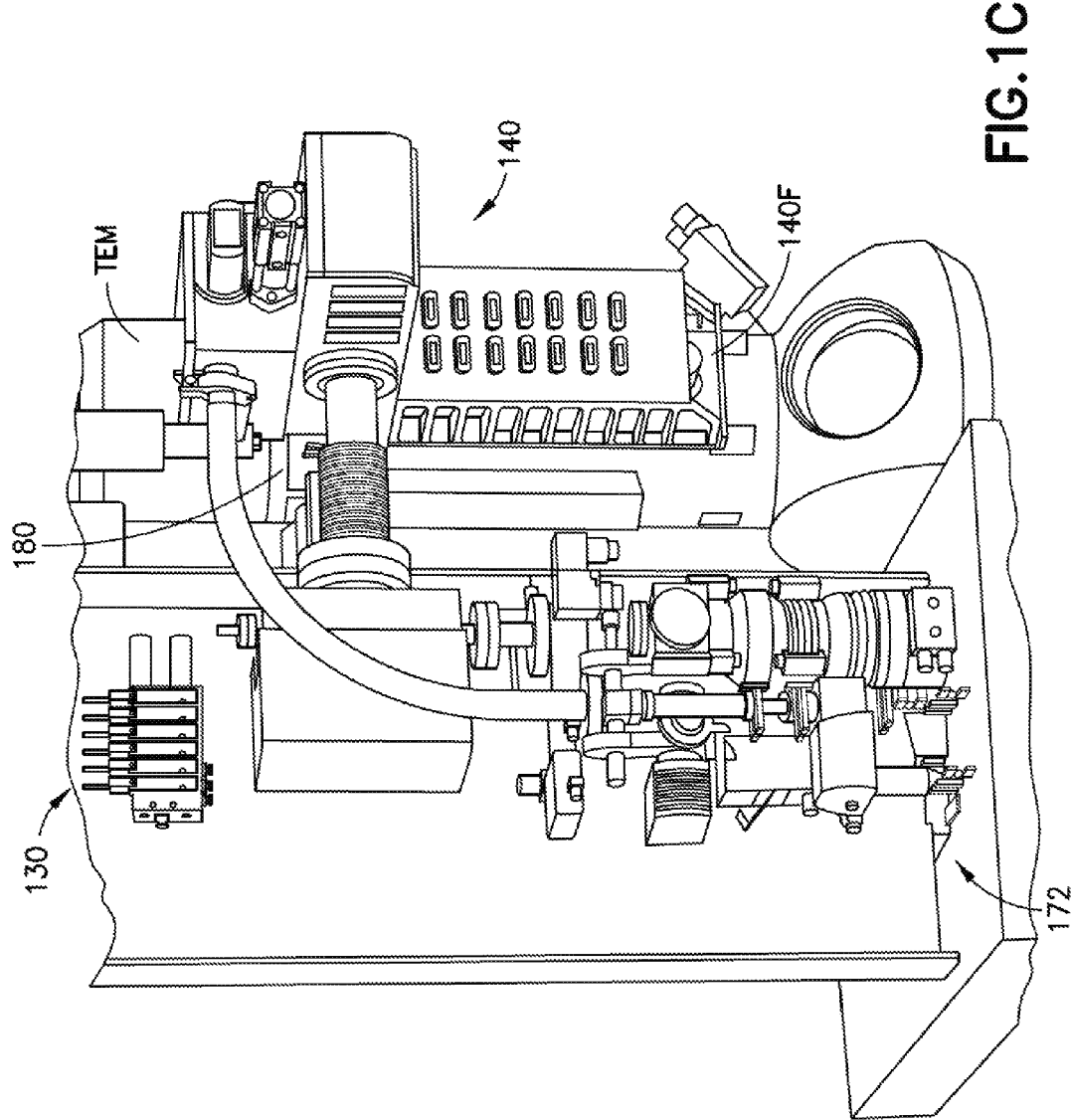

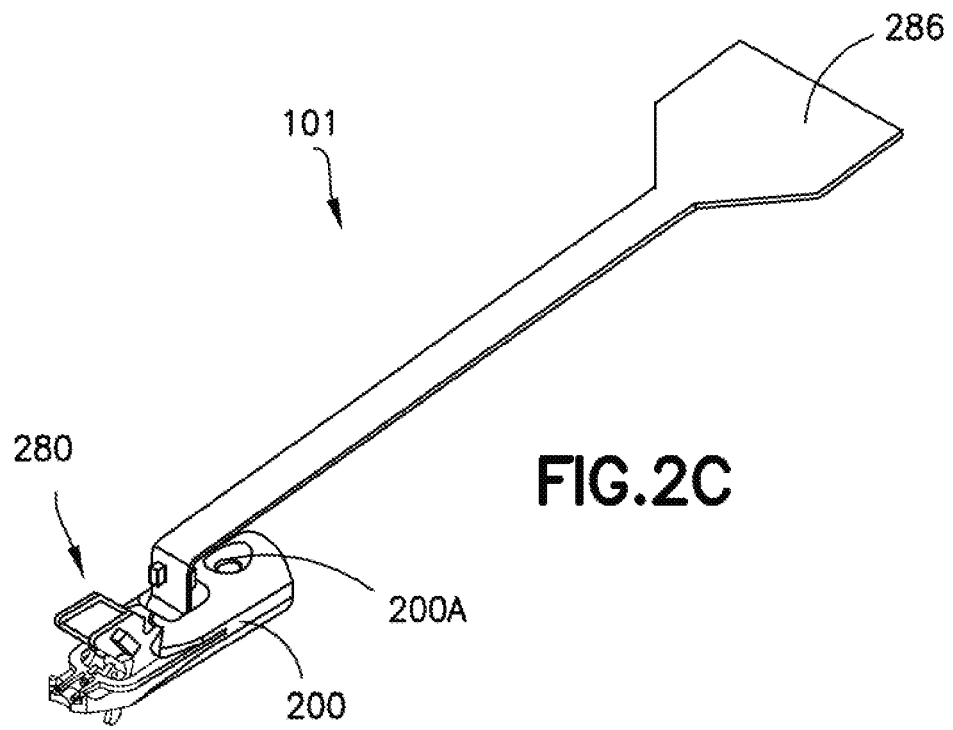
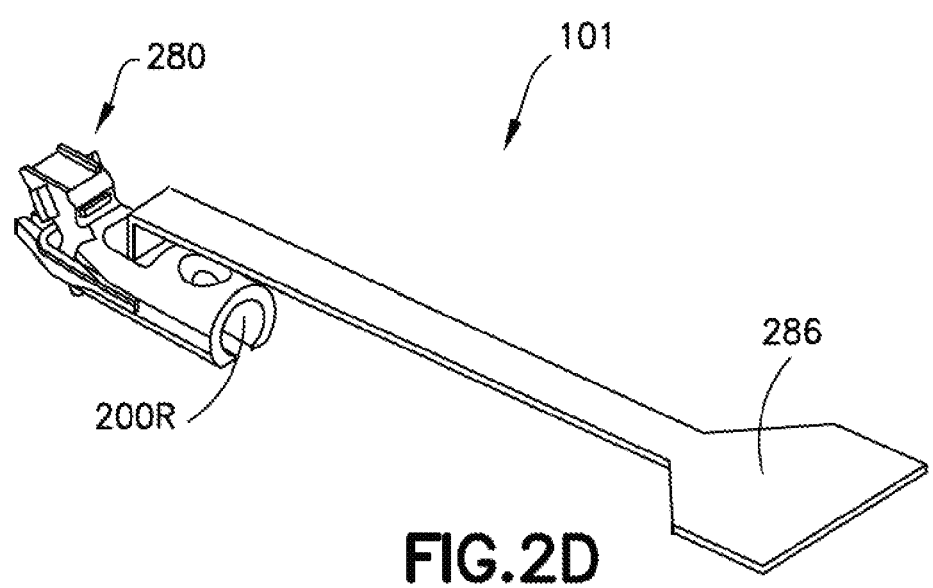

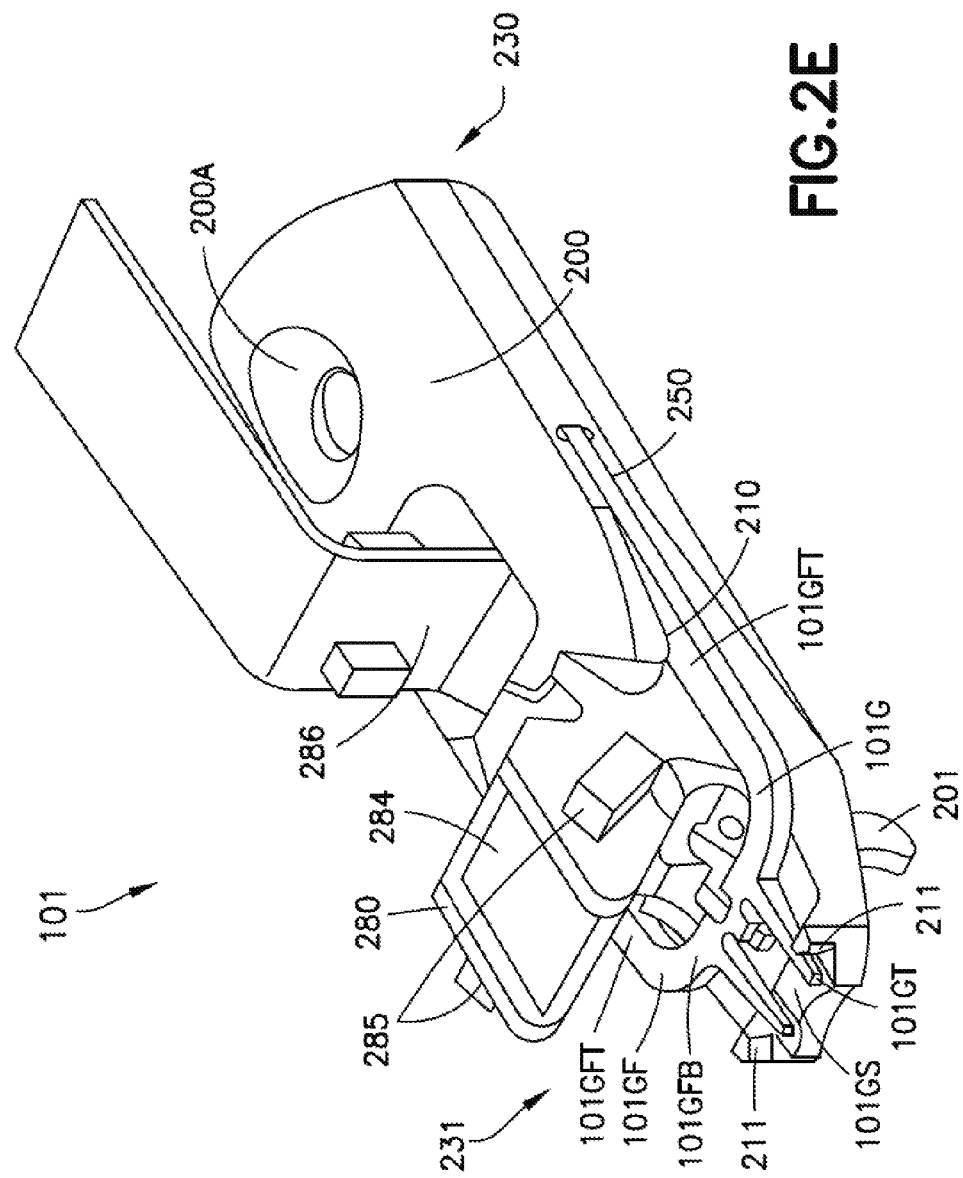

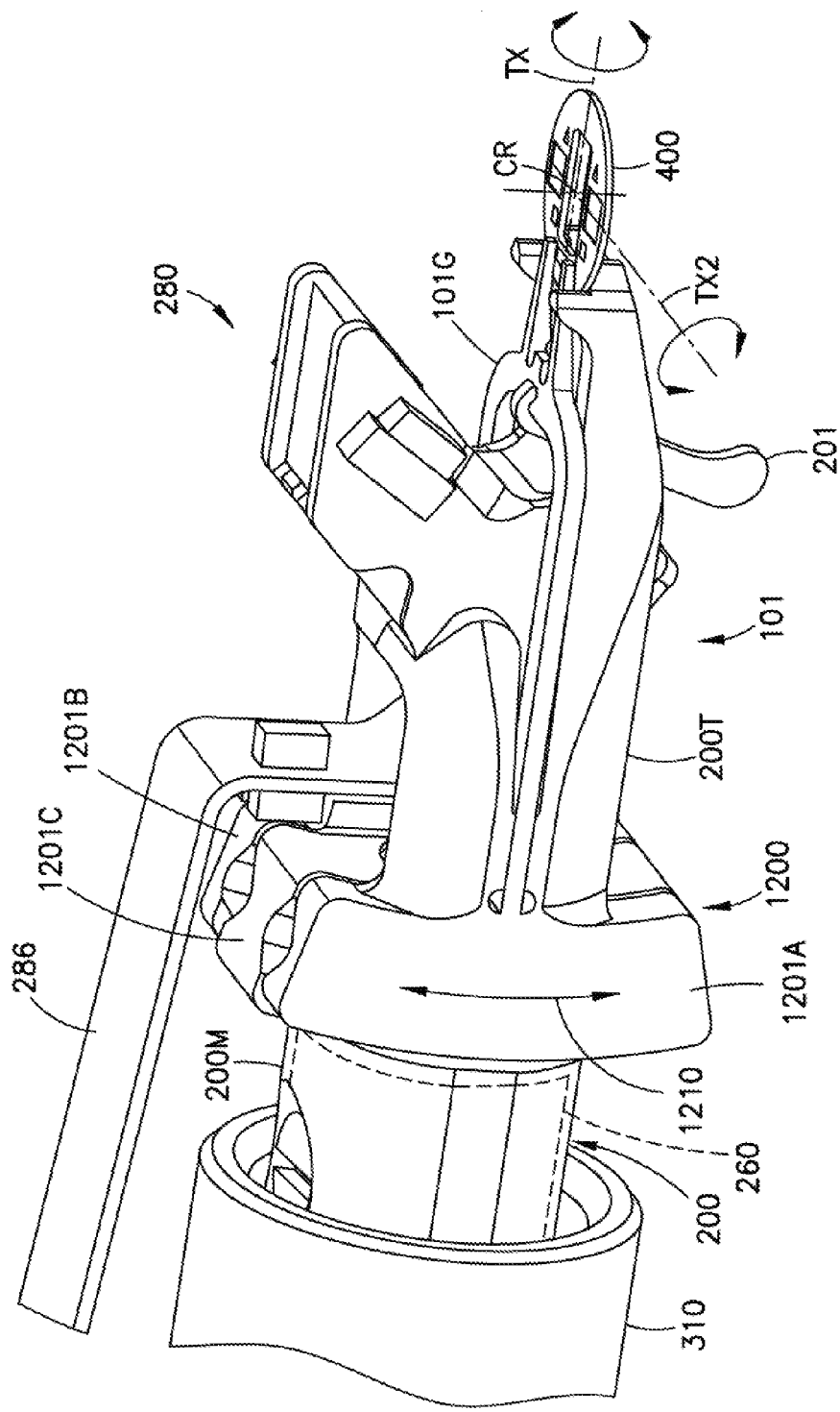

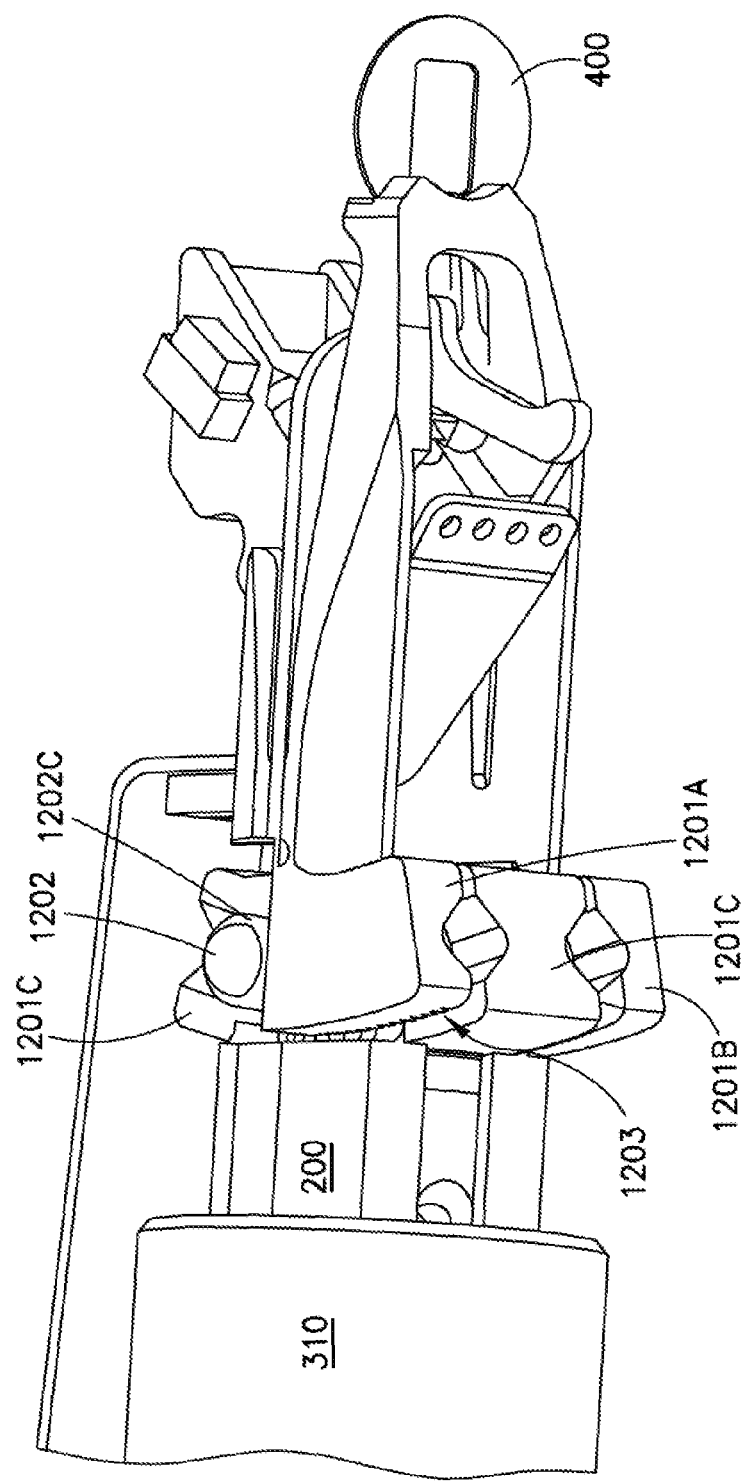

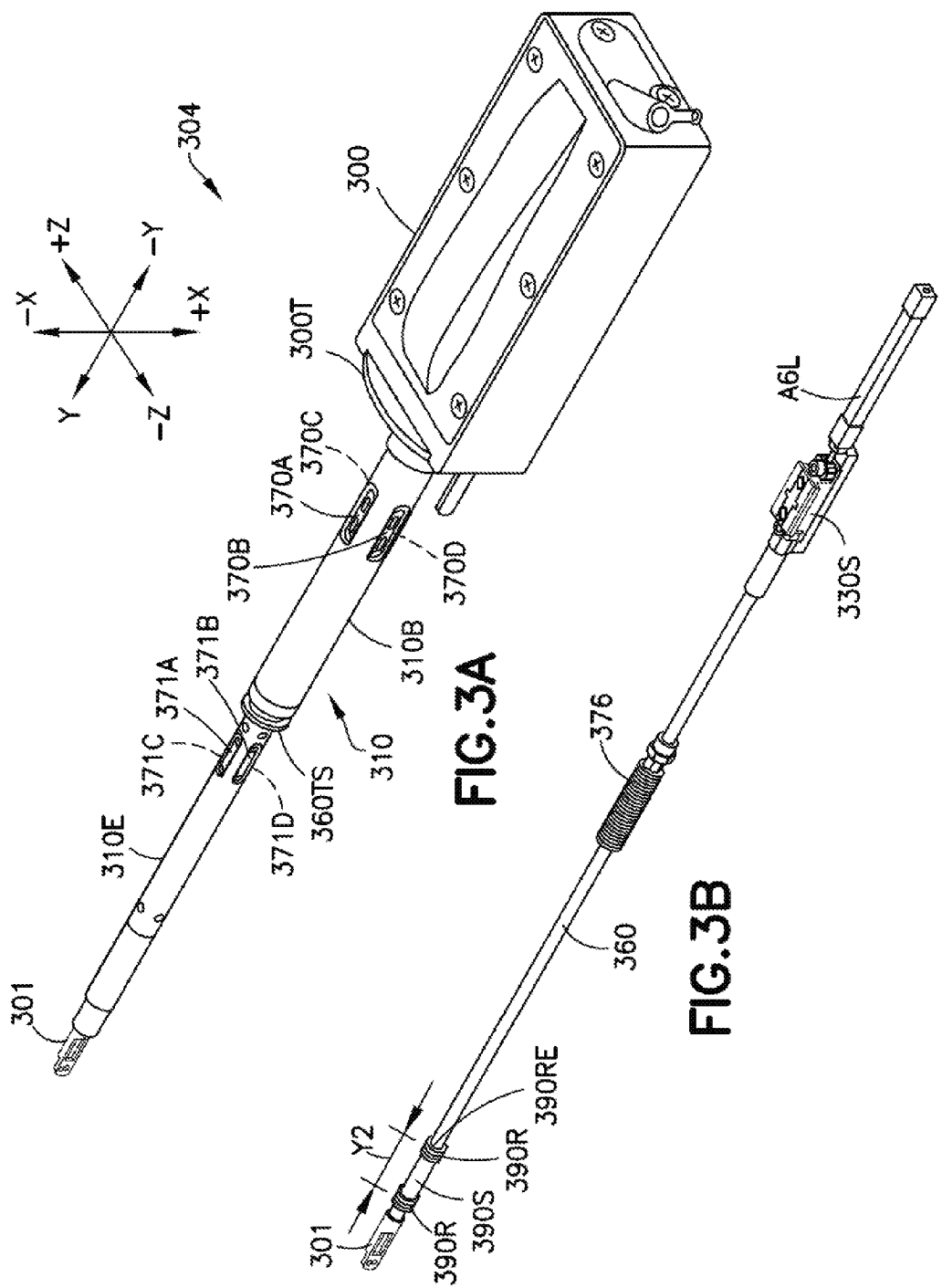

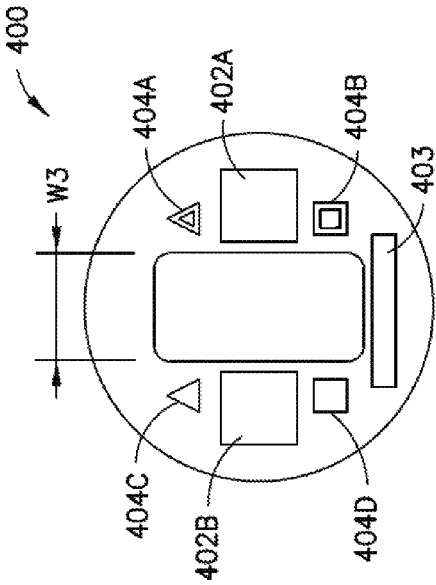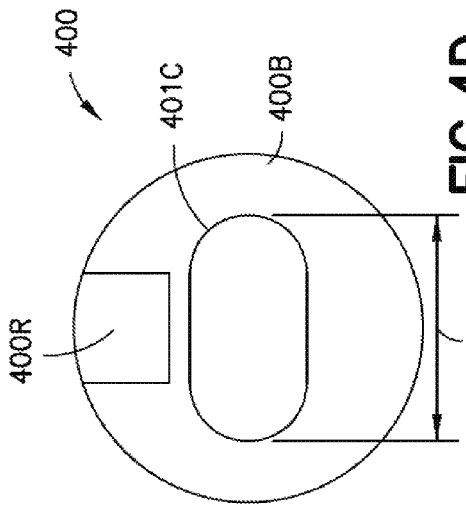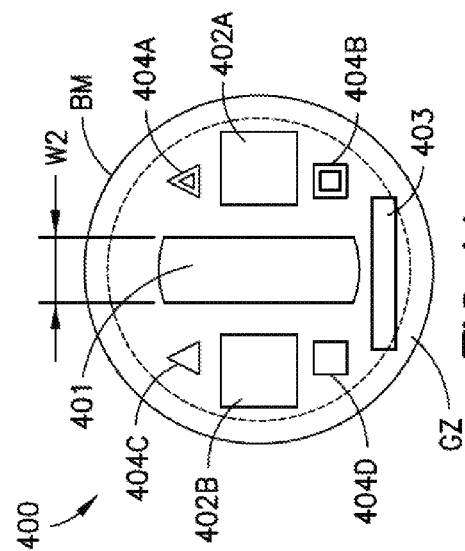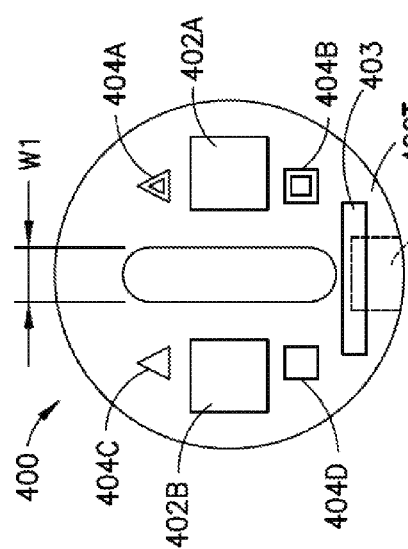

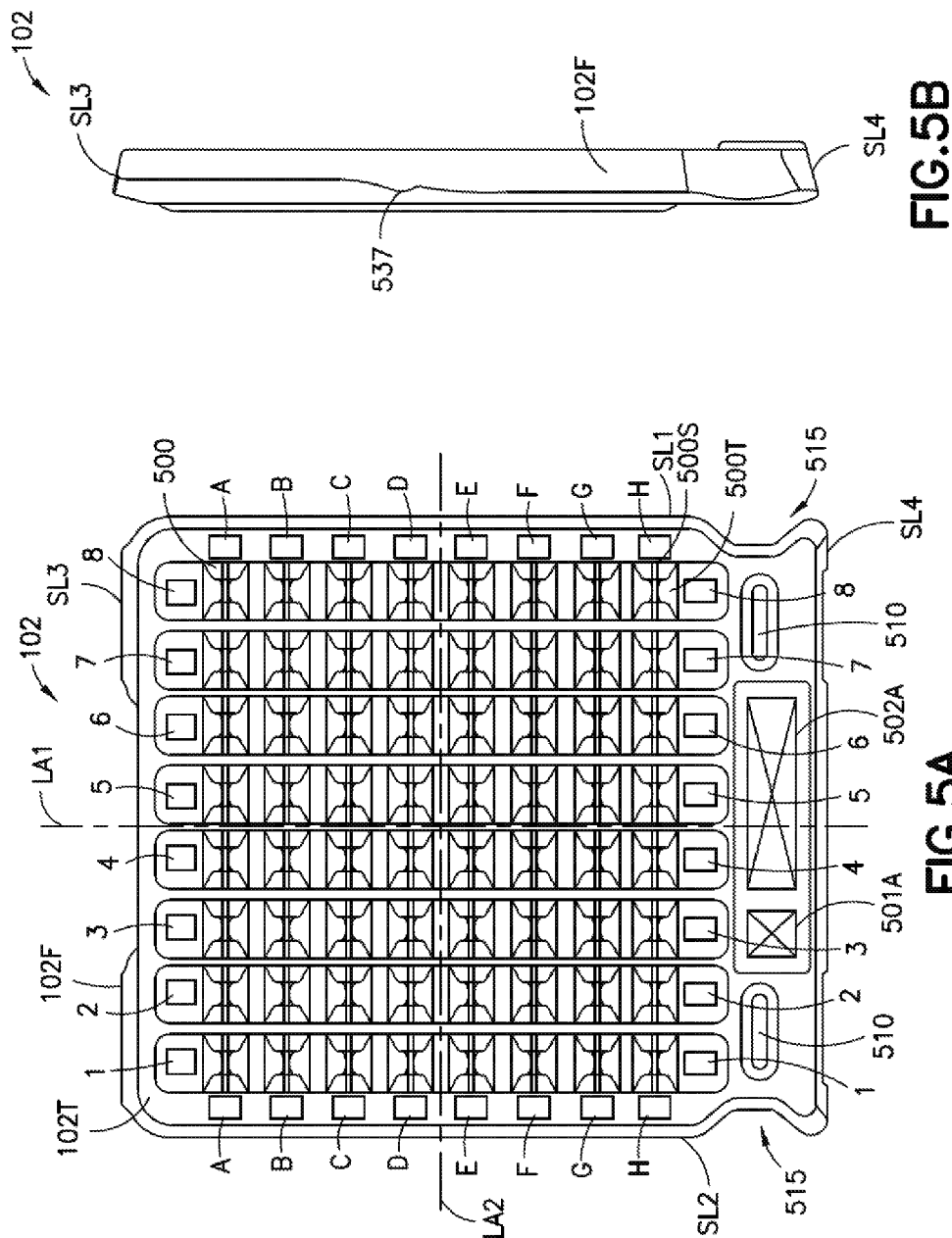

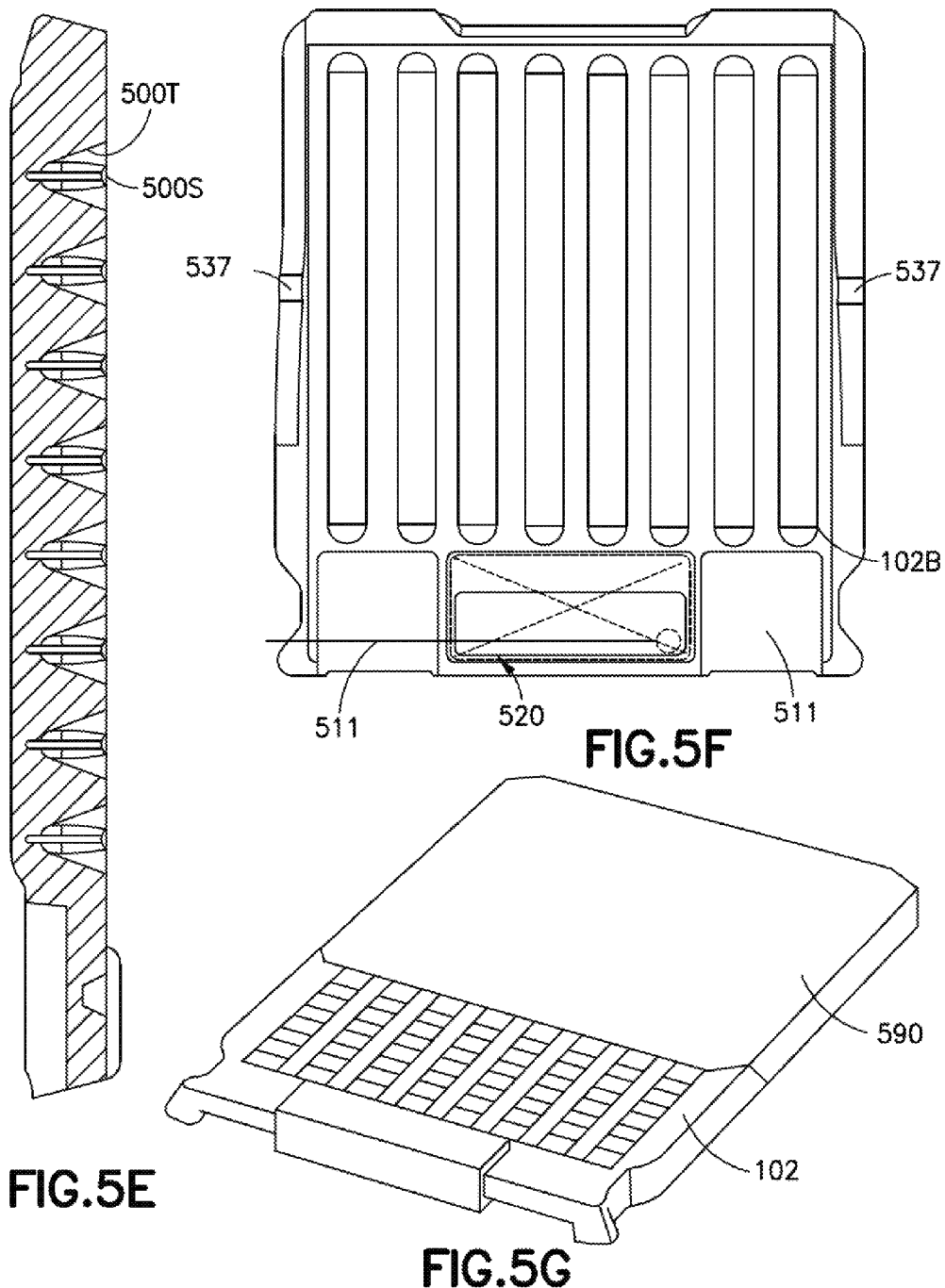

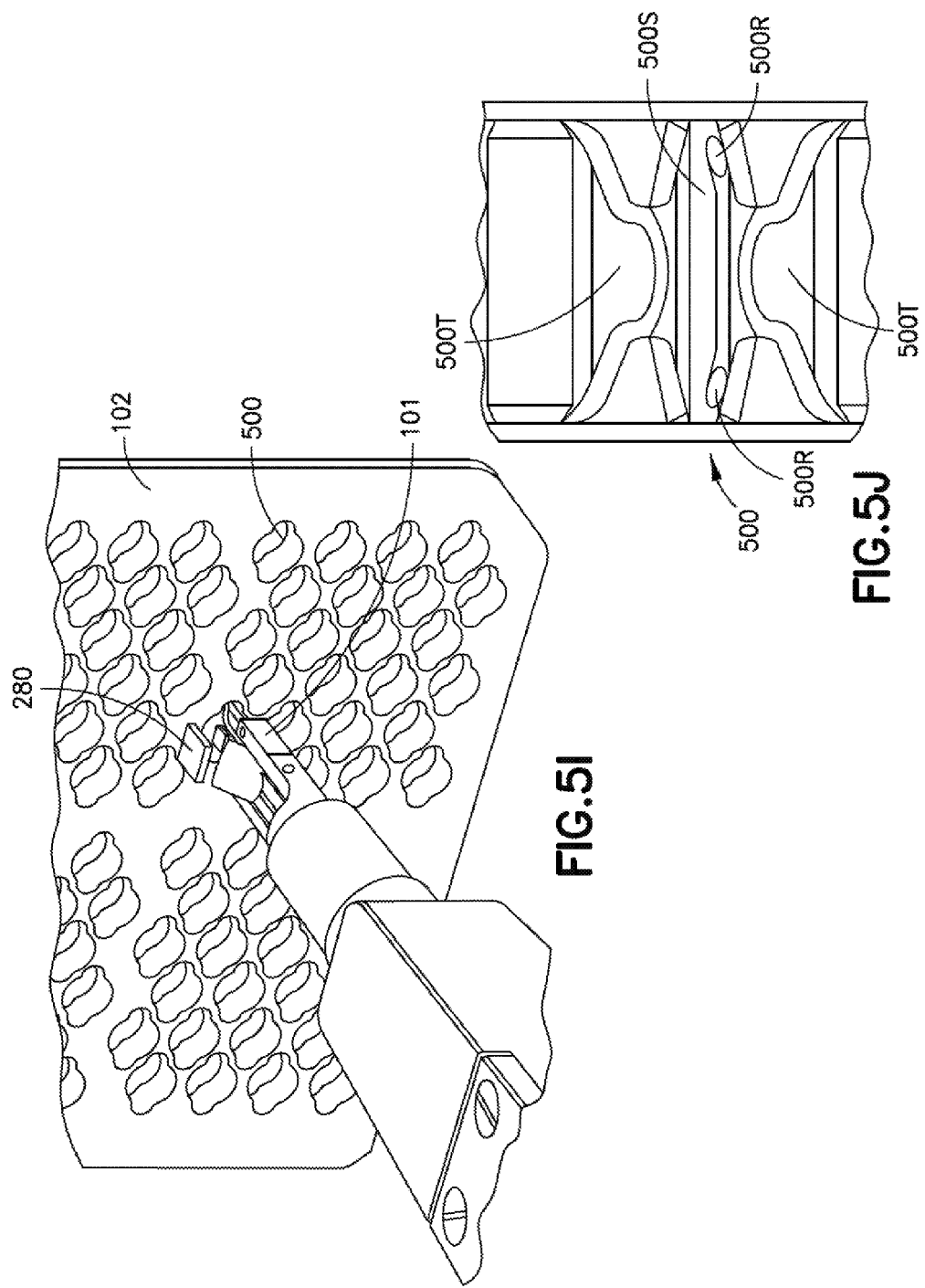

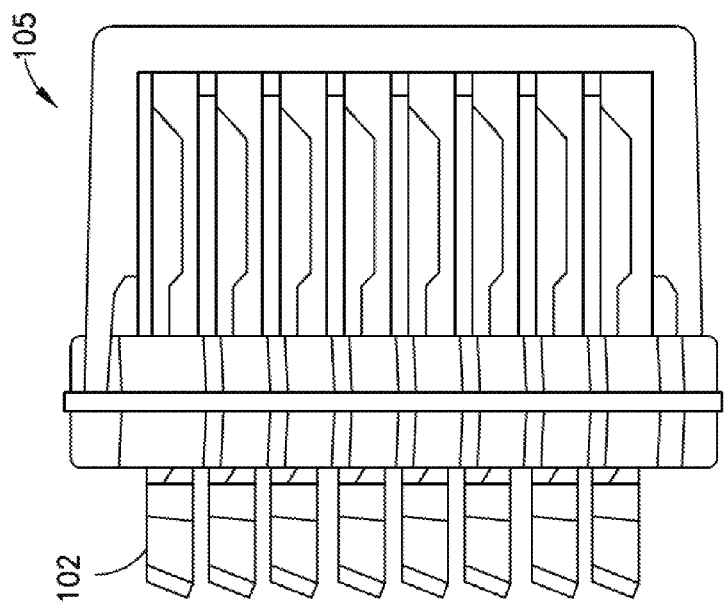
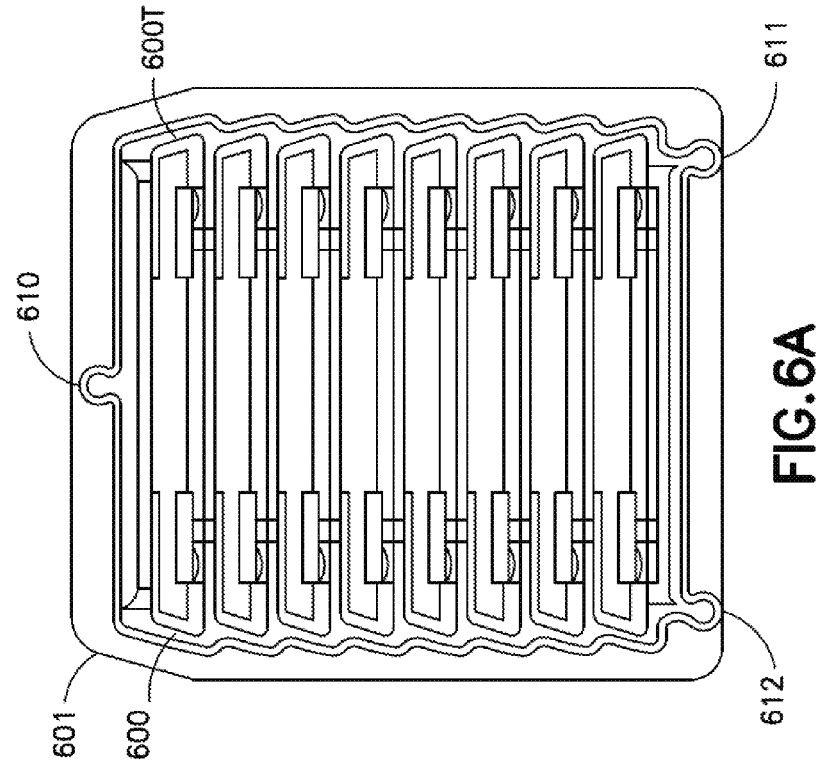
FIG. 6A
FIG. 6B

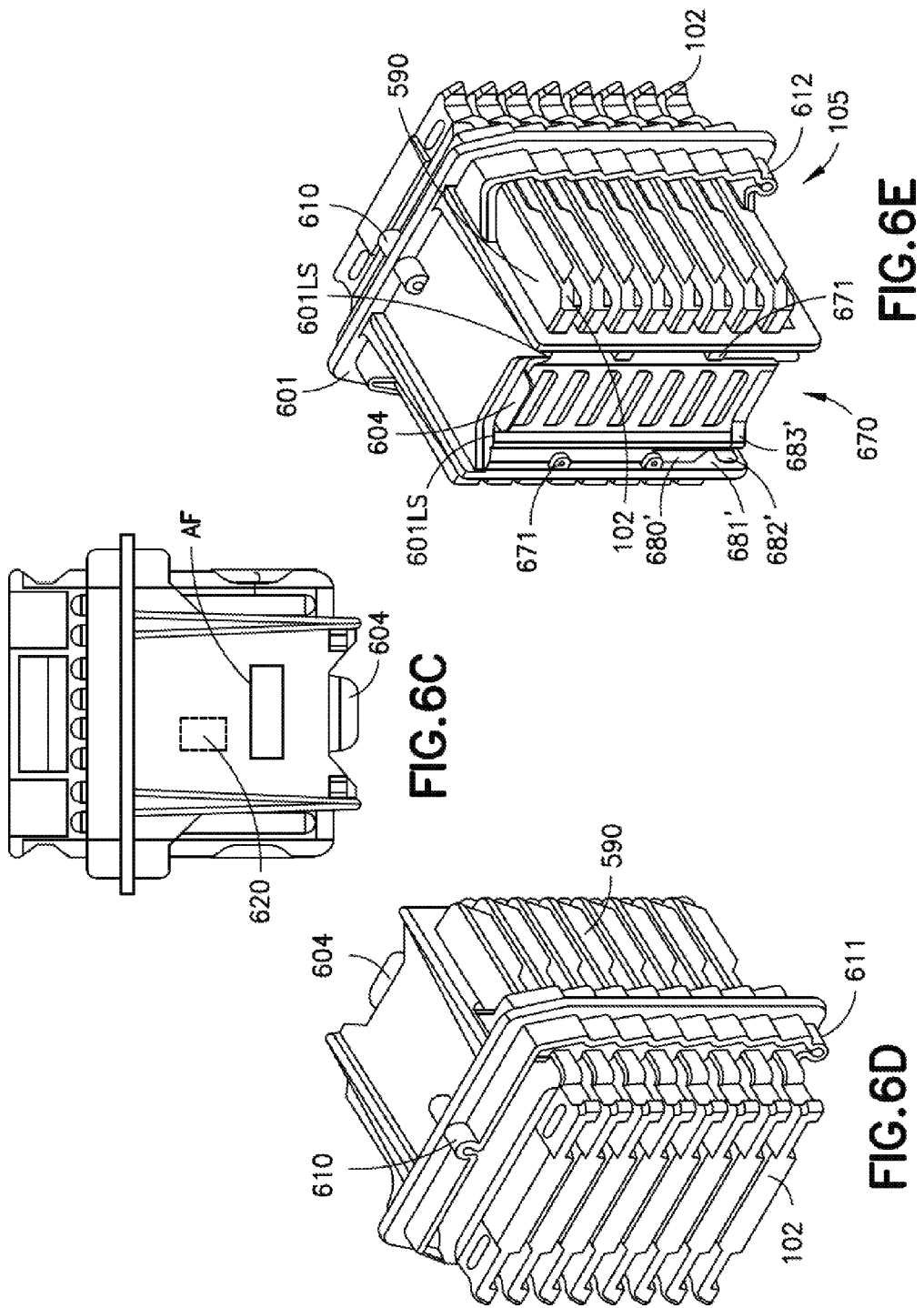

WORKPIECE TRANSPORT AND POSITIONING APPARATUS

CROSS REFERENCE TO RELATED APPLICATIONS

This application is a non-provisional of and claims the benefit of U.S. provisional patent application No. 61/902,470 filed on Nov. 11, 2013 the disclosure of which is incorporated herein by reference in its entirety.

BACKGROUND

1. Field

The exemplary embodiments generally relate to automated workpiece processing systems and, more particularly, to automatic loading systems for automated processing systems.

2. Brief Description of Related Developments

Generally automated workpiece processing systems include workpiece transports and processing modules. The workpiece transports are generally employed to transport workpieces to and from the processing modules where the workpieces are placed on a workpiece holder for processing. During processing of the workpiece transports are removed from the process module and the process module is generally sealed.

Some of the process module workpiece holders include movable stages configured to position the workpiece for processing. These movable stages, as well as the workpiece transports that deliver the workpieces to the process modules, generally require settling times between movements of the workpiece for allowing residual motion of the workpiece to diminish so that undesired vibrational modes of the workpiece are not present during processing.

It would be advantageous to have an automated transport and positioning system that that includes a workpiece transport that can deliver workpieces to a process module and position the workpiece within the processing module during processing of the workpiece.

BRIEF DESCRIPTION OF THE DRAWINGS

The foregoing aspects and other features of the disclosed embodiment are explained in the following description, taken in connection with the accompanying drawings, wherein:

FIGS. 1B-1D and 1H are schematic illustrations of portions of the automatic specimen loading system of FIG. 1A (1A-1,1A-2) in accordance with aspects of the disclosed embodiment;

FIGS. 2A-2L are schematic illustrations of portions of a specimen positioning system and portions thereof in accordance with aspects of the disclosed embodiment;

FIGS. 3A-3E are schematic illustrations of a specimen positioning system and portions thereof in accordance with aspects of the disclosed embodiment;

FIGS. 4A-4D are schematic illustrations of a workpiece in accordance with aspects of the disclosed embodiment;

FIGS. 5A-5G, 5I and 5J are schematic illustrations of a specimen cassette in accordance with aspects of the disclosed embodiment;

FIGS. 6A-6F are schematic illustrations of a cassette magazine in accordance with aspects of the disclosed embodiment;

DETAILED DESCRIPTION

Figures 1, 1A:
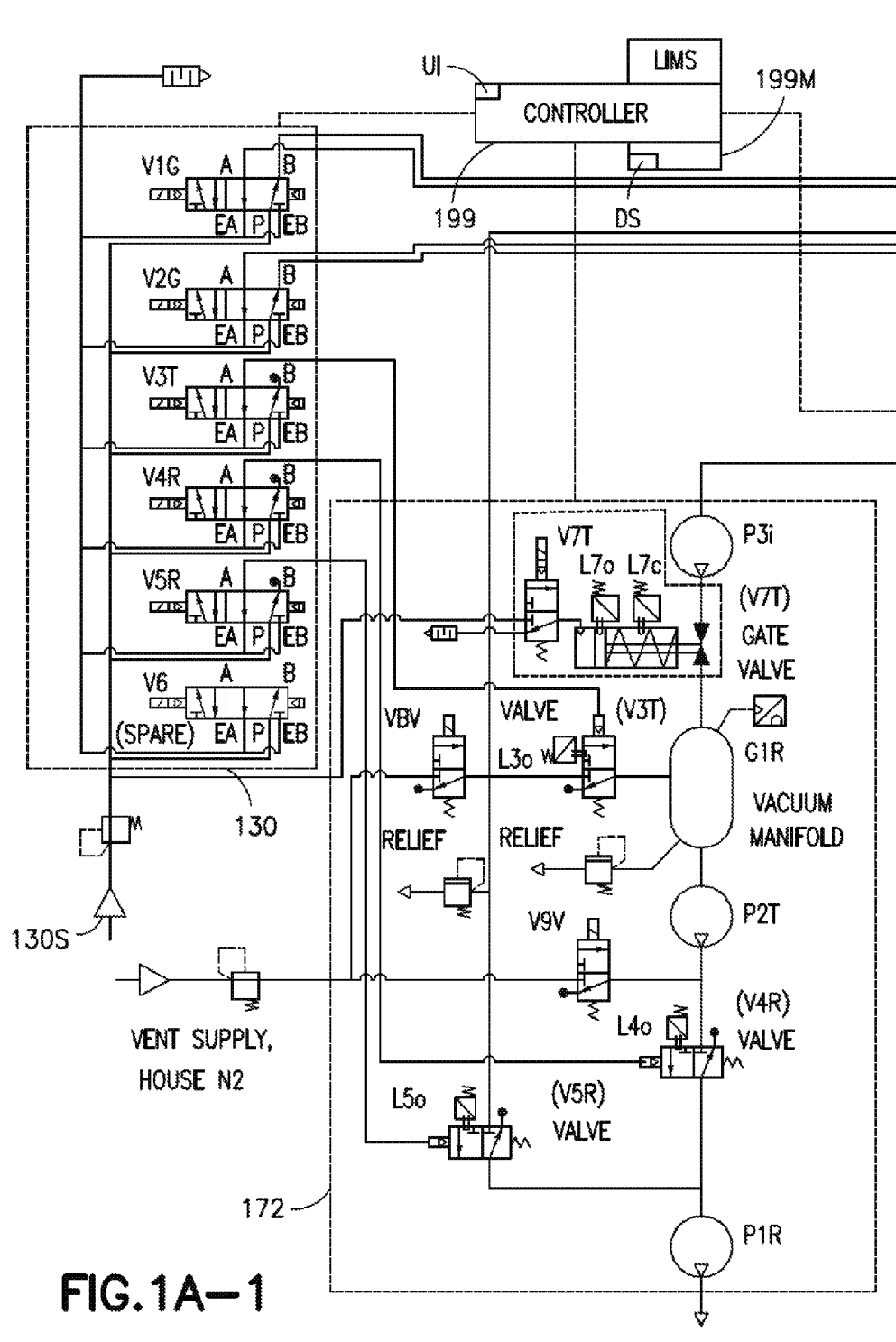
FIG. 1A (1A-1,1A-2) is a schematic illustration of an automatic specimen/sample loading system in accordance with aspects of the disclosed embodiment.

FIG. 1A (1A-1,1A-2) is a schematic illustration of an automated transport and positioning system 100 in accordance with aspects of the disclosed embodiment. Although the aspects of the disclosed embodiment will be described with reference to the drawings, it should be understood that the aspects of the disclosed embodiment can be embodied in many forms. In addition, any suitable size, shape or type of elements or materials could be used. It is also noted that while X, Y and Z axis are referred to, reference to these axes is exemplary only and in other aspects the axes have any suitable directional identifiers.

It should also be understood that while the aspects of the disclosed embodiments are described herein with respect to a transmission electron microscope (TEM), the aspects of the disclosed embodiment can be applied to scanning electron microscope (SEM), a dual beam focused ion beam microscope (DB-FIB), scanning transmission electron microscope (STEM), any other suitable electron beam scanning/imaging device or any suitable workpiece processing equipment having a process module PM where a workpiece is supported on a stage or workpiece holder of an end effector (as described herein) during processing of the workpiece. For example, aspects of the disclosed embodiment are employed in any suitable metrology equipment where a workpiece is held by the end effector of the disclosed embodiment during measurement/inspection or other processing. As will be described below, in one aspect, the stage is an end effector 101 of a workpiece positioning unit 104 of an automated transport and positioning system 100 while in other aspects the stage is an existing positioning stage PS of the process module PM.

In one aspect, in the context of the TEM, the automated transport and positioning system 100 provides loading and storage of about 500 to about 1000 specimens (also referred to herein as samples) in a single exchange (e.g. loading of specimens) while in other aspects related to the TEM or other suitable workpiece processing equipment (such as those mentioned above) more or less workpieces are loaded and stored. In one aspect, the automated transport and positioning system 100 replaces the conventional positioning "stage" PS used in, for example, TEMs that positions specimen holders or grids within the TEM during imaging. In other aspects the automated transport and positioning system 100 replaces any suitable loading system of, for example, any suitable metrology or other processing equipment. In one aspect, the automated transport and positioning system 100 also provides for complete, high-resolution, high-speed, high-stability position control of the workpiece during imaging or inspection. As will be described below, in accordance with the aspects of the disclosed embodiment, the grid handling and storage operations as well as the positioning of the specimen in the TEM column is effected with, in one aspect, eight controlled degrees of freedom and, in other aspects, with nine controlled degrees of freedom.

As will also be described below, the automated transport and positioning system 100 includes a transport and positioning unit 140 that has an end effector 101 configured to substantially directly handle any suitable workpiece 400 such as a grid (or other suitable specimen holder) with or without, for example, the use of a carrier or adapter that interfaces the workpiece with the handling system. In one aspect a gripper of the end effector 101 is operated through coordinated movement of, in one aspect, two or more of the eight controlled degrees of freedom and, in other aspects, nine controlled degrees of freedom, which when combined act to open and close the gripper while maintaining the end effector position constant relative to the workpiece as well as effect multiple independent degree of freedom motion of the end effector 101. In other aspects the gripper of the end effector is operated in any suitable manner such as with a dedicated drive that drives the gripper. In one aspect, the end effector 101 is configured to manipulate the workpiece in a high vacuum environment, such as within an objective lens chamber (described below) of an electron microscopy system, or any other suitable environment such as a non-vacuum or low vacuum environment. The end effector 101 is configured to grip individual workpieces during extraction from any suitable workpiece holding cassette 102 as well as be configured for the placement and removal of the workpieces to and from a pre-aligner stage 103 for rotational alignment of the workpiece. In one aspect the end effector 101 (and the workpiece positioning unit or multistage shuttle 104 which the end effector is a part of) is configured to provide a precision and rigid interface to support the grid mounted specimen which enables fast position moves (e.g. about 8 to about 24 microns or any other suitable distance) and rapid settling (e.g. to about less than 5 nanometers) in less than about 100 ms substantially without introducing undesired vibrational modes in the workpiece during imaging. In other aspects the end effector 101 (and the workpiece positioning unit 104 which the end effector is a part of) may be configured to perform fast position moves (e.g. about 8 to about 24 microns or any other suitable distance) and rapid settling (e.g. to about less than 4 nanometers) in less than about 25 ms to about 35 ms substantially without introducing undesired vibrational modes in the workpiece during imaging. It is noted that while the end effector 101 is shown has having a single workpiece holding gripper in other aspects the end effector is configured to hold multiple workpieces in, for example, a side by side arrangement or any other suitable arrangement. As will be described below, the automated transport and positioning system 100 includes a drive section having multiple degrees of freedom (in one aspect at least three degrees of freedom) for effecting any suitable processing of samples within the process module including but not limited to thin section tomography. In one aspect, as described herein, the multiple degrees of freedom of the drive section of the automated transport and positioning system 100 includes at least one linear axis traverse and rotation about at least 2 axes angled relative to each other. In one aspect the drive section of the automated transport and positioning system 100, as will also described herein, is configured to effect an automatic picking of the workpiece with the end effector 101. In one aspect, the drive section of the automated transport and positioning system 100 effects motion of the end effector with micron level resolution (e.g. in one aspect about 0.5 microns while in other aspects more or less than about 0.5 microns) and repositioning to different, for example, tomography inspection positions in less than about 100 ms.

As will be described below, in one aspect, handling (e.g. picking and placing) of the workpiece is performed utilizing a vision system that includes one or more cameras or optical detectors and/or an illumination unit integrated substantially directly into the end effector 101 and/or at other suitable locations off of the end effector where workpieces are imaged as described herein. The integral vision system provides substantially continuous monitoring of the workpiece handling operations and permits a closed loop control of each operation through any suitable image analysis algorithms that are stored in any suitable memory 199M of any suitable controller 199 connected to the automated transport and positioning system 100. It is noted that the controller 199 is suitably configured to control the automated transport and positioning system in the manner described herein. In one aspect the controller 199 is connected to, in any suitable manner, or integrated in a laboratory information management system LIMS for tracking the location of specimen samples within a laboratory or other facility as described herein. The vision system provides for workpiece fiducial (or other suitable features of the grid) detection to effect workpiece alignment during the workpiece handling operations. In other aspects the vision system provides for workpiece identification, tracking and/or effect controlled guided movement of the end effector. Suitable examples of workpiece tracking can be found in, for example, United States patent application Ser. No. 14/538,327 entitled "Workpiece Holder for Workpiece Transport Apparatus" filed on Nov. 11, 2014, and United States patent application Ser. No. 14/538,332 entitled "Specimen Sample Holder for Workpiece Transport Apparatus" filed on Nov. 11, 2014 the disclosures of which are incorporated herein by reference in their entireties.

In one aspect the workpieces are held in cassettes 102 and the cassettes 102 are held in one or more magazines 105 that are configured for insertion into the automated transport and positioning system 100 as will be described below. The magazine 105 and cassettes 102 therein are configured to provide for the automatic loading and removal of the cassettes 102. For example, the magazine 105 and cassettes 102 include kinematic features that permit substantially direct handling of the magazine 105 and cassettes 102 (e.g. as a unit or individually) by an automated handling system within the automated transport and positioning system 100 and external to the automated transport and positioning system 100. In one aspect the magazine 105 and cassettes 102 are configured for use in vacuum environments while in other aspects the magazine 105 and cassettes 102 are configured for use in non-vacuum environments. In one aspect the cassettes 102 and magazine 105 are configured for use in cryogenic environments or any other suitable environment having any suitable temperatures. In one aspect the cassette 102 and magazine 105 are substantially similar to that described in U.S. Provisional Patent application No. 61/902,470 filed on Nov. 11, 2013 and United States patent application Ser. No. 14/538,327 entitled "Workpiece Holder for Workpiece Transport Apparatus" filed on Nov. 11, 2014, the disclosures of which are incorporated herein by reference in their entireties.

Figure 1B:
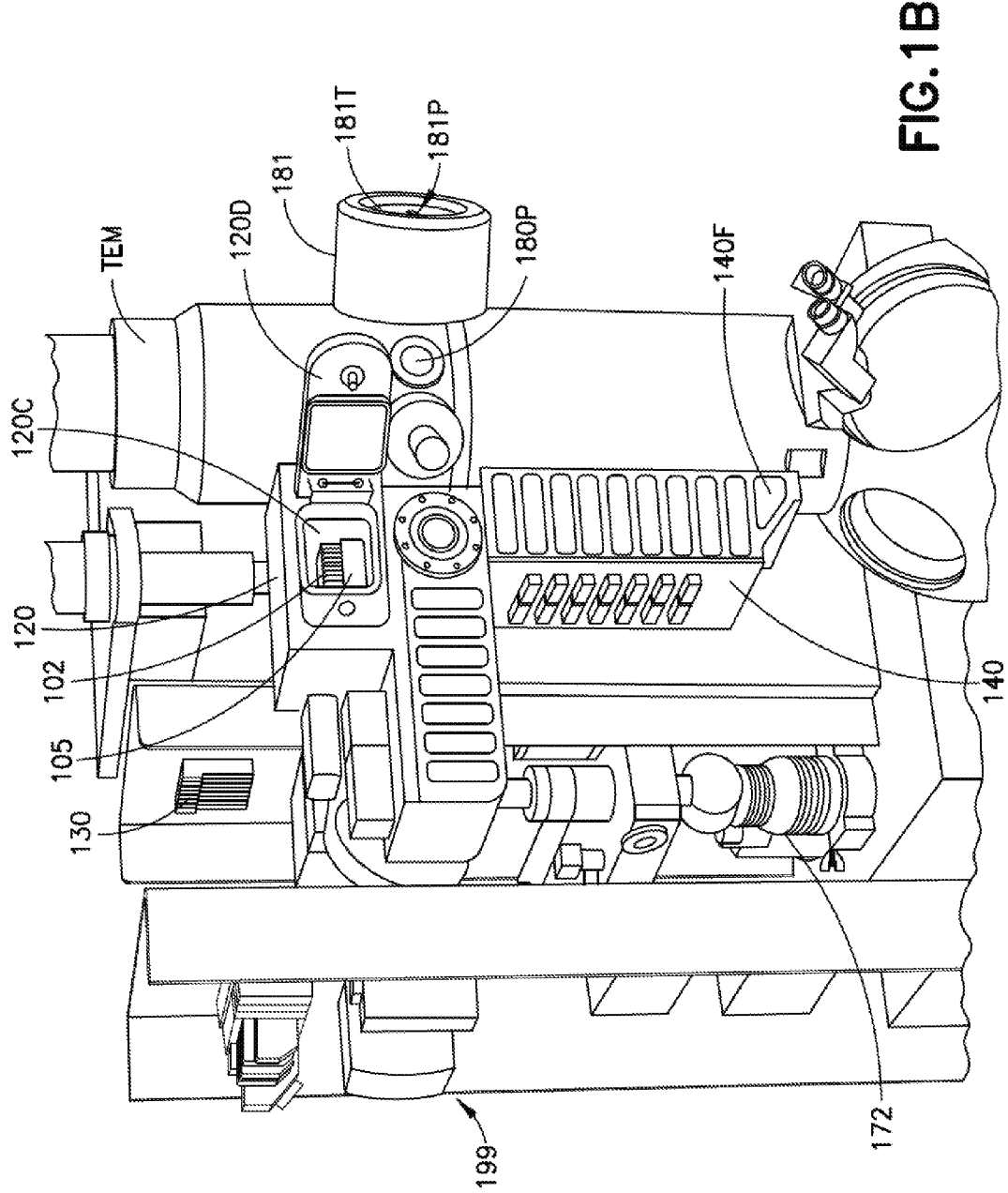
Figure 1D:
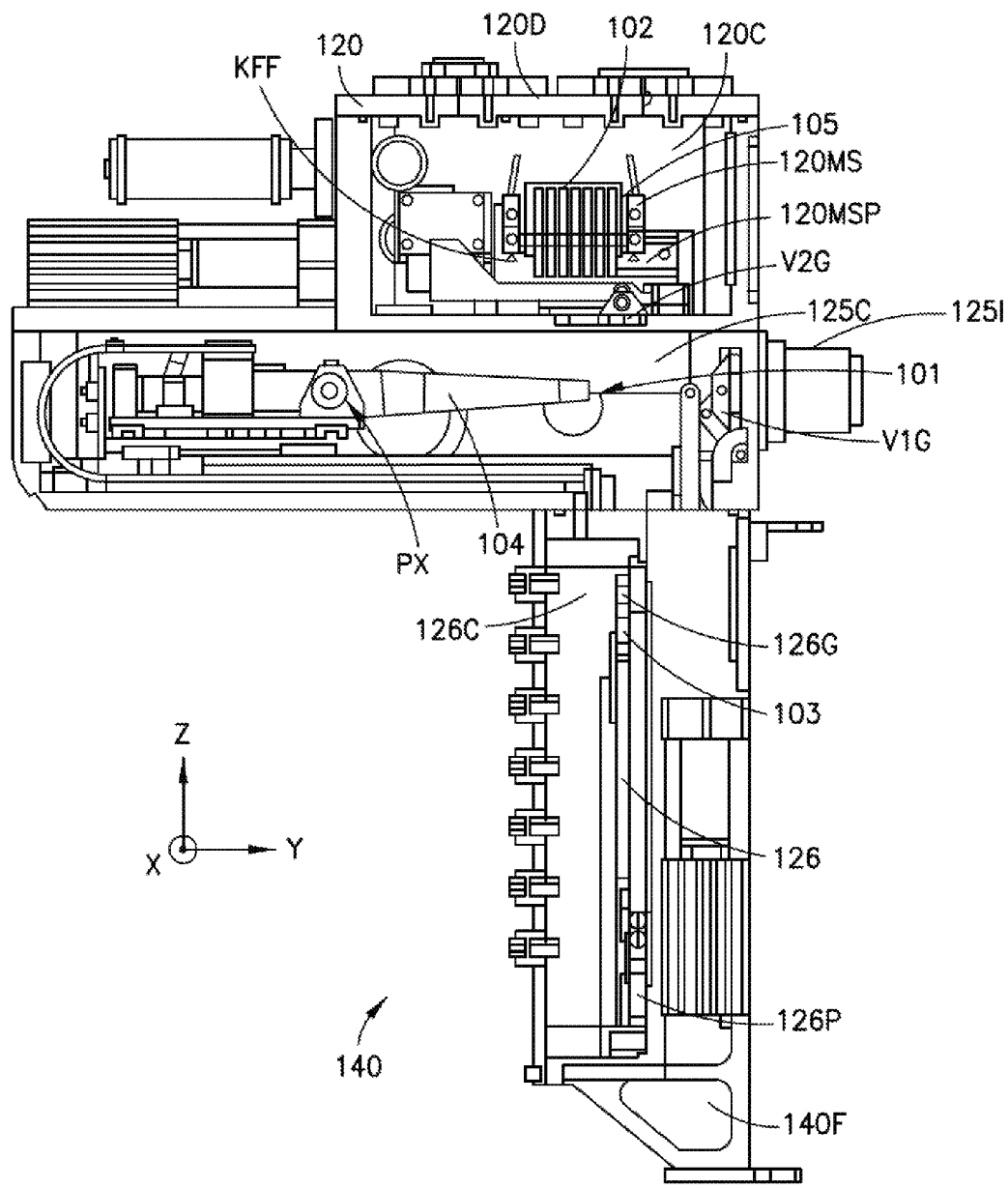

Still referring to FIG. 1A (1A-1,1A-2) and also to FIGS. 1B-1D the automated transport and positioning system 100 includes a frame 140F, transport and positioning unit 140 connected to the frame 140F, a pneumatics module 130 (which may be connected to the frame) and communicably coupled to the transport and positioning unit 140, and a vacuum module 172 (which may be connected to the frame) and communicably coupled to the transport and positioning unit 140. In one aspect the pneumatics module 130 includes an air source 130S and any suitable valves V1G, V2G, V3T, V4R, V5R, V6 for operating, e.g., valves and closures of the transport and positioning unit 140 and/or vacuum module 172 described herein. The vacuum module 172 includes any suitable vacuum pumps P1R, P2T, P3I and gauges G1R, G2H, G3H, G4H for pumping and maintaining the internal chambers of the transport and positioning unit 140 at any suitable vacuum pressure for interfacing with, for example, the TEM or other suitable process module PM. In one aspect the vacuum module 172 also includes any suitable valves V3T, V4R, V5R, V6, V7T, V8V, V9V for selectively isolating, e.g., the vacuum pumps from each other and/or from the chambers of the transport and positioning unit 140.

Figure 1E:
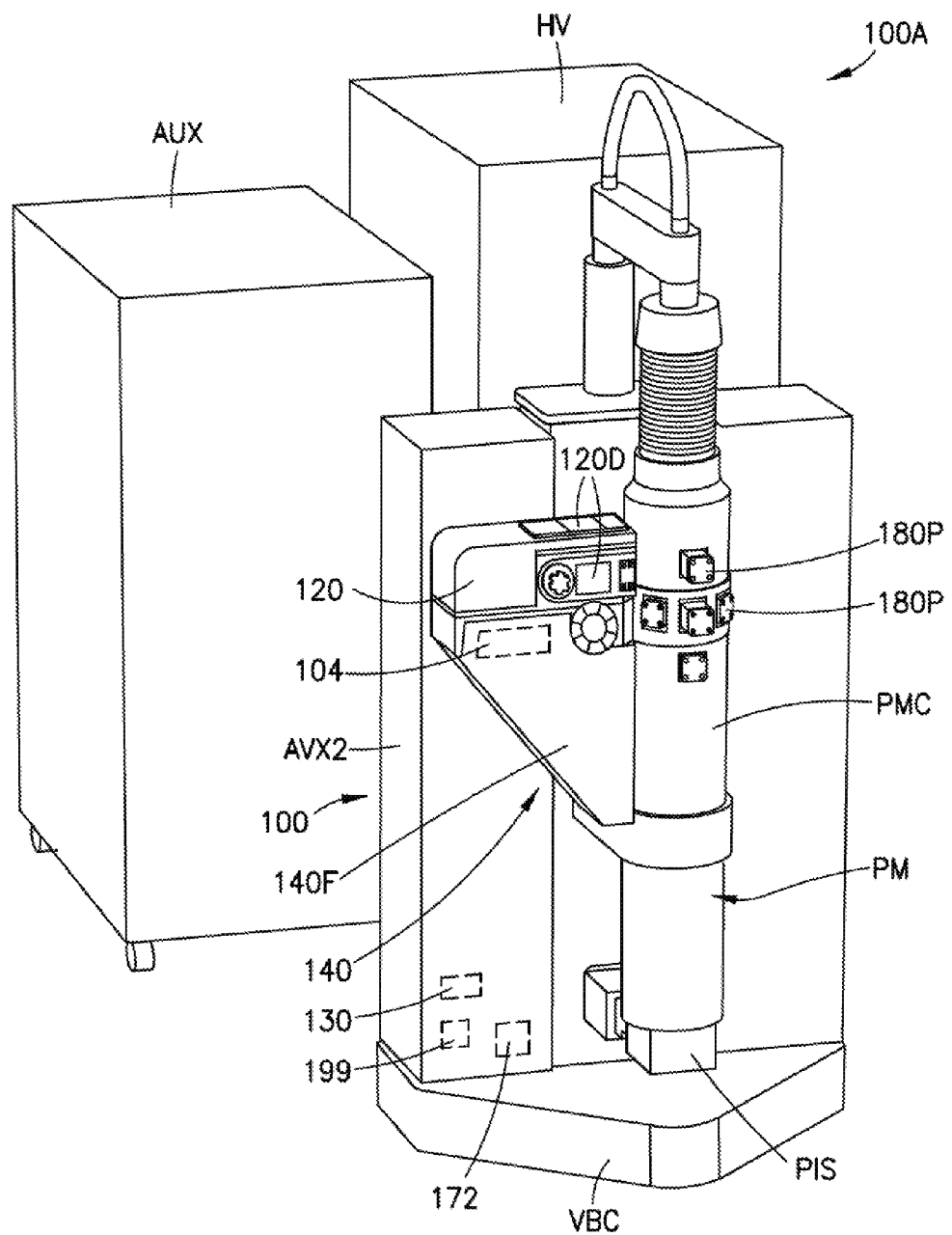
FIGS. 1E-1G are schematic illustrations of portions of an automated electron beam microscope including the automatic specimen/sample loading system of FIGS. 1A-1D and 1H in accordance with aspects of the disclosed embodiment.
Figure 1F:
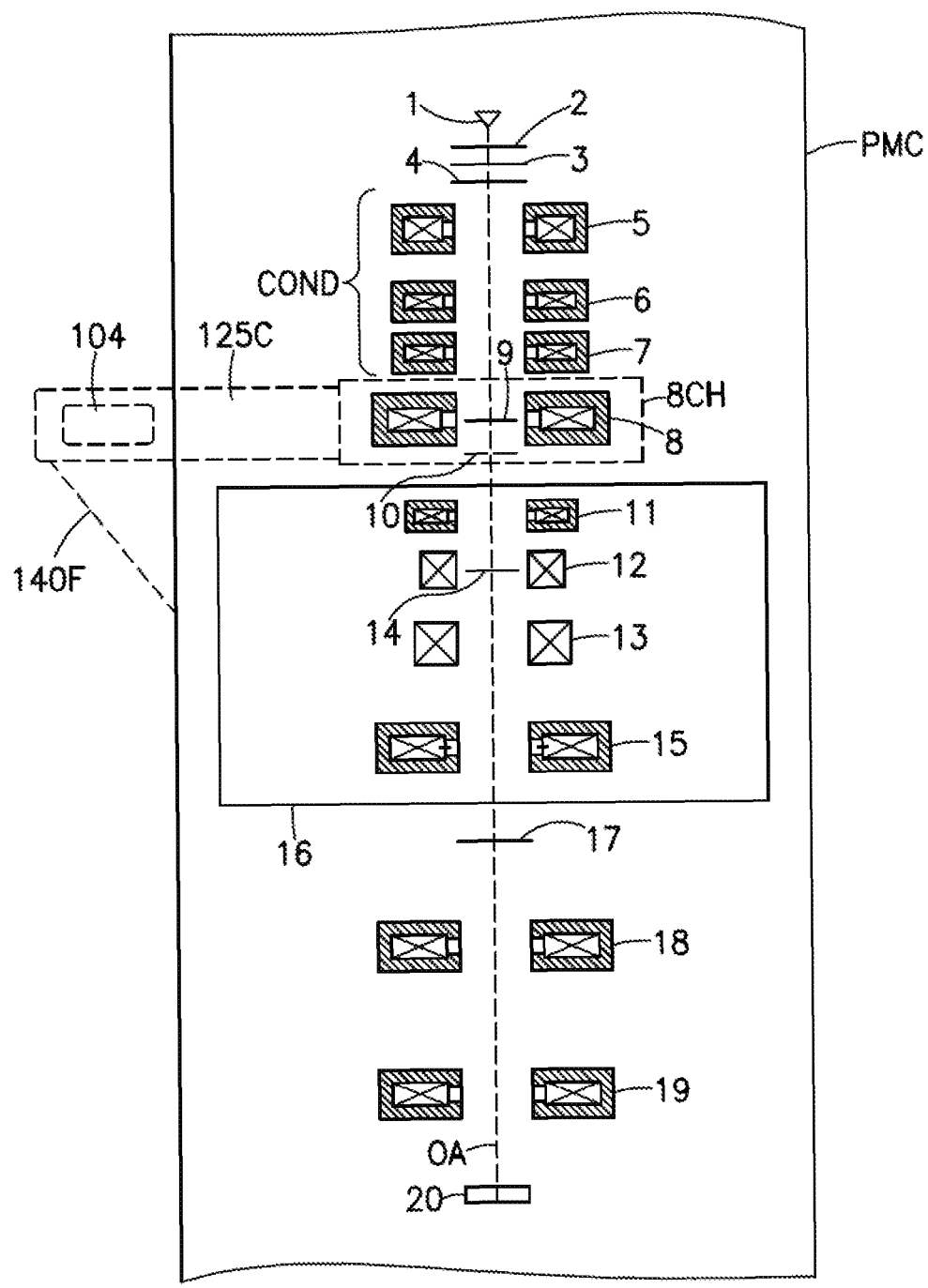

In one aspect the frame 140F forms or is integral (e.g. of one piece unitary construction) to at least part of the transport and positioning unit 140. In other aspects the transport and positioning unit 140 is connected to the frame 140F in any suitable manner. In one aspect the transport and positioning unit 140 includes an automated loading and transport section or load lock 120 having a sealable chamber 120C and a transport module or section 125 having a sealable transport chamber 125C. The chamber 120C is selectively communicably connected to the chamber 125C through a closable opening or port 120P. In one aspect the transport and positioning unit 140 includes any suitable gate valve V2G configured to selectively seal the port 120P for sealing or otherwise isolating an atmosphere of the chamber 120C from an atmosphere of the chamber 125C. The load lock 120 includes any suitable door 120D configured to seal a loading opening of the load lock 120. While a single door 120D is illustrated in the figures as being located on a side of the chamber 120C it should be understood, in other aspects, the single door 120D is located on a top of the chamber 125C (see FIG. 1D—e.g. to allow for automated opening and closing of the door for overhead loading of magazines 105 in the chamber) or in still other aspects more than one door (e.g. on a top and on a side—see FIG. 1H) provides access to the chamber 125. In one aspect the door is hinged to the load lock 120 while in other aspects the door is removable from the load lock 120D for allowing access to the chamber 120C. In one aspect the door 120D has a manual closure, and in other aspects the door 120D has an automated closure. In other aspects the chamber 120C may not include a door such that the atmosphere within chamber 125C is cycled between, for example, a process atmosphere and atmospheric pressure when cassettes are introduced and removed to and from the chamber 125C. The loading opening is configured to allow ingress and egress of one or more workpieces to and from the chamber 120C. In one aspect, as will be described further below, the workpieces are TEM grids held by cassettes 102 which in turn are held in a magazine 105. In one aspect the load lock includes an automated transport shuttle 120MS including a positioner unit 120MSP. The positioner unit 120MSP includes any suitable motors and/or guides for allowing movement of the transport shuttle 120MS within the chamber 120C and be configured for operation in one or more of a vacuum or atmospheric environment. The positioner unit 120MSP includes any suitable drive or motor A1L for moving the transport shuttle 120MS along at least the Y axis. In one aspect the motor A1L is a DC stepper motor that drives a screw drive for positioning the transport shuttle 120MS with a positioning resolution of about 5 um. In other aspects the motor is any suitable motor having any suitable positioning resolution such as a piezo motor, brushless or brushed motors, etc. The transport shuttle 120MS is configured to hold one or more magazines 105 and transport or otherwise move the magazines (e.g. via the positioner unit 120MSP) in one or more of the X and Y directions so that a predetermined cassette 102 is aligned with the port 120P for transport into the chamber 125C as will be described below. The transport shuttle 120MS includes any suitable kinematic features that mate with corresponding kinematic features (described below) of the magazine 105 for positioning the magazine relative to the transport shuttle 120MS. As may be realized, in one aspect, the kinematic features are also configured so that the magazine 105 can be placed on the transport shuttle 120MS in only one predetermined orientation. In other aspects, the transport shuttle 120MS includes any suitable features for positioning the magazine 105 on the transport shuttle 120MS in any suitable number of orientations and in any suitable manner. In one aspect the magazines 105 and the load lock 120 are configured for manual operator insertion and removal of the magazine 105 to and from the load lock 120 while in other aspects the magazines 105 and the load lock 120 are configured for automated insertion and removal of the magazine 105 to and from the load lock 120.

In one aspect the transport module 125 includes a process module interface 125I configured to couple and uncouple the transport and positioning unit 140 to and from a corresponding interface, such as interface or port 180P, of the process module PM so that the loading unit can be installed to or removed from the process module PM as a unit. The process module interface 125I includes a closable opening or port 125P that communicably connects the chamber 125C with an interior of the process module PM. The transport and positioning unit 140 includes any suitable gate valve V1G configured to selectively seal the port 125P for sealing or otherwise isolating an atmosphere of the chamber 125C from an internal atmosphere of the process module PM.

In one aspect the transport module 125 includes a cassette shuttle chamber 126C communicably connected to the chamber 125C. The cassette shuttle chamber 126C includes a workpiece or cassette shuttle 126 that is driven along any suitable axes by a workpiece shuttle positioner 126P. The workpiece shuttle positioner 126P includes any suitable drives or motors A2L and/or guides for allowing movement of a cassette shuttle gripper 126G along at least the Z axis. In one aspect the motor A2L is an ultrasonic piezo motor with less than about 1 um positioning resolution while in other aspects the motor A2L is any suitable motor having any suitable position resolution such as stepper motors, brushless motors, brushed motors, etc. The cassette shuttle gripper 126G is opened and closed in any suitable manner by any suitable drive A9R (e.g. such as by a two-state or open/closed actuator). In one aspect the workpiece shuttle 126 is a linear stage configured to move (via the workpiece shuttle positioner 126P) a cassette gripper 126G mounted to the workpiece shuttle 126 into a position (e.g. through the port 120P) for picking/removing and placing/inserting a cassette 102 from and to a magazine 105 located in the chamber 120C. The workpiece shuttle 126 is also configured to move the cassette 102, held by the cassette gripper 126G, to a predetermined pick/place position or workpiece holding station 176 along at least the Z axis to allow the end effector 101 of the workpiece positioning unit 104 to remove and/or insert a workpiece from and/or to the cassette 102. In one aspect the workpiece shuttle 126 is also configured to move the cassette 102, held by the cassette gripper 126G, to a predetermined buffer position (as will be described below) to allow the workpiece positioning unit 104 to move along at least the Y axis for transporting the workpiece to the processing module PM for processing without returning the cassette 102 to the magazine 105.

In one aspect a workpiece pre-aligner stage 103 is mounted to the cassette shuttle 126 (e.g. the pre-aligner stage and the cassette shuttle 126 move along at least the Z axis as a unitary member) for aligning workpiece prior to or post processing of the workpieces in the processing module PM. In other aspects the pre-aligner stage 103 is mounted to the frame 140F independent of the cassette shuttle 126 so that the pre-aligner stage is stationary along the Z axis or is movable along the Z axis independent of the cassette shuttle 126. The pre-aligner stage 103 includes any suitable drive A8R configured to provide rotation of the workpiece about the Z axis. In one aspect the drive A8R includes a brushless DC motor, an 800:1 gearbox (or any other suitable gearbox having any suitable drive ratio) and an encoder providing about 0.03 degree resolution. In other aspects the drive A8R is any suitable motor having any suitable gearbox and encoder providing any suitable degree of resolution. In operation, as will be described below, the workpiece positioning unit 104 picks a workpiece 400 (see e.g. FIG. 1A (1A-1,1A-2) for exemplary purposes only) from a cassette 102 and transport the workpiece to a rotational chuck of the pre-aligner stage 103 for workpiece orientation.

As may realized, the aspects of the disclosed embodiment illustrated in, for example, FIGS. 1B and 1C are illustrated with the automated transport and positioning system 100 being connected or otherwise coupled to a process module, such as a conventional TEM, SEM, DB-FIB, STEM or other suitable electron beam scanning/imaging device, for automatically transporting workpieces 400 into a column of the process module PM and for positioning the workpiece 400 in front, for example, the electron beam to take images of a specimen sample mounted to the workpiece 400. In other aspects, a purpose built processing system 100A that includes a process module PM and the automated transport and positioning system 100 is provided. The purpose built processing system 100A improves integration of the automated transport and positioning functions (as described herein) of the automated transport and positioning system 100 with an automated electron beam microscope/process module PM. In one aspect the purpose built system 100A includes only the required microscope components (e.g. such as the auxiliary system AUX and power supply as described below), electron optics, camera/imager and any suitable analysis software (such as to track and analyze the processing of the specimens). In one aspect the purpose built system is stripped of one or more manually operated features that are included with, for example, a conventional electron beam microscope/process module to provide an automated and lower cost imaging/analysis system in which the functions of the electron beam microscope/process module and the automated transport and positioning system are integrated into a common system.

Referring to FIGS. 1E-1H the purpose built processing system 100A includes a processing module PM, the automated transport and positioning system (ATPS) 100, electron beam auxiliary systems AUX, ATPS auxiliary systems AUX2, a vibration control platform VBC and an electron beam high voltage power supply HV. The processing module PM, is in one aspect configured as a TEM but in other aspects the process module is configured as an SEM, a DB-FIB, STEM or any other suitable electron beam microscope/scanning/imaging device. For exemplary purposes only, the processing module PM includes a column or housing PMC connected to a process module frame PMF, a portion of which defines an objective lens chamber 8CH. In one aspect, the transport and positioning unit 140 of the automated transport and positioning system 100 has an integral casing 140F with, for example, an objective lens chamber 8CH of the electron microscopy system where the integral casing forms a transport chamber 125C having a common atmosphere with the objective lens chamber 8CH. The column PMC generally includes electron optics such as any suitable electron source 1 (e.g. having a voltage source HV), an extraction electrode 2, a first electrode 3 and at least a second electrode 4 which are arranged along optical axis OA. The extraction electrode 2 is located downstream of the electron source 1 and is configured to extract electrons from the electron source 1. The first electrode 3 is configured to focus the source position and the at least one second electrode 4 is provided for accelerating the electrons coming from the electron source 1 (as may be realized the at least one second electrode 4 allows for an adjustable energy of the electron beam EB).

In the remaining length of the optical axis OA a multistage condenser COND is provided and includes three magnetic lenses (e.g. a first magnetic lens 5, a second magnetic lens 6 and a third magnetic lens 7), to which an objective 8 in the form of a magnetic lens with an objective aperture 10 is arranged. As noted above, the objective 8 and objective aperture 10 are disposed in a portion of the column PMC that forms the objective lens chamber 8CH. As may be realized, the objective lens chamber 8CH is described herein with respect to the purpose built processing system 100A but is should be understood that other suitable electron microscopy systems such as TEM, SEM, DB-FIB and STEM include objective lens chambers defined by an area of the electron microscopy column in which the objective lens(es) are located and in which the specimen is placed for imaging. An object plane 9 on which a specimen sample to be examined is located (as described herein) is provided on or adjacent to the objective 8. A corrector 16 is located downstream from the objective 8 and is configured to correct, for example a spherical aberration of the objective 8. In one aspect the corrector 16 includes a first transfer lens 11 (which in one aspect is a magnetic lens) that is configured to image a rear focal plane of the objective 8 and generate a real intermediate image 14 of the object plane 9. A first correction system 12 (which in one aspect is a multipole) is provided in the plane of the intermediate image 14 generated by the first transfer lens 11. A second correction system 13 (which in one aspect is a multipole) and a second transfer lens 13 are connected downstream from the first correction system 12. The second transfer lens 15 images the intermediate image 14 of the object plane 9 in an input image plane 17 of a projector system including lenses 18, 19. The projector system 18, 19 generates an image on a detector 20 (e.g. of imaging system PIS) of the sample situated in the object plane 9 and imaged in the input image plane 17 of the projector system 18, 19. Again, it is noted that the configuration of the process module PM described above is for exemplary purposes only and in other aspects the process module includes any suitable components forming a TEM, SEM, DB-FIB or any other suitable electron beam scanning/imaging device.

The column PMC includes, in one aspect, one or more interface ports 180P. In one aspect, the one or more interface ports 180P include motorized apertures for inserting specimen samples into the column PMC in any suitable manner for imaging/analysis.

Figure 1G:
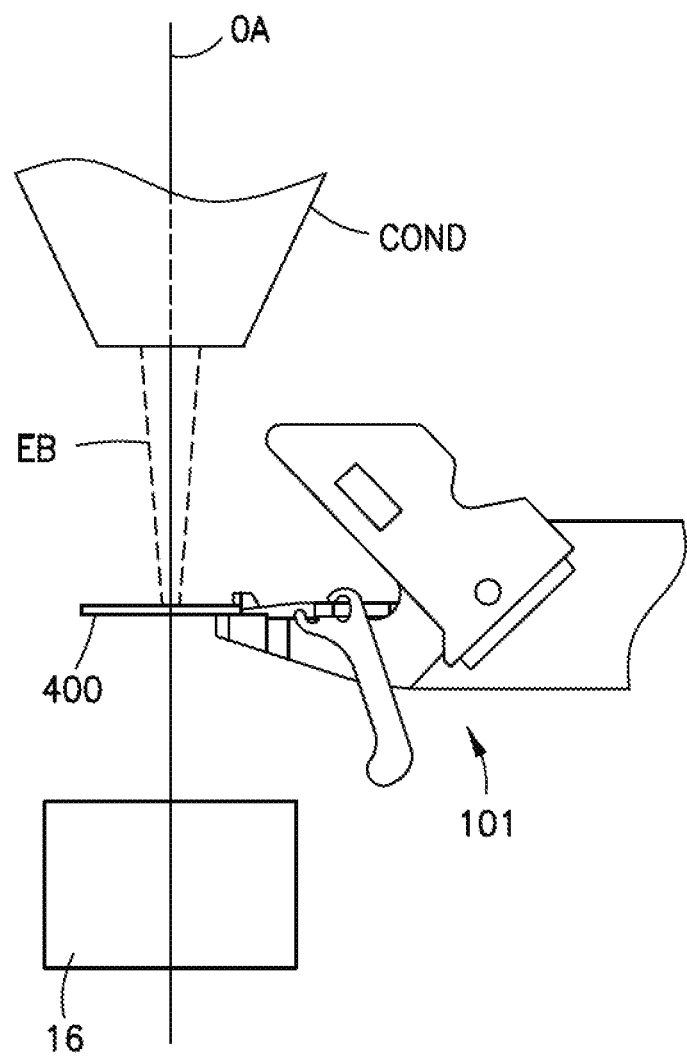
Figure 1H:
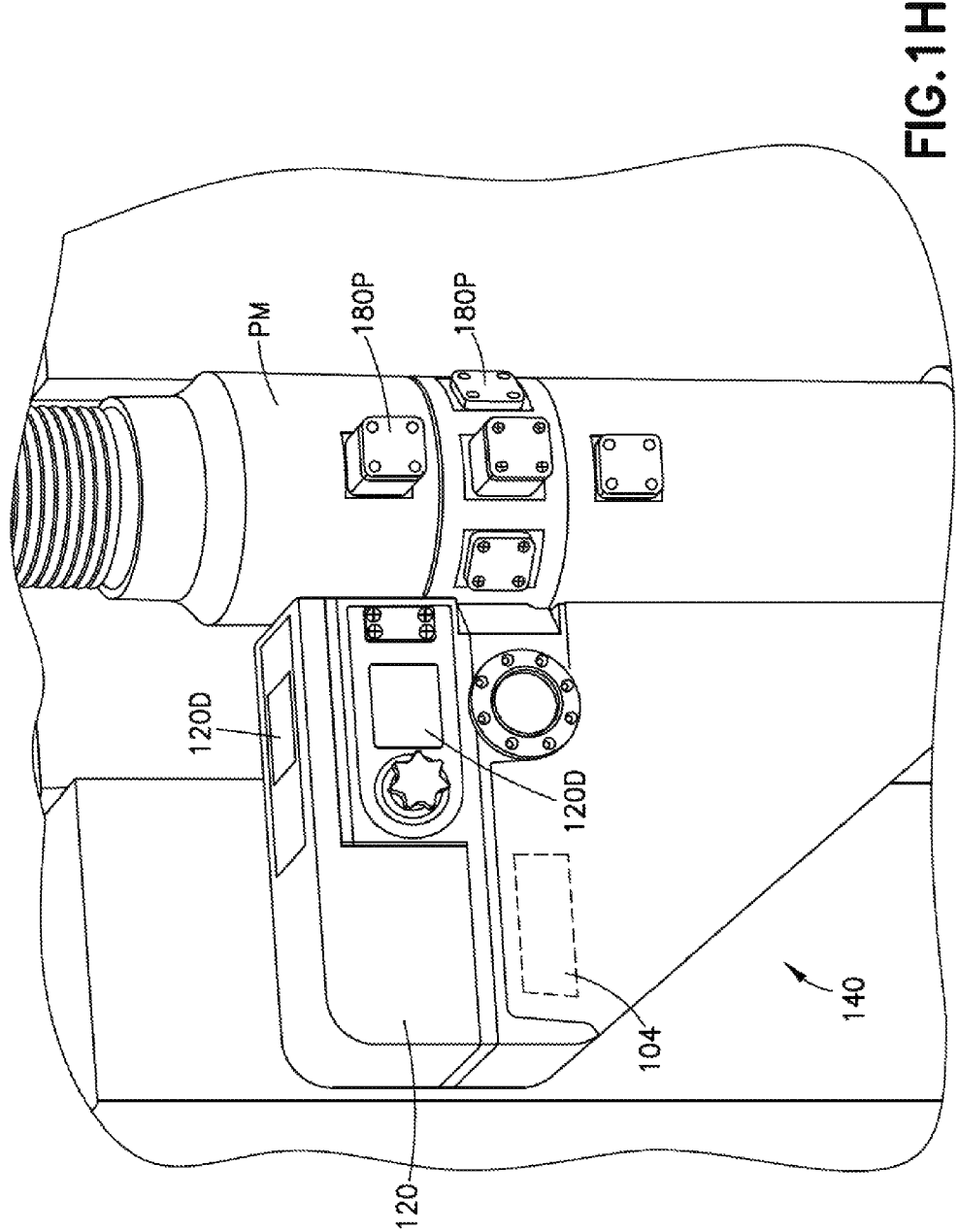

The automated transport and positioning system 100, as described herein includes frame 140F that is coupled to or integrally formed with the process module frame PMF so that the workpiece positioning unit 104 is located relative to the column for positioning the workpiece 400 within the objective lens chamber 8CH in, for example, the object plane 9 and within the electron beam EB (as illustrated in FIG. 1G), where the workpiece 400 is held on the end effector 101 of the workpiece positioning unit 104, as described herein, during imaging of the specimen such as for tomography inspection or for any other suitable imaging process. In one aspect, the workpiece positioning unit extends through a port 180P of the column PMC. In one aspect the automated transport and positioning system 100 includes auxiliary systems AUX2 that include, for example, the vacuum module 172, the pneumatics module 130 and controller 199 as described herein. In one aspect the process module PM and the automated transport and positioning system 100 are mounted on or otherwise supported by any suitable vibration control platform VBC. In one aspect the vibration control platform VBC is an active vibration control platform including any suitable actuators configured to cancel any vibrations that occur in the system 100A while in other aspects the vibration control platform VBC is a passive vibration control platform configured to cancel vibration in the system 100A in any suitable manner.

The system 100A, in one aspect also includes an auxiliary system AUX and power supply HV for the process module PM. In one aspect the auxiliary system AUX includes a vacuum system, a cooling system and a control system (which in one aspect is connected to or integral with control 199) for the process module. The power supply HV is any suitable power supply such as, for example, a high voltage power supply. As may be realized, the configuration of the purpose built processing system 100A described herein is exemplary and for illustration purposes only and in other aspects the purpose built processing system 100A has any suitable configuration for imaging and tracking samples as described herein.

Figure 2A:
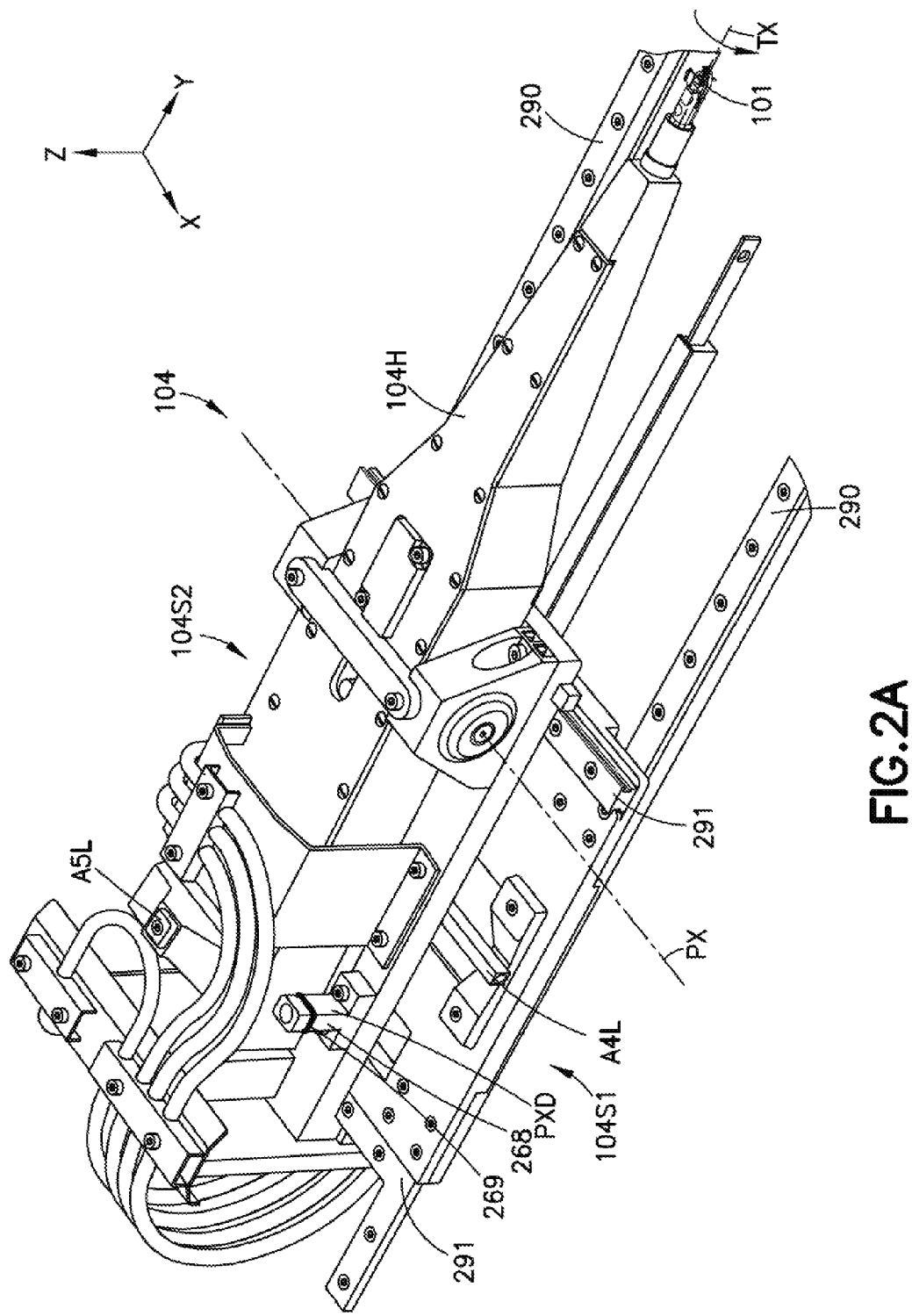
Figure 2B:
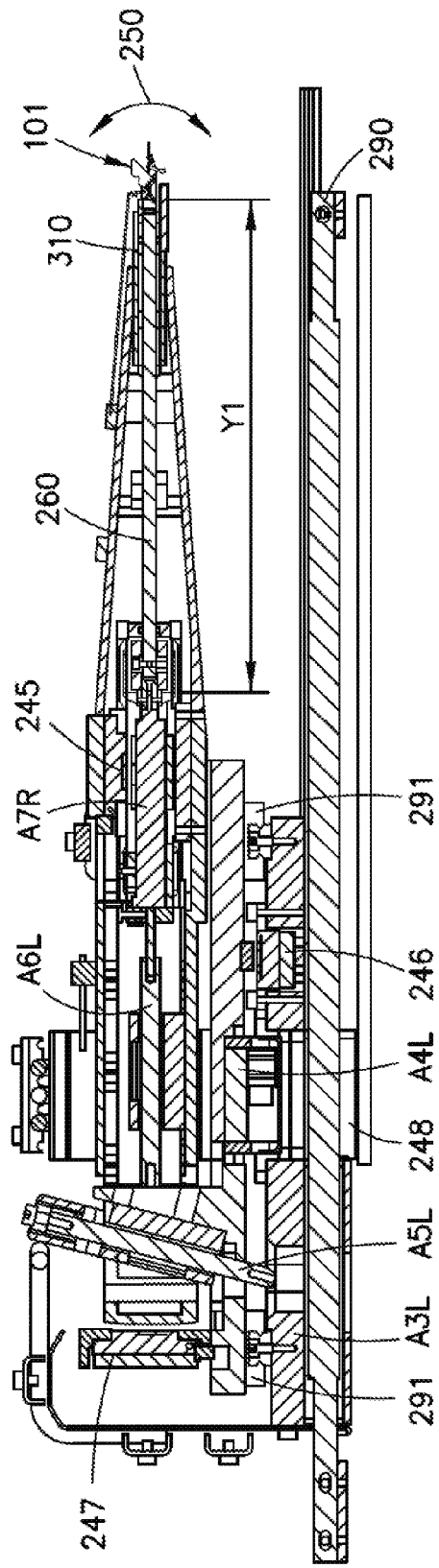
Figure 2F:
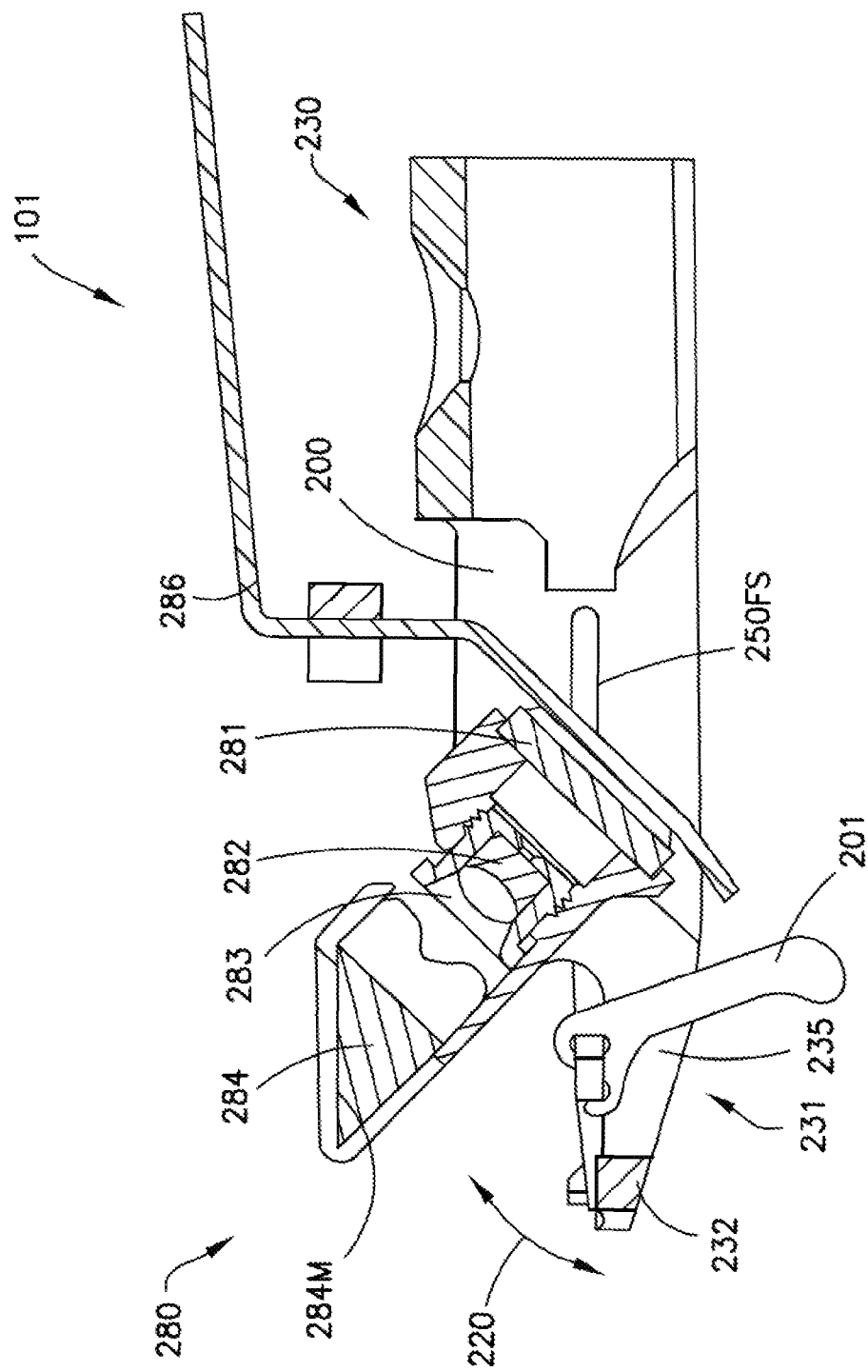
Figure 2G:
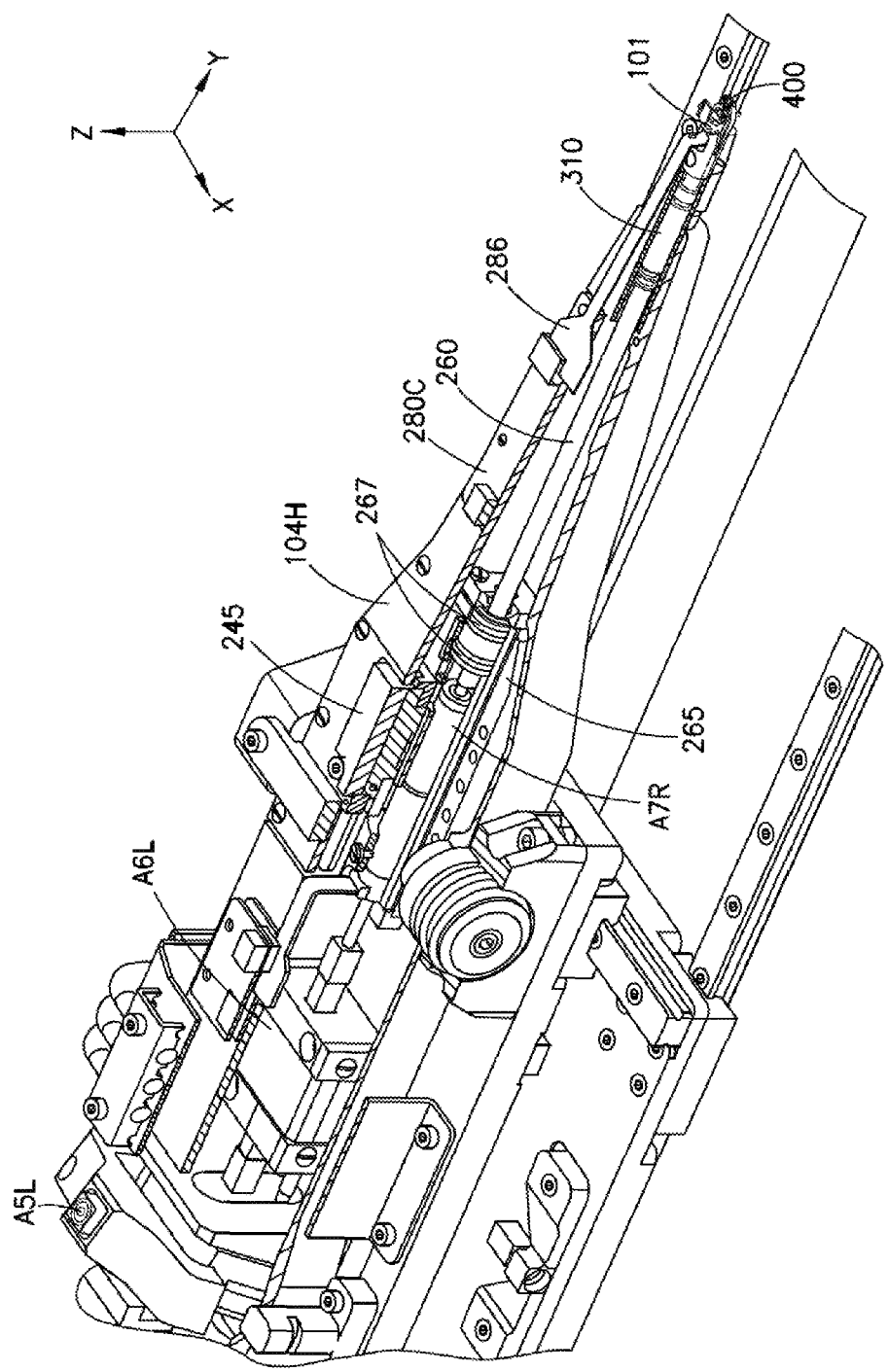

Referring also to FIGS. 2A, 2B and 2G, the transport module 125 includes the workpiece positioning unit or multistage shuttle 104 which is configured to pick/place workpieces from cassettes 102, transport the workpieces to the processing module PM and support the workpieces during processing within the processing module PM. The workpiece positioning unit 104 includes a first shuttle stage 104S1 (gross positioning stage) having multiple degrees of freedom of movement configured to move the end effector 101 along at least the X, Y axes and about pitch axis PX. The workpiece positioning unit 104 also includes a second shuttle stage 104S2 (fine positioning stage) that is carried by the first stage but is separate and distinct from the first stage in its operation. The second shuttle stage 104S2 includes multiple degree of freedom movement, independent of the first shuttle stage 104S1, configured to move the end effector 101 along at least the Y axis and about the tilt axis TX (e.g. the alpha tilt axis). The combined movements of the first and second shuttle stages 104S1, 104S2 provide the end effector 101 with a range of motion extending from a workpiece holding station (e.g. the predetermined pick/place position 176 of the cassette 102 noted above) outside the processing module PM to a processing location 177 inside the processing module PM for positioning the workpiece at the processing location 177 so that the end effector 101 defines a processing stage of the processing module PM.

The first shuttle stage 104S1 includes a Y axis drive or motor A3L, an X axis drive or motor A4L and a pitch axis PX drive or motor A5L. While the first shuttle stage 104S1 is described and illustrated as being mounted to the frame 140F, in other aspects the first shuttle stage 104S1 is configured with a separate and distinct mechanical docking or locking interface that mates with corresponding features of the process module PM. It is noted that, in one aspect, each of the drives A3L, A4L, A5L (as well as the other drives described herein) respectively include any suitable encoders 248, 246, 247 which are, for example, optical encoders, laser interferometric encoders, capacitive or inductive encoders or any other suitable encoder or combinations thereof. In one aspect the encoders described herein have a picometer position resolution while in other aspects the encoders have any suitable position resolution that may be consistent with the positioning resolution of a respective drive motor of the axis along which the encoder is providing position data. In still other aspects the encoders described herein have a positioning resolution that is larger or smaller than the position resolution of the respective drive motor. In other aspects the drives described herein employ any suitable integral position sensing capabilities of the drives. It is noted that, in one aspect, any suitable portions of the drives A3L, A4L and A5L are sealed from an atmosphere of the chamber 125C for isolating components, such as motors, to allow operation of the drives in a vacuum environment. In other aspects drives A3L, A4L and A5L are configured to operate in a vacuum environment in any suitable manner while in still other aspects the drives are configured to operate in an atmospheric environment. The Y axis (or longitudinal) drive A3L includes any suitable motor and a linear stage having any suitable mechanical and/or solid state electromagnetic (and/or permanent magnet) guides 290 for translating the end effector 101 along the Y axis. In one aspect the motor is an ultrasonic piezo motor with less than about 1 um positioning resolution while in other aspects the motor is any suitable motor having any suitable positioning resolution such as a stepper motor, brushless motor, brushed motor, etc. The drive A3L is configured to move the end effector towards and away from the cassette 102 (e.g. held by the cassette gripper 126G of the cassette shuttle 126) for picking and placing workpieces from and to the cassette 102 and transporting the workpiece along the Y axis any suitable desired distance. The drive A3L is also configured to move the end effector 101 into the processing module PM for processing of the workpiece held by the end effector 101.

The X axis (or lateral) drive A4L includes any suitable motor and a linear stage having any suitable mechanical and/or solid state electromagnetic (and/or permanent magnet) guides 291 for translating the end effector 101 along the X axis. In one aspect the motor is a stepping piezo motor with picometer range positioning resolution while in other aspects the motor is any suitable motor having any suitable positioning resolution such as a stepper motor, brushless motor, brushed motor, etc. While the drives A3L and A4L are illustrated as being stacked (e.g. one drive is mounted to the other drive), in other aspects the X and Y drives of the first shuttle stage 104S1 are a combined two-dimensional drive having any suitable configuration such as a magnetically suspended platen capable of movement along one or more of the X and Y axes. The drive A4L is configured to move the end effector laterally along the X axis in the chamber 125C so that all columns in the cassette 102 (e.g. held by the cassette gripper 126G of the cassette shuttle 126) as well as the pre-aligner stage 103 are accessed by the end effector 101 for workpiece picking and placing operations. In one aspect the drive A4L is also configured to move the end effector (and the workpiece located thereon) within the processing module PM in the X direction to provide motion of the workpiece in the X direction during processing of the workpiece.

The pitch axis PX drive A5L includes any suitable motor for pivoting the second shuttle stage 104S2 about the pitch axis PX. For example, second shuttle stage 104S2 may be pivotally mounted to the first shuttle stage 104S1 in any suitable manner such that the second shuttle stage is rotatable or pivotable about the pitch axis PX. The drive A5L is coupled to both the first shuttle stage 104S1 and to any suitable portion of the second shuttle stage (e.g. such as a housing 104H of the second shuttle stage) in any suitable manner that allows the drive A5L to pivot the second shuttle stage 104S2 about the pitch axis PX. In one aspect any suitable damper PXD is provided at any suitable location, such as mounted to the first shuttle stage 104S1 and is configured to provide lateral support and dampening to the housing 104H. In one aspect the damper PXD includes a post 268 and any suitable elastomeric element 269 configured to engage and dampen lateral movement of the housing 104H (and the end effector 101). Pivotal movement of the second shuttle stage 104S2 about the pitch axis causes movement of the end effector 101 in the direction of arrow 250. Movement of the end effector 101 in the direction of arrow 250 about the pitch axis PX serves to move the workpiece along the Z axis and approximates a translation which is used for positioning the workpiece at, for example, a predetermined processing location (e.g. such as at the euccentric location of a TEM beam). In one aspect, the drive A5L is also utilized for small (e.g. less than about ±3 mm) Z axis motions during picking and placing of workpieces to and from the cassette 102 and/or pre-aligner stage 103. In one aspect the drive A5L includes a stepping piezo motor with picometer positioning resolution while in other aspects the motor is any suitable motor having any suitable positioning resolution such as a stepper motor, brushless motor, brushed motor, etc. In other aspects the workpiece positioning unit 104 is provided with a Z axis drive configured to move one or more of the first or second shuttle stage 104S1, 104S2 (or any other suitable portion of the workpiece positioning unit 104) along the Z axis so that the workpiece positioning unit 104 has, for example, 9 degree of freedom movement.

The second shuttle stage 104S2 includes an assembly having a housing 104H. In one aspect the housing 104H is a sealed housing to isolate, for example, an operating environment of the drive motors (and any other suitable components) from an environment (such as a vacuum environment) within the chamber 125C. The shape of the housing 104H illustrated in the figures is exemplary only and in other aspects the housing has any suitable shape. The housing 104H is configured to provide mass and stiffness to dampen end effector vibrations and reduce settling times. In one aspect the housing 104H houses a Y axis drive A6L (e.g. "fast axis") configured to move the end effector along the Y axis and a tilt axis drive A7R configured to rotate the end effector about the tilt axis TX. In other aspects the Y axis drive A6L may be omitted such that movement of the end effector along the Y axis is provided by the drive A3L. The Y axis (or longitudinal) drive A6L includes any suitable motor and a linear stage having any suitable mechanical and/or solid state electromagnetic (and/or permanent magnet) guides for translating the end effector 101 along the Y axis. In one aspect the motor is a stepping piezo motor with picometer positioning resolution while in other aspects the motor is any suitable motor having any suitable positioning resolution such as a stepper motor, brushless motor, brushed motor, etc. The drive A6L is configured to provide precision (e.g. fine positioning) and fast motion of the end effector 101 (and the workpiece held thereon) along the Y axis within the processing module after the drive A3L has positioned (e.g. gross positioning) the end effector within the processing module PM. Positioning the workpiece within the processing module PM provides maximized throughput when stepping across the workpiece to take a "column" of images (e.g. a series of images taken at different points along the Y axis of the workpiece) such as during TEM imaging. In this aspect nominal moves between 8 and 24 microns are completed with the drive A6L in less than 100 ms, where "completed" is defined as workpiece motion is settled to less than about 4 nm in about to about 35 ms. The aspects of the disclosed embodiment described herein effect high throughput scanning having an imaging rate greater than 2 images/second.

The tilt axis drive A7R is coupled to the drive A6L in any suitable manner for providing the end effector 101 with multiple degree of freedom movement. In one aspect the tilt axis drive A7R is mounted to any suitable bearing(s), such as linear bearing 265, that allow(s) the drive A7R to move along the Y axis with the end effector 101 when the end effector is positioned by the drive A6L. In one aspect any suitable preloaded thrust bearing assembly 267 is provided to substantially eliminate axial play of connecting member 260 (described below). In other aspects, the preloaded thrust bearing is omitted. As may be realized any suitable linear encoder 245 is mounted to or integrally formed with a housing of the A7R drive for providing position feedback of the A6L drive. In other aspects the linear encoder 245 (and/or rotary encoder for drive A7R) is incorporated with the connecting member 260 such that one or more scales are disposed on the connecting member at any point between the end effector and the drive A7R. As may be realized the encoder 245 includes absolute and/or incremental encoder scales. In one aspect the absolute encoder is positioned on the connecting member 260 between the bearing 310 and the drive A7R while the incremental encoder is positioned between the bearing 310 and the end effector. In still other aspects both the absolute and incremental encoders are positioned between the bearing 310 and end effector or between the bearing 310 and the drive A7R. In still other aspects one of the absolute and incremental encoders (or a portion thereof) is on a housing of the drive A7R while the other one of the absolute and incremental encoder is disposed on the connecting member 260. In one aspect the linear encoder 245 is, for example, an optical encoder, laser interferometric encoder, capacitive or inductive encoder or any other suitable encoder (it is noted that in one aspect each of the drives A1L, A2L, A3L, A4L, A5L, A6L, A7R, A8R include an encoder substantially similar to encoder 245). In other aspects, the Y axis drive A6L is coupled to the tilt axis drive A7R and is mounted with any suitable bearings to allow the drive A6L to rotate with the end effector 101 when the end effector is driven by the drive A7R. As noted above, the tilt axis drive A7R is configured to rotate the end effector 101 and the workpiece held thereon about the tilt axis TX at any suitable point during workpiece handling. For example, the drive A7R rotates the end effector 101 and the workpiece held thereon while the workpiece is within the process module PM to, for example, locate the euccentric point in a TEM beam as well as for tomography applications where the workpiece is tilted at varying angles such that images of the workpiece are taken at each of the varying angles. It is noted that, in one aspect, the A7R drive also includes any suitable encoder (such as those described above) for providing position feedback along the tilt axis TX. The drive A6L includes any suitable motor such as a piezo motor, a stepper motor, brushless motor, brushed motor, etc.

The end effector 101 is coupled to one or more of the drives A6L, A7R in any suitable manner such as by a connecting or driven member 260 that is supported within the housing 104H in any suitable manner, such as with one or more suitable bearing (see bearing 390) and/or one or more suitable damper (see dampers 320, 321) as will be described below with respect to FIGS. 3A-3D. In one aspect the connecting member is configured with a predetermined length Y1 and increased mass (e.g. via the positioning of drive A7R between connecting member and the drive A6L) and the housing 104H is configured to provide a predetermined stiffness so that the connecting member 260 is supported by one or more bearings 390 (e.g. substantially without dampers) while allowing movement the end effector 101 to settle within the times described herein. In other aspects one or more dampers (not shown) are also positioned within the housing 104H for settling the movement of the end effector 101 alone or in combination with the configuration of the connecting member 260, the configuration of the housing 104H and/or the bearings 390.

Referring now to FIGS. 2C-2F the end effector 101 includes a body 200 having any suitable configuration. In one aspect the body 200 is an integral (e.g. one piece unitary) member having a mounting portion 230 and a workpiece interface portion 231 extending from the mounting portion 230. The mounting portion 230 is configured to mount on or otherwise interface with the connecting member 260 in any suitable manner, such as by insertion of the connecting member 260 into a recess 200R of the body and securing the body to the connecting member 260 using any suitable chemical or mechanical fastener (which may pass through aperture 200A). In other aspects, the end effector 101 and connecting member 260 are configured such that the end effector has a "snap-on" interface with any suitable kinematic alignment features so that the end effector 101 is installed and/or removed from the connecting member 260 substantially without tools (e.g. tool-less installation) effecting a quick-change of end effector. The workpiece interface portion 231 includes a workpiece detecting member 280 and a workpiece interface member 232. The body 200 includes a slot 250 having a substantially flat surface 250FS on one side of the slot 250 and a diverging surface on the other side of the slot where the diverging surface forms a bearing 210 that will be described further below. The end effector 101 includes a gripper 101G having a gripper flexure 101GF and a gripper workpiece support surface 101GS. In one aspect the gripper workpiece support surface 101GS is integrally formed with the workpiece interface member 232. In one aspect the gripper workpiece support surface 101GS includes one or more integral workpiece bumpers 211 disposed adjacent the gripper workpiece support surface 101GS. The bumpers 211 have any suitable shape for interfacing with, for example a side edge of the workpiece and to position the workpiece (e.g. through substantial contact between the side edge of the workpiece and the bumpers 211) relative to the workpiece support surface 101GS and gripper tongs 101GT of the gripper flexure 100GF. In one aspect the workpiece interface member 232 also includes recesses on either side of the workpiece support surface 101GS in which the gripper tongs 101GT rest when a workpiece is not gripped by the gripper 101G and so that a relaxed state of the flexure is positioned below the workpiece support surface 101GS for effecting positive gripper engagement of a workpiece held by the gripper 101G. In one aspect the gripper flexure 101GF includes a base 101GFB, one or more flexure tines 101GFT extending away from one side of the base 101GFB and one or more gripper tongs 101GT extending from an another side of the base 101GFB in a direction substantially opposite a direction of extension of the flexure tines 101GFT. The flexure tines 101GFT are configured to extend into the slot 250 for securing the gripper flexure 101GF to the body 200 and biasing the gripper flexure towards the substantially flat surface 250FS of the slot 250. The one or more gripper tongs 101GT are configured to extend alongside the workpiece support surface 101GS. The workpiece interface member 232 includes an aperture 235 through which a lever member or spar 201 extends. The lever member 201 is coupled to the base 101GFB of the gripper flexure 100GF such that the lever member 201 extends through the aperture 201 beyond a peripheral surface of the body 200. It is noted that the gripper flexure 101GF is movable between the substantially flat surface 250FS of the slot and the bearing 210 for opening and closing the gripper.

The drive A6L and the drive A3L are configured for simultaneous operation along the Y axis in opposite directions to actuate the gripper 101G of the end effector 101 as will be described below. Movement of the drives A6L and A3L in opposite directions causes relative movement between the end effector 101 and the housing 104H of the second shuttle stage 104S2 (e.g. while maintaining the end effector 101 at a predetermined position) so that the lever member or spar 201 of the end effector 101 contacts a portion of the housing 104H. The contact between the lever member 201 and the housing 104H effects movement of the lever member 201 so that the lever member 201 causes the gripper flexure 101GF, to which the lever member 210 is coupled, to engage a bearing 210 of the end effector 101 such that the gripper flexure 101GF flexes to move the gripper tongs 101GT away from the gripper workpiece support surface 101GS in the direction of arrow 220 causing the gripper to open for picking or placing a workpiece. The gripper is closed in substantially the opposite way such that the lever member 201 is moved away from the housing 104H and a biasing force of the gripper flexure 101GF causes movement of the gripper tongs 101GT in the direction of arrow 220 towards the gripper workpiece support surface 101GS for closing the gripper or to otherwise grip a workpiece.

Figure 2H:
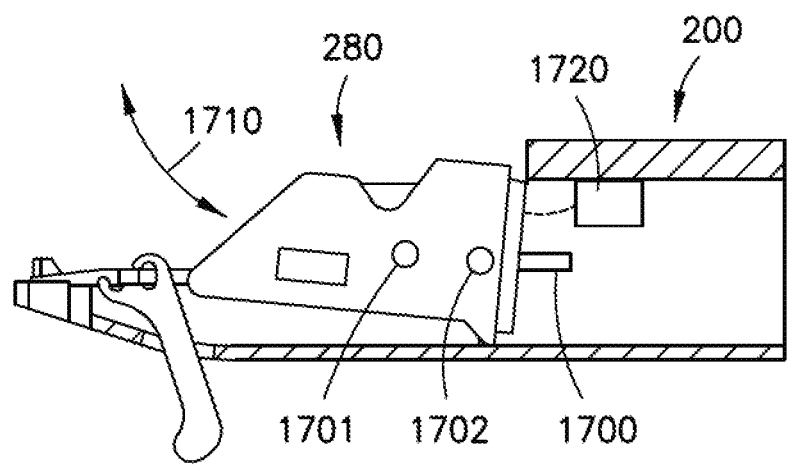
Figure 2I:
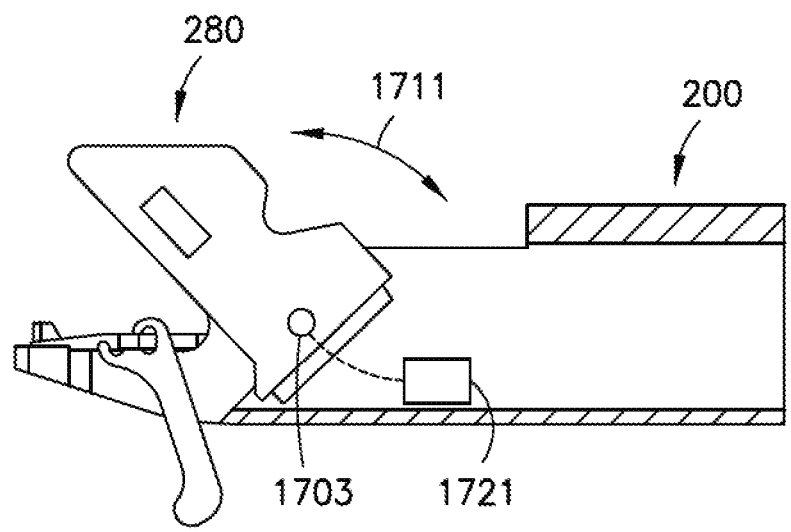

The workpiece detecting member 280 is mechanically mounted to the body 200 adjacent the workpiece gripper 101G for detecting or otherwise imaging the workpiece before, after and/or during workpiece handling. The mechanical mount between the workpiece detecting member 280 and the body 200 is a static mount (e.g. the workpiece detecting member 280 is fixed relative to the body 200) or a dynamic mount (e.g. allowing relative movement, automated or motorized movement or manual movement, between the workpiece detecting member 280 and the body) that provides for retraction of the workpiece detecting member 280 into, for example, the body 200 or any other suitable portion of the housing 104H. In one aspect the workpiece detecting member 280 is retracted prior to the end effector entering the process module PM while in other aspect the workpiece detecting member 280 is retracted at any suitable time. Referring also to FIGS. 2H and 2I, in one aspect the workpiece detecting member 280 (shown in a retracted position) includes guide members 1701, 1702 that engage rails 1700 so that that the workpiece detecting member 280 is movable in the direction of arrow 1710 between deployed and retracted positions. In other aspects, the workpiece detecting member 280 (shown in a deployed position) includes a pivot axis 1703 so that the workpiece detecting member 280 pivots in the direction of arrow 1711 between deployed and retracted positions. As may be realized, the workpiece positioning unit 104 includes any suitable actuators 1720, 1721 for moving the workpiece detecting member 280 in the direction of arrows 1710, 1711 or in any other suitable manner between the retracted and deployed positions.

In one aspect the workpiece detecting member 280 includes any suitable sensor 281, any suitable lens 282, any suitable lens mount 283 and a mirror 284 (such as a transparent prism with a mirrored surface 284M) having any suitable angle for allowing the sensor 281 to detect or otherwise image a workpiece held on the gripper 101G or otherwise near the gripper 101G. In one aspect the mirror 284 is configured to fold the optical path of the workpiece detecting member 280 to obtain a more compact configuration while in other aspects the workpiece detecting member 280 may not include a mirror. In one aspect the workpiece detecting member 280 also includes one or more suitable illumination member 285 for providing light of any suitable wavelength or wavelengths, to permit detection of the workpiece by the sensor 281. A flexible circuit 286 couples the sensor 281 to any suitable controller (such as controller 199 or any intermediate controller, such as a workpiece detecting member controller 280C that is connected to controller 199 and positioned at any suitable location such as on housing 104H) so that the sensor 281 provides signals to the controller where the controller is configured to perform any suitable image analysis on the signals (e.g. such as edge detection, bar code reading, fiducial detection, pseudo stereo location in which sequential images are taken from two different positions with parallel optical axes, etc.).

In other aspects the workpiece detecting member 280 is mounted to the housing 104H (or any other suitable location within the chamber 125C and/or on the workpiece positioning unit 104), with a static mount or a dynamic mount as described above, while providing a field of view in which the gripper 101G and any workpiece held by the gripper or adjacent the gripper can be viewed. It is noted that mounting the workpiece detecting member 280 to the housing eliminates the flexible circuit 286 from the end effector which decreases the movement settling times of the end effector. It is noted that the workpiece detecting member 280 (whether mounted to the housing or the end effector) moves as an integral assembly with the workpiece positioning unit 104.

In one aspect the sensor 281 is a camera or other optical detector while in other aspects a plurality of detectors, such as single device, 2D and 3D arrays (line scan, CCD, etc.) are incorporated to provide high fidelity concurrent data streams over a broad range of electromagnetic spectra. While only one sensor 281 is illustrated in the figures (e.g. monocular vision) in other aspects the end effector 101 has one or more sensors 281 and/or one or more sensors are mounted separate from the end effector in a manner similar to that described above. For example, the end effector has two sensors providing binocular or stereo vision enabling true stereo location (e.g. of the gripper relative to a workpiece or of a workpiece held by the gripper relative to a workpiece holding station or processing location) ability with a common focal point but divergent optical axes. Binocular vision is beneficial for automatic feature recognition (such as workpiece spatial position, barcode, fiducial, etc.) and end effector/workpiece positioning, and enable a virtual reality mode where the separate images can be viewed by a user on a screen with three dimensional capabilities (e.g. using glasses or a headset). Multiple sensors 281 are employed to produce images similar to stereo microscope images. In one aspect the lens 282 and lens mount 283 include motorized focus and zoom control. As may be realized, the workpiece detecting member 280 is configured (along with suitable image processing in the controller 199) to provide one or more of workpiece presence/absence detection, identification of a workpiece, alignment of the gripper 101G relative to a workpiece at a workpiece holding location, positioning of a workpiece held by the gripper relative to a workpiece holding location or processing location, imaging of the workpiece for alignment of the workpiece using the pre-alignment stage 103 or any other suitable identification and/or position related information pertaining to the workpiece, the gripper and/or any suitable workpiece holding location.

As may be realized, in one aspect, the vision system includes one or more sensors CAM1-CAM5 that are mounted off of the end effector and/or housing for viewing workpiece 400 pick and place locations or any other suitable location within the automated transport and positioning system 100. In one aspect the off end effector sensors CAM1-CAM5 are employed where the end effector 101 does not include sensor 281 or where the sensor 281 on the end effector 101 is not used, while in other aspects, the off end effector sensors CAM1-CAM5 are employed in conjunction with the end effector sensor 281. As noted above, in one aspect information obtained from the vision system (including the one or more sensors mounted off of and/or on the end effector) allow for tracking of the workpieces and specimens thereon through the database DS (which in one aspect is part of a laboratory information management system LIMS). For example, in one aspect one or more sensors CAM1 are mounted to the frame 140F in any suitable manner for imaging a transfer of cassettes 102 to and from the magazine 105 by, for example, the cassette shuttle 126. In another aspect, one or more sensors CAM2 are mounted to the frame for imaging a transfer of workpieces 400 by the end effector 101 (in addition to or in lieu of the workpiece detecting member 280 described above) to and from a cassette 102 located at the predetermined pick/place position or workpiece holding station 176. In still another aspect one or more sensors CAM3 are mounted to the frame 140F at any suitable location for viewing picking and placing workpieces to and from the pre-aligner stage 103. In one aspect the one or more sensors CAM3 are mounted to the pre-aligner stage 103 and/or the cassette shuttle so as to move in the Z direction with the pre-aligner stage 103 while in other aspects the one or more sensors CAM3 are stationary relative to the frame 140F. In one aspect the one or more sensors CAM4 are mounted within the load lock 120 for imaging a magazine 105 and/or cassette 102 disposed therein. In one aspect the one or more sensors CAM5 are mounted within the process module PM for aligning a workpiece 400 with, for example, the electron beam of the process module. As may be realized, in one aspect a common camera, such as camera CAM2 is placed and configured for viewing picking and placing of workpieces from multiple areas such as, for example, from the cassette 102 and at the pre-aligner stage 103. In other aspects a common camera is placed and configured for viewing the gripping of the cassettes by the cassette shuttle 126, the transfer of workpieces 400 to and from the cassettes 120 at workpiece holding station 176 and the transfer of workpieces 400 to and from the pre-aligner stage 103. The one or more sensors CAM1, CAM2, CAM3, CAM4 are substantially similar to sensor 281 described above and in one aspect, the one or more sensors CAM1, CAM2, CAM3, CAM4 are monocular cameras while in other aspects the one or more sensors CAM1, CAM2, CAM3, CAM4 are stereo cameras. It is noted that the stereo cameras described herein include two or more lenses with a separate image sensor for film frame for each lens allowing the camera to simulate human binocular vision for capturing three dimensional images (e.g. stereo photography). In one aspect the controller 199 is configured to determine a range or distance, based on one or more three dimensional images from the stereo cameras, between the grippers described herein (such as the end effector 101 and gripper of the cassette shuttle 126) and the workpiece 400 or cassette 102 gripped thereby when picking and placing the workpiece(s) 400 and/or cassette(s) 102 to and from respective holding areas (e.g. the magazine 105, cassette 102, pre-aligner 103 or any other suitable workpiece or cassette holding area). In other aspects, the range or distance between the between the grippers described herein and the workpiece 400 or cassette 102 gripped thereby is determined in any suitable manner.

Figure 2L:
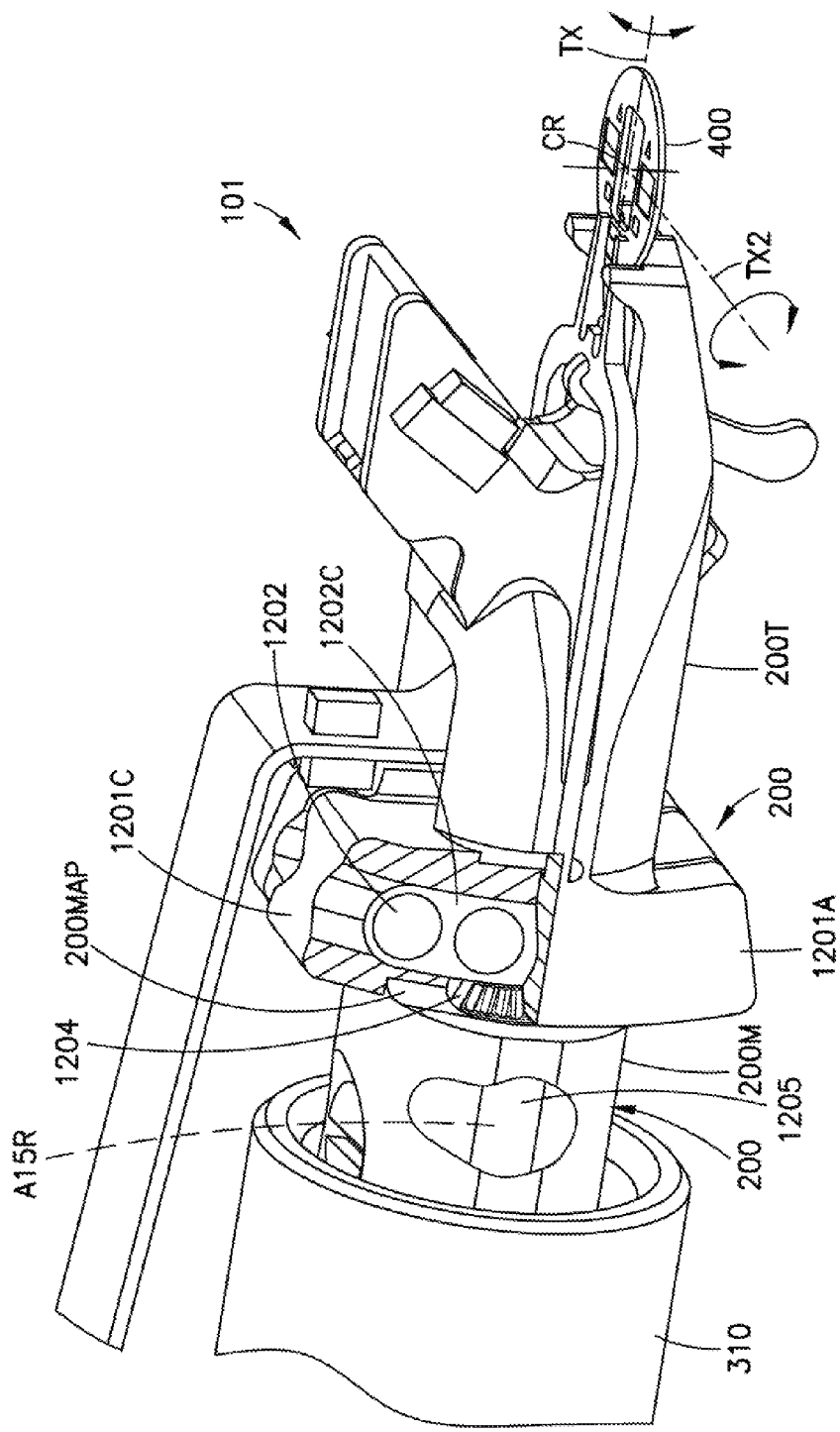
Figure 3C:
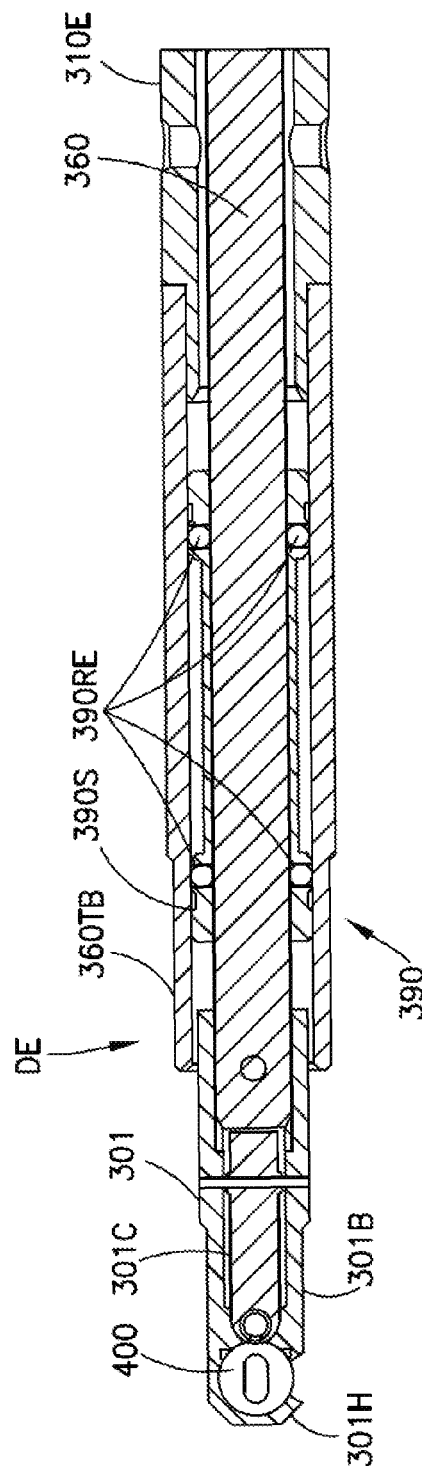
Figure 3D:
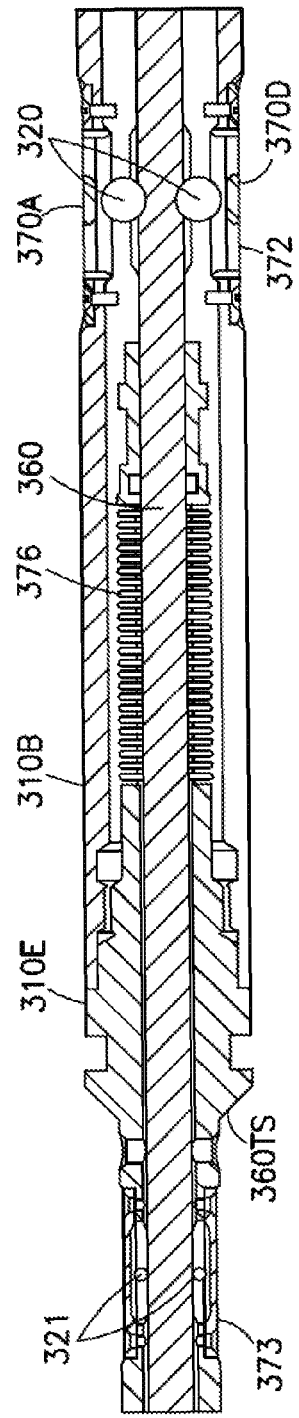
Figure 3E:
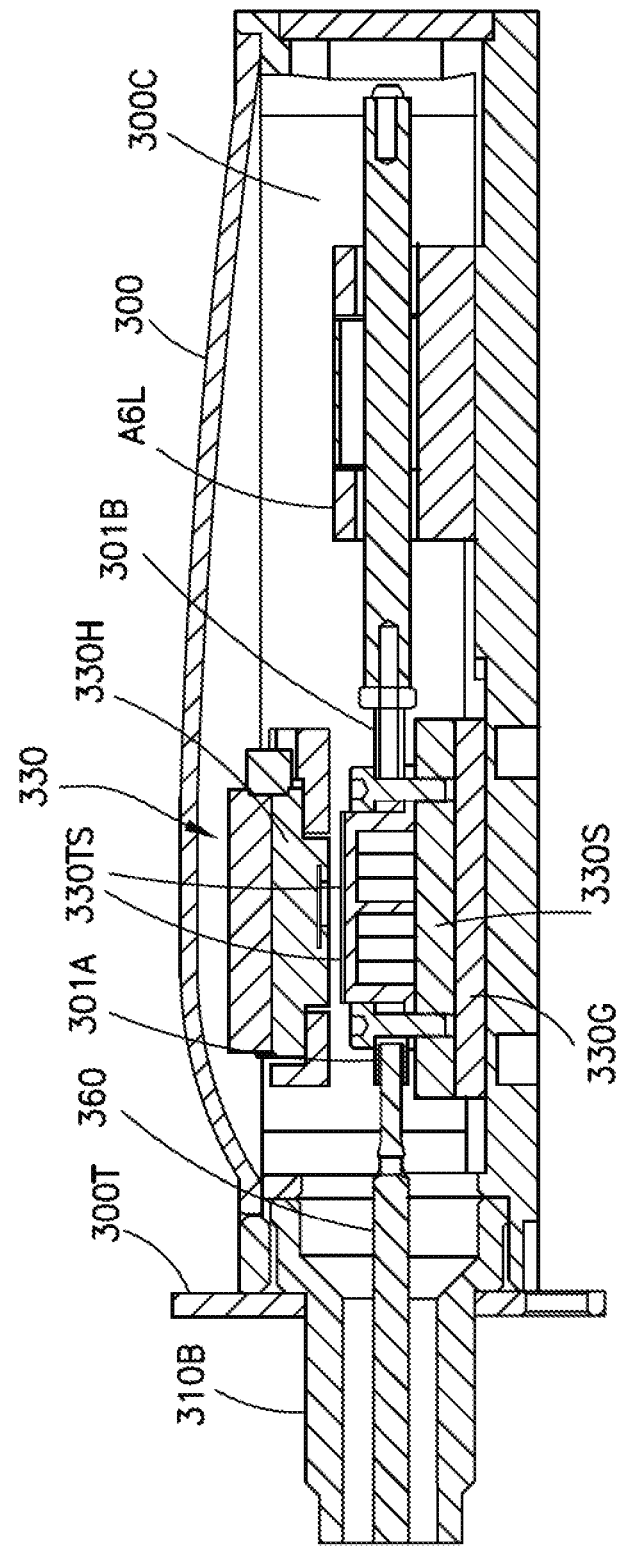

Referring to FIGS. 2J-2L, the workpiece positioning unit 104 and the end effector 101 are configured so that the end effector rotates about axis TX (FIG. 2A) and at least a portion of the end effector 101 rotates about axis TX2 (FIG. 2J—e.g. the beta tilt axis). In this aspect end effector 101 is substantially similar to that described above except where noted. For example, the body 200 is divided into a base portion 200M and a tilting portion 200T where the base portion 200M is configured to engage the connecting member 260 so that as the connecting member 260 is rotated by tilt axis drive A7R the end effector 101 rotates with the connecting member. The tilt portion 200T is movably mounted to the base portion 200M by any suitable bearing, such as bearing 1200, so that the tilt portion 200T rotates about axis TX2 which is coincident with a center of rotation CR of the workpiece 400 when the workpiece 400 is held by the end effector. In one aspect the bearing 1200 is integrally formed as a monolithic unit with the base portion 200M while in other aspects the bearing 1200 and base portion 200M are joined in any suitable manner. The bearing 1200 includes an inner race 1201C and at least one outer race 1201A, 1201B where any suitable ball bearings 1202 (held within a cage 1202C) are disposed between the inner race 1201C and each of the outer races 1201A, 1201B. The ball bearings 1202 are constructed of any suitable material such as ceramic. As may be realized, the inner race 1201C and the outer race(s) 1201A, 1201B of the bearing 1200 have a suitable arced configuration to provide a goniometer movement where the tilt portion 200T moves in the direction of arrow 1210 about axis TX2 by any suitable amount such as, for example, ±10° relative to axis TX. In other aspects the tilt portion is movable in the direction of arrow 1210 by an amount more or less than ±10°.

As can be seen in FIGS. 2K and 2L at least one of the outer races 1201A, 1201B includes a gear rack 1203 configured to engage at least one gear 1204 disposed at least partly within one or more of the base member 200M and the connecting member 260. In one aspect a single gear 1204 is provided to engage the gear rack 1203 of a single outer race 1201A, 1201B. In one aspect the gear 1204 is any suitable gear, such as a pinion gear, that is mounted to, or otherwise coupled to, a drive shaft 1205 that extends at least partially through the connecting member 260 to engage tilt axis drive A15R. The tilt axis drive A15R is disposed at any suitable location within the housing 104H for driving the drive shaft 1205. In one aspect the configuration of the tilt axis drive A15R and the drive shaft 1205 is substantially similar to the configuration of tilt axis drive A7R and the connecting member 260 such that the tilt axis drive A15R rotates the drive shaft 1205 about axis TX. As may be realized, the drive shaft 1205 includes any suitable dampers (substantially similar to that described with respect to connecting member 260) to decrease settling times of the end effector. As may be realized, the gear 1204 is coupled to the drive shaft 1205 so as to rotate with the drive shaft 1205. The base member 200M includes an aperture 200MAP through which the gear 1205 and the gear rack 1203 engage each other such that as the gear 1205 is rotated the tilt portion 200T of the end effector 101 (and the workpiece 400 held thereby) rotates in the direction of arrow 1210 about axis TX2 (e.g. the center of rotation CR of the workpiece 400).

Referring now to FIGS. 1B and 3A-3E a workpiece positioning unit 304 is provided, in accordance with aspects of the disclosed embodiment, where the workpiece positioning unit 304 is configured to interface with, for example, a drive/positioning stage or any other suitable unit 181 of, for example, a TEM (or in other aspects a SEM, DB-FIB, STEM or other suitable electron beam microscopy device) that provides substantially all necessary degrees of freedom to position a workpiece within the TEM. A suitable example of a positioning stage 181 of a TEM is the CompuStage™ manufactured by FEI. In this aspect the workpiece positioning unit 304 includes the axis drive A6L (e.g. "fast axis") configured to move the end effector along the Y axis for providing increased move speeds and decreased settle times along the long axis (e.g. in the examples shown herein along the Y axis) of the workpiece positioning unit compared to the move speeds and settle times provided by the positioning stage 181. As noted above, positioning the workpiece within the processing module PM using the drive A6L provides maximized throughput when stepping across the workpiece to take a "column" of images (e.g. a series of images taken at different points along the Y axis of the workpiece) such as during TEM imaging.

In one aspect, the positioning unit 304 includes a housing or frame 300, a tube member 310 extending from the housing 300, a connecting member 360 extending through the tube member, a linear drive A6L (described above) and a drive encoder 330. While the tube member 310 is illustrated as being a cylindrical tube, in other aspects the tube member has any suitable shape configured to be inserted into a mating aperture of the TEM or other suitable processing module PM. In one aspect the tube member 310 has a unitary construction while in other aspects the tube member 310 includes a base member 310B and an extension member 310E that are coupled to each other in any suitable manner (see FIG. 3D), such as through an interference fit, mechanical fasteners or chemical fasteners. The housing 300 forms a chamber 300C in which the drive A6L and encoder 330 (which includes a read head 330H and a tape scale unit 330S having one or more tape scale 330TS, e.g., one absolute and one incremental which is substantially similar to encoder 245) is mounted. The housing and/or tube member includes one or more features that interface with the positioning stage 181 for locating the end effector relative to the beam of the TEM. For example, the positioning stage 181 includes an aperture 181P through which the tube member 310 is inserted. The positioning stage 181 also includes a recess 181T and the housing includes a locating member 300T that is configured to engage the recess 181T. In one aspect the tube member 360 also includes a tip bearing surface 360TB configured to engage a corresponding bearing surface within the aperture 181P. The tube member also includes a shoulder 360TS at any suitable position along the tube member 360 that engages a corresponding shoulder within the aperture 181P. One or more of the tube member 360, tip bearing surface 360TB, shoulder 360TS and locating member 300T positions the end effector relative to the positioning stage 181 for orienting the end effector in the x, y, Z and pitch axes relative to the beam of the TEM.

In this aspect the drive A6L is coupled to the connecting member 360 through the tape scale unit 330S. For example, the tape scale unit 330S is mounted to the housing 300 through any suitable linear guide members 330G so that the one or more tape scale 330TS is linearly movable along the Y axis. The tape scale unit 330S includes couplings 301A, 301B positioned along the Y axis on opposite sides of the tape scale unit 330S such that the drive A6L is coupled to one coupling 301B and the connecting member 360 is coupled to the other coupling 301A. The connecting member 360 extends from the coupling 301A and through the tube member 310 so that the end effector 301 is disposed adjacent or extends past a distal end DE of the tube member 310 relative to the housing 300 (where the tube member is coupled to the housing at the proximate end of the tube member relative to the housing). The connecting member 360 is supported within the tube member 310 in any suitable manner such as, for example, with any suitable bearings and/or dampers. In one aspect the tube member 310 includes one or more damper access ports 370A-370D, 371A-371D for installing or otherwise servicing a respective damper 320, 321. The damper access ports include covers 372, 373 configured to seal respective damper access ports 370A-370D, 371A-371D to, for example, isolate an interior of the tube member 310 from an external environment. In one aspect the dampers 320, 321 are constructed of any suitable elastomer (or any other suitable material) and are configured to allow the connecting member 360 to move linearly within tube member 310 and/or allow the connecting member to spin or tilt (e.g. about the tilt axis TX shown in FIG. 2A) within the tube member 310. For example, the dampers 372, 373 are in the form of a ball or have any other suitable shape and/or configuration. The dampers 372, 373 are placed at any suitable position along the length of the tube member 310 for dampening vibrations of the connecting member 360 and/or end effector 301 to decrease settling times. For example, the dampers decrease or substantially eliminate vibrations of the connecting member 360 induced by the drive A6L during movement of the end effector/connecting member. In one aspect the dampers provide for 8-24 micron moves of the end effector where substantially all vibrations are damped or settled to less than about 4 nm to about 5 nm in less than 50 ms or in other aspects settled to less than about 4 nm to about 5 nm in less than about 25 ms to about 35 ms. In other aspects the dampers provide for any suitable length move and any suitable settling times. The connecting member 360 is also supported within the tube member 310 adjacent the distal end DE of the tube member 310 by a bearing 390. The bearing 390 is configured to provide rigid lateral support for the connecting member 360 within the tube member 310 while minimizing axial friction when moving the connecting member and end effector. The bearing 390 includes a bearing sleeve 390S circumferentially surrounding the connecting member 360. The sleeve forms one or more separators or cages 390R that position any suitable rolling elements 390RE, such as ball bearings, a predetermined distance Y2 from each other. The distance Y2 is any suitable distance that provides stiffness to the connecting member 360 and/or dampen vibration of the connecting member 360 and/or end effector 301 to decrease settling times. The separators 390R are configured to circumferentially position the rolling elements 390RE circumferentially around the connecting member 360 as can be seen in FIG. 3B. It is also noted that the inner and outer races of the bearing 390 are formed by the connecting member 360 (e.g. the inner race) and the inner surface of the tube member 310 (e.g. the outer race) such that the rolling elements 390RE substantially directly contact the connecting member 360 and inner wall of the tube member 310. In one aspect a small interference fit (e.g. in one aspect about 2 microns and in other aspects more or less than 2 microns) exists between the rolling elements 390RE and the connecting member 360/tube member 310. The rolling elements 390RE are constructed of any suitable material such as, for example, ceramic, metal, composites, etc.

In one aspect any suitable seals are located within the tube member 310 for sealing or otherwise isolating the drive A6L and the chamber 300C of the housing 300 from an environment in which the end effector is located (e.g. to isolate the work holding region of the positioning unit from atmospheric pressure outside the processing module). For example, any suitable bellows seal 376 is provided at any suitable location within the tube member 310 for sealing or otherwise isolating the chamber 300C so that the pumped volume (e.g. the column within the tube member that is exposed to a vacuum or other predetermined environment) is minimized. In one aspect the bellows seal 376 is longitudinally (e.g. along the long axis of the connecting member) located between the dampers 372, 373. In another aspect, the tube member 310, as noted above, is formed of individual pieces coupled together such that the bellows seal 376 is located at or adjacent a union or coupling of the pieces (e.g. such as adjacent the location where the base member 310B is coupled to the extension member 310E to allow for easy installation of the bellows seal 376.

The end effector 301 is coupled to the connecting member 360 in any suitable manner such as, for example, in a manner substantially similar to that described above with respect to end effector 101. In this aspect the end effector 301 is a manually actuated end effector while in other aspects the end effector is substantially similar to that described above. In this aspect, the end effector includes a body 301B that is configured to engage the connecting member 360 (e.g. in a manner substantially similar to that described above), a workpiece holding portion 301H extending from the body and a clamp member 301C. The clamp member 301C is a spring clamp (that is e.g. biased in a closed position) or any other suitable clamp that is manually opened and closed. In other aspects the clamp member is opened and closed in any suitable manner for gripping a workpiece 400. In other aspects the workpiece detecting member 280 described above is mounted to the end effector 301 in a manner substantially similar to that described above.

Referring now to FIGS. 4A-4D the workpiece 400 is illustrated. The workpiece 400 is any suitable workpiece and is illustrated as a TEM grid specimen holder for exemplary purposes only. In one aspect the workpiece is substantially similar to that described in U.S. Provisional Patent application No. 61/902,470 filed on Nov. 11, 2013 and United States patent application Ser. No. 14/538,332 entitled "Specimen Sample Holder for Workpiece Transport Apparatus" filed on Nov. 11, 2014, the disclosures of which are incorporated herein by reference in their entireties. In one aspect the workpiece 400 has a disc configuration but in other aspects the workpiece has any other suitable shape. In one aspect, the workpiece 400 has a single one piece construction (e.g. is formed as a monolithic member) while in other aspects, the workpiece has a multi-piece construction as described in United States patent application Ser. No. 14/538,332 entitled "Specimen Sample Holder for Workpiece Transport Apparatus" filed on Nov. 11, 2014 the disclosure of which is incorporated herein by reference in its entirety. In one aspect the workpiece 400 includes a thin sheet base member BM with a first surface 400T and an opposing second surface 400B, the first surface defining a seat and support surface for a specimen holding film held by the workpiece 400. In one aspect the base member BM is constructed of a beryllium copper alloy while in other aspects the base member is constructed of any suitable material. In still other aspects the base member BM is a sub-millimeter thick sheet while in other aspects the base member BM has any suitable thickness.

The base member BM includes an aperture or slot 401 (which will be described in greater detail below) through the second surface 400B exposing the holding film held by the sample/specimen holder, and including a grip engagement zone GZ defined at least on part of the first surface 400T and arranged to accept engagement of the gripper of the end effector 101, 301. In one aspect the grip engagement zone GZ of the base member BM for the gripper is a 360 degree radial area adjacent or at a peripheral edge of the base member BM. In other aspects, the base member BM includes a recess 400R on, for example, the second surface 400B (e.g. opposite surface 400T) to provide a gripping surface so that the workpiece 400 is gripped manually, with automation, or in any other suitable manner. As will be described in greater detail below at least one of the first or second surface 400T, 400B includes machine readable structures formed thereon arranged in patterns embodying data that is a physical representation of a specimen or sample held on a respective workpiece where the physical representation of the specimen or sample, in one aspect, defines at least one predetermined characteristic of the sample holder as will be described in greater detail below. As will also be described below, the predetermined characteristic may be a unique identification indicia of the sample and/or sample holder, with error correction characteristics.

As described above, the workpiece 400 includes a slot 401 in which a specimen is held. In one aspect the slot 401 may have any suitable predetermined length L and any suitable width W1, W2, W3 (while three widths are illustrated in other aspects the workpiece 400 may be provided with a slot having any suitable width and/or length or an aperture having any suitable geometric shape). In this aspect the slot is an open slot but in other aspects the slot includes a mesh or other suitable geometry for holding one or more specimens. In still other aspects the workpiece may not include a slot. In one aspect the corner of the slot 401C is be rounded to, for example, provide more imageable area to rectangular specimen samples.

In one aspect, as noted above, the workpiece 400 includes one or more suitable structures or identifying indicia that define three dimensional topography with respect to a reference plane of the at least one first or second surface 400T, 400B on which the structures are disposed and wherein the structures are formed integral with the at least one first or second surface 400T, 400B on which the structures are disposed. In one aspect the structures are disposed symmetrically on at least the first or second surface 400T, 400B providing redundant reading locations while in other aspects the structures have any suitable arrangement relative to each other and/or the first or second surface 400T, 400B. In one aspect the structures are identifiers, such as two dimensional datamatrix barcodes 402A, 402B that may be formed on a first surface 400T (e.g. from which the specimens are viewed) of the workpiece 400 in any suitable manner and at any suitable locations. In one aspect the barcodes 402A, 402B are engraved or micro-machined on the surface on opposite sides of the slot 401. In one aspect each barcode may be a one dimensional or two dimensional barcode that includes at least 14 cells along a length of the barcode (e.g. for 1-D a barcode) or at least one side of the barcode (e.g. for a 2-D barcode). For example, in one aspect, the barcode may be a 14×14 datamatrix that has the capacity to encode $3.6 \times 10^{15}$ unique 10-character alphanumeric serial numbers (which, in one aspect, are used in a manner similar to and/or embody accession numbering where the accession numbering corresponds to specimen samples that are registered in, for example, data structure DS and/or the laboratory information management system LIMS such that the accession numbering defines an ordered sequence of the workpieces 400 holding the specimen samples) with error correction to uniquely identify a specimen as described herein in for example the laboratory information management system LIMS or other any suitable database or tracking system. In other aspects the barcodes 402A, 402B have any suitable size and are configured to provide any suitable serial numbers or other information such as alphanumeric serial numbers having more or less than 10 characters. The barcodes 402A, 402B are used in conjunction with other identifiers on, for example, the cassettes 102 and/or magazines 105, to identify which magazine and/or cassette the sample is located. Multiple barcodes 402A, 402B are provided to provide redundancy in the event one barcode is obscured or damaged and allow the barcodes to be read from many viewing angles. The structures also define a human readable identifier 403 on the first or second surface 400T, 400B to allow an operator to manually read the identifier 403 and to identify (e.g. without a barcode reader) the specimen(s) located on the workpiece 400. In one aspect the identifier 403 may be a 10-character alphanumeric serial number (e.g. that matches or otherwise corresponds to the serial number (s) of the barcode).

In one aspect the structures define one or more machine readable fiducial 404A-404D relating a specimen position to end effector gripper or holder position. In one aspect the at least one fiducial 404A-404D includes more than one unique fiducial, each of which independently identifies the relative position of the specimen to the holder. The fiducials 404A-404D are also provided in any suitable manner, such as by etching, engraving or micro-machining, on the first surface 400T. These fiducials 404A-404D may provide an absolute physical reference between the specimen mounted to the workpiece and the workpiece physical boundaries (e.g. the edges of the slot 401 and/or the peripheral edge of the workpiece). In one aspect the workpiece detecting member 280 (along with any suitable image processing performed by, for example, controller 199) is configured to read or otherwise detect the fiducials 404A-404D for aligning the end effector with the workpiece for picking the workpiece, aligning the workpiece held by the end effector 101 with a workpiece holding station for placing the workpiece, for rotating the workpiece during alignment on the pre-aligner stage 103, for aligning the workpiece with a beam of the TEM and/or for any other suitable purpose. As may be realized the barcodes and fiducials provide for automated, high-throughput machine-based recognition and handling of the workpieces for substantially unassisted specimen loading, positioning, verification, quality control, and handling for high-throughput and controlled environment applications.

In one aspect the structures provide tailored optical properties of the first and/or second surface 400T, 400B. For example, in one aspect, the structures define retro-reflection features providing a predetermined optical response. In one aspect any suitable number (such as, e.g., hundreds, and even thousands) of miniature tuned "corner cube" and/or "cat's eye" retroflecting features are etched, engraved or otherwise micro-machined into the surface of the workpiece 400 to provide optimal optical response (contrast, and possibly even wavelength filtering) at the macro level.

As may also be realized, the slot 401 is suitably positioned away from the gripping zone GZ and/or recess 400R so that the gripper of the end effector 101, 301 does not contact or obstruct the specimen. It is noted that, in one aspect, the workpiece 400 may not include the recess in the gripping zone GZ of the workpiece 400. It is noted that the slot 401 has any suitable orientation relative to the recess 400R/gripping zone GZ as illustrated in FIGS. 4C and 4D.

Referring to FIGS. 5A-5I the cassette 102 is illustrated in accordance with aspects of the disclosed embodiment. In this aspect the cassette 102 is illustrated as having a rectangular shape cassette frame 102F but in other aspects the cassette 102/cassette frame 102F has any other suitable shape and/or configuration. The cassette frame 102F includes one or more workpiece 400 holding stations or pockets 500 arranged in a grid such that the pockets are accessible from a first side 102T of the cassette 102. In this aspect the grid includes and 8×8 array of pockets 500 for holding 64 individual workpieces 400 but in other aspects the grid has any suitable number of columns and rows such as for example, an 8×16 array for holding 128 individual workpieces. In one aspect the cassette also includes column and row identifiers (e.g. such as alphanumeric characters, barcodes, etc.) on the first side 102T (or at any other suitable location) for allowing operator and/or machine identification of a location of each pocket 500. For example, the columns are identified by a sequential series of numbers 1-8 and the rows are identified by a sequential series of letters A-H (or vice versa) however, in other aspects any suitable identifiers may be used. The cassette 102 also includes any suitable machine readable and/or human readable indicia for identifying the cassette. For example, the cassette has a longitudinal axis LA1 and a lateral axis LA2 so as to define lateral sides SL1, SL2 and longitudinal sides SL3, SL4. In one aspect the first side 102T (from which the workpieces are accessed) includes any suitable number of barcodes 501A and human readable indicia 502A (such as serial numbers) which, in one aspect, is substantially similar to those described above with respect to workpiece 400. As may be realized, in one aspect, other surfaces such as longitudinal surface or side SL4 also include similar barcodes 502B and human readable indicia 502B so that the cassette 102 is identified or identifiable while located within, for example a magazine 105.

As may be realized, in one aspect, workpieces are arranged or otherwise placed within respective pockets 500 of a cassette 102 in an ordered sequence, where the ordered sequence is based on, for example, the identifying indicia described above. In one aspect the ordered sequence corresponds to a workpiece or specimen processing order where more than one workpiece or specimen is processed in a batch of workpieces or specimens. As may also be realized, in one aspect, the ordered sequence of workpieces or specimens spans more than one cassette 102 such as when one or more cassettes 102 are held within a magazine 105 and the batch of specimens or workpieces to be processed includes one or more of the cassettes 102 in the magazine 105 (e.g. the magazine 105 holds one or more batches where the batches are identified by one or more of a workpiece identifying indicia and a cassette identifying indicia). In one aspect, the batches (e.g. the workpieces/specimens and/or cassettes included in the batches) are defined in the data structure DS by the workpiece identifying indicia and/or cassette identifying indicia (e.g. the batch to which a workpiece/specimen belongs is included in the identifying indicia of a respective workpiece/specimen).

In one aspect, the pockets 500 of the cassette 102 are configured with tapered sides or guide members 500T. In one aspect the sides 500T direct the workpieces 400 into a holding slot 500S. In other aspects the tapered sides or guide members 500T are configured to allow gripper access into the holding locations for gripping the workpieces 400 (see FIG. 5I) and to allow viewing of the workpieces within the slots 500S with the workpiece detecting member 280. As may be realized, in one aspect, also referring to FIGS. 5D and 5J the pockets 500 include any suitable workpiece retaining features or structures 500R that are separate and distinct from or integral with one or more of the holding slot 500S and/or sides 500T of the pocket 500. The workpiece retaining features 500R may be configured to substantially prevent the workpieces from falling out of a respective pocket 500 due to, for example, accelerations, gravity or impacts while allowing (e.g. the retaining features 500R do not inhibit) extraction and insertion of the workpiece from and to the pocket 500 by the end effector 101, 301. Examples of workpiece retaining features 500R include, but are not limited to, grip tape, pressure sensitive adhesive, sheet adhesives, dispensed liquid adhesives (that dry or cure to form the retaining features), resilient members, electrostatic retention members, clips, or any other suitable retention member(s). As may be realized, the retaining features 500R retain the workpieces 400 in the pockets 500 up to, for example, several G's of load in any direction, while allowing the end effector 101 or manually operated tweezers to be inserted into the pocket for extracting the workpieces 400 from the respective pockets 500 without any residue being left on the workpieces 400. As may also be realized, the workpiece retaining features 500R are configured to maintain a rotational position/orientation of the workpiece 400 while the workpiece is disposed within the pocket 500. For example, if the workpiece is inserted into the pocket with a predetermined rotational orientation (such as after being aligned with any suitable aligner (which in one aspect is external to the process module PM and/or automated transport and positioning system 100) that rotational orientation is maintained within the process module PM and/or automated transport and positioning system 100 so that the alignment of the workpiece 400 with the pre-aligner 103 may be skipped resulting in increased throughput in the process module PM. In other aspects, where the workpiece 400 is aligned with the pre-aligner 103 that rotational orientation is maintained within the pocket 500 by the workpiece retaining features 500R during transport of the workpiece within the cassette 102. In one aspect the workpiece retaining features 500R are high-vacuum compatible where a high vacuum is, for example, $10^{-5}$ Torr or below. As may be realized, the cassette 102 may include any suitable kinematic locating features on one or more surfaces of the cassette 102 to allow relative positioning (e.g. alignment) between the pockets 500 (and workpieces therein) and the gripper of the end effector 101. For example, the first surface or side 102T includes one or more kinematic recesses 510 (or other suitable features) and a second surface or side 102B includes one or more recesses 511 (e.g. located at or adjacent one or more of the longitudinal sides SL3, SL4) that interface with the gripper 126G of the cassette shuttle 126 (FIG. 1D) for automated picking and placing the cassette 102 from and to the magazine 105. In one aspect the cassette 102 also includes recesses 515 on, for example, the lateral sides SL1, SL2 for allowing manual removal and insertion of the cassette 102 from and to the magazine 105. In other aspects the gripping features 515, 510, 511 are located at any suitable location of the cassette 102. In one aspect the lateral sides SL1, SL2 of the cassette 102 are also configured in any suitable manner to interface with the magazine 105, as will be described below, so that the cassette is inserted into the magazine 105 in a predetermined orientation. In one aspect, the lateral sides SL1, SL2 are tapered for engaging tapered surfaces 600T of the magazine 105 (FIG. 6A-6E) so that the cassette can only be inserted into the magazine 105 in a single orientation. In other aspects the cassette 102 engages the cover 590 (described below) where the cover 590 in turn engages the magazine such that both the cover and cassette have a nested "poka-yoke" or position determining features that provide for the insertion of the cassette/cover assembly into the magazine in the predetermined orientation. In one aspect a recess 520 is located on the second side 102B of the cassette 102 and includes any suitable wireless identification, such as RFID chips or other wireless identification, transponder, or telemetry unit. In other aspects the wireless identification is attached to the cassette at any suitable location and in any suitable manner.

Figure 5C:
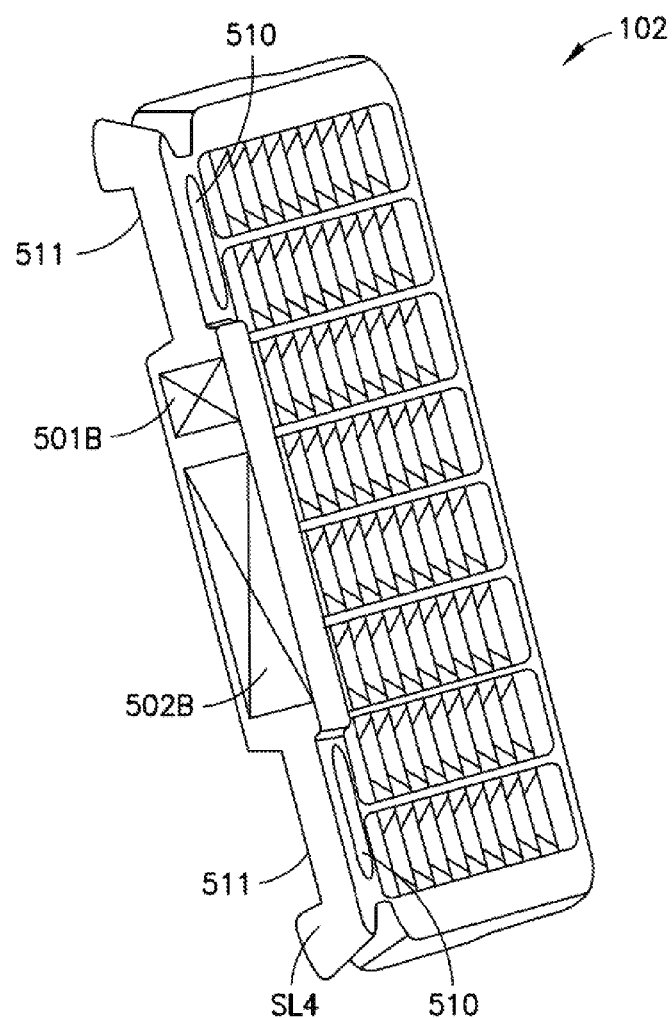
Figure 5D:
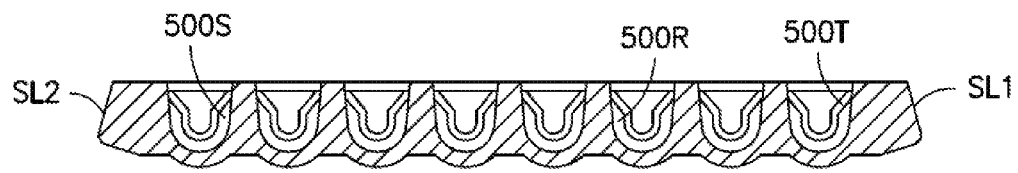
Figure 5H:
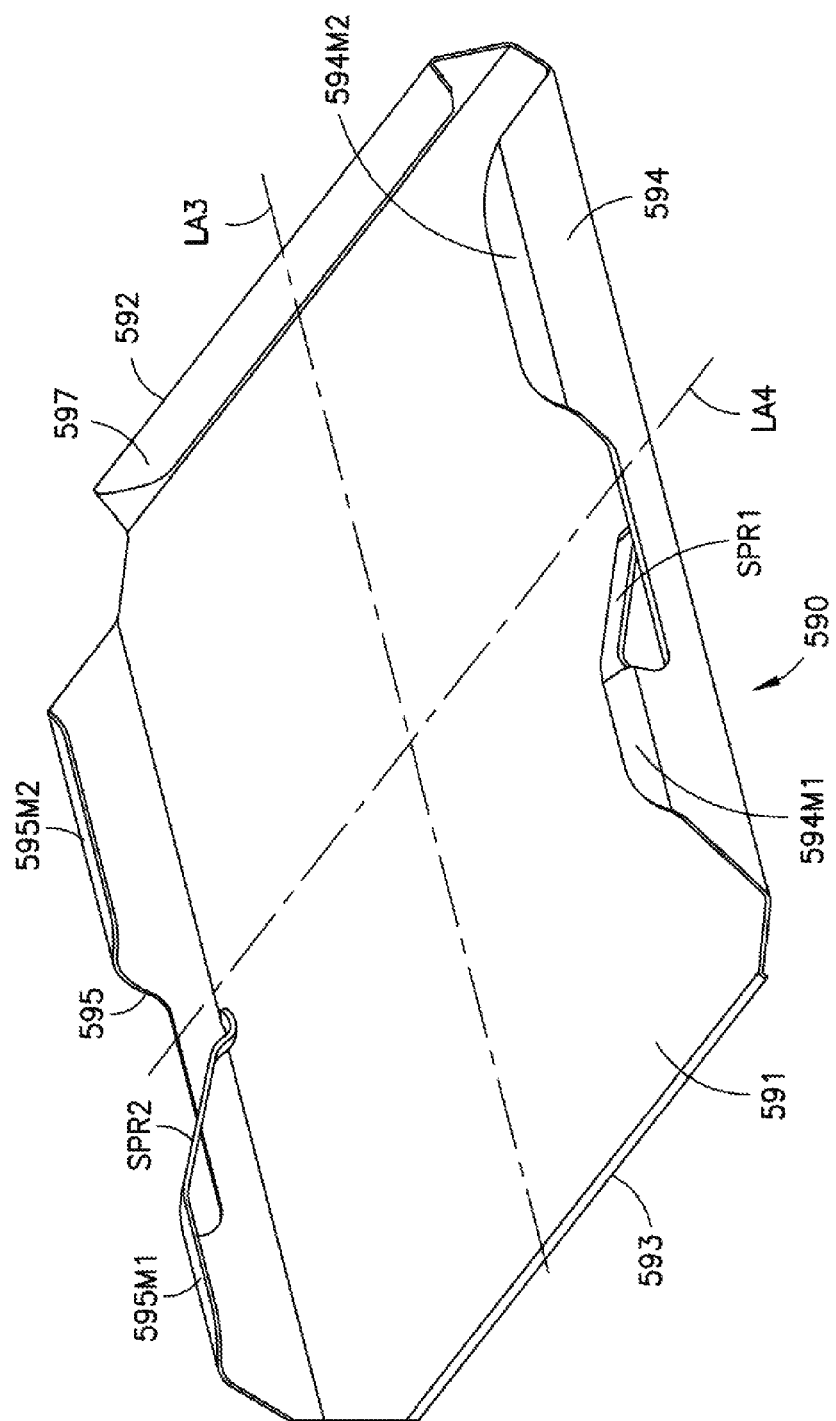
FIG. 5H is a schematic illustration of a portion of the specimen positioning system of FIGS. 2A-2L and the specimen cassette of FIGS. 5A-5G, 5I and 5J in accordance with aspects of the disclosed embodiment.
Figure 6F:
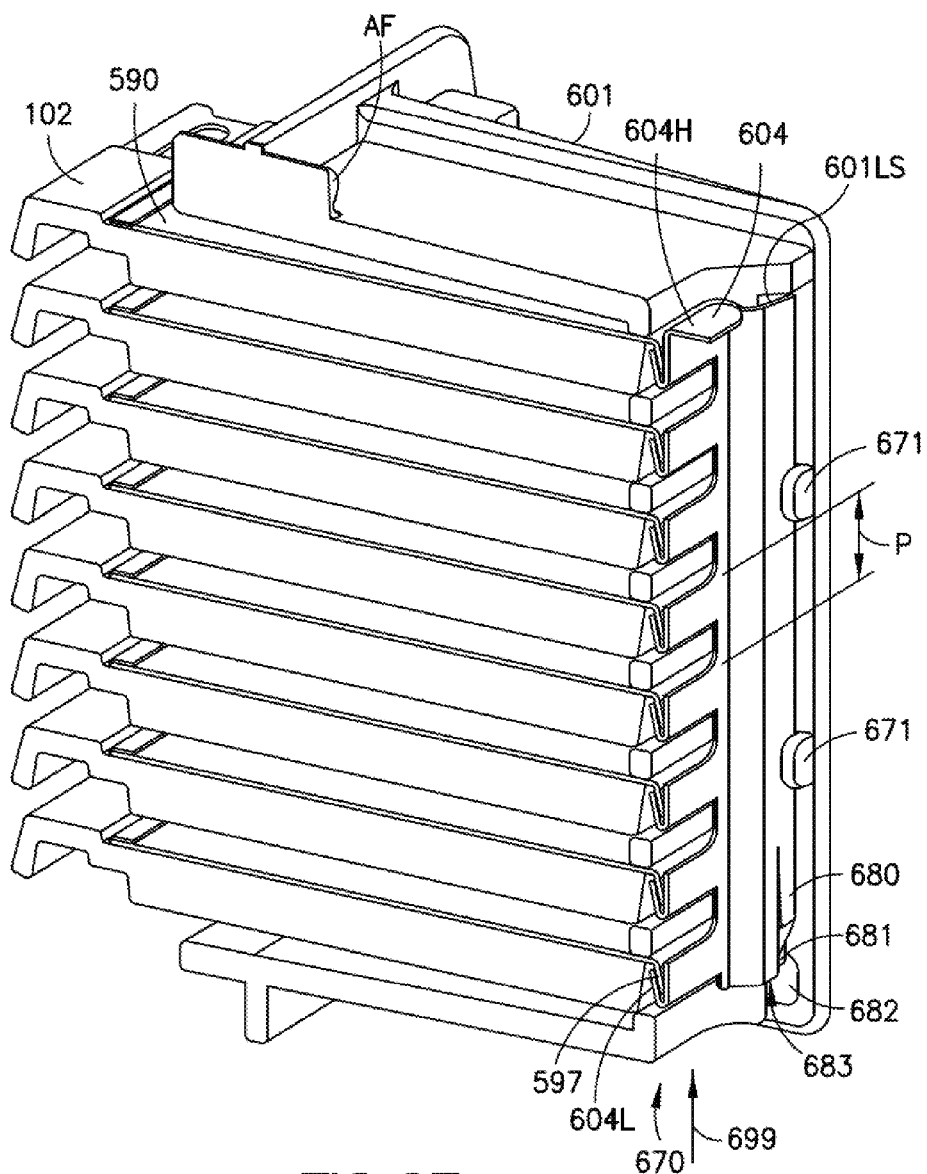

Referring also to FIGS. 5H and 5G the cassette 102, in one aspect, includes a detachable cover 590 for securing or otherwise retaining the workpieces 400 inside the pockets 500 during, for example, transport and/or storage of the cassette 102. The cover 590 has a longitudinal axis LA3 and a lateral axis LA4 so as to define longitudinal sides 592, 593 and lateral sides 594, 595. At least one longitudinal side 593 of the cover 590 may be open to allow the cover 590 to slide over the cassette 102. For example, side 593 of cover is slid over the cassette 102 by moving the cover 590 from longitudinal side SL3 of the cassette 102 towards longitudinal side SL4 of the cassette as can be seen in FIG. 5G so that retaining surface 591 of the cover 590 is disposed adjacent to and spans the first side 102T of the cassette 102 for retaining the workpieces in their respective pockets 500. As may be realized the lateral sides 594, 595 of the cover extend or wrap around lateral sides SL1, SL2 of the cassette 102 (e.g. following the angle of the lateral sides SL1, SL2, for orienting the cassette in the magazine) so that extension members 594M1, 594M2, 595M1, 595M2 extend over a portion of the second surface 102B to substantially prevent separation of the cover 590 from the cassette 102. At least one extension member 594M1, 594M2, 595M1, 595M2 include resilient members SPR1, SPR2 that are configured to engage protuberances 537 disposed on the second side 102B of the cassette to substantially prevent relative longitudinal motion between the cassette 102 and the cover 590 and so that the cassette 102 is retained within the cover 590. It is noted that the retention force of the resilient member SPR1, SPR2 is such that it holds the cassette within the cover while allowing the cassette shuttle 126 to remove and insert the cassette 102 from the cover 590 and hence the magazine 105 as described herein. The cover 590 also includes a locking member 597 at one of the longitudinal sides 592 for holding the cassette 102 and cover 590 assembly within the magazine 105 and to retain the cover 590 within the magazine 105 when the cassette shuttle 126 removes the cassette 102 from the magazine 105.

Referring to FIGS. 6A-6F a magazine 105 is illustrated in accordance with aspects of the disclosed embodiment. The magazine 105, together with one or more cassettes 102 forms a workpiece 400 storage system that is configured for manual or automated transfer of workpieces 400 to and from the pockets 500 of the cassettes 102 as described herein. The magazine 105 is configured to store at least one cassette 102, such as for example, 8 cassettes to allow for a workpiece holding capacity of 1,024 workpieces in a magazine where the cassette includes an 8×16 array of pockets. In other aspects the magazine holds more or less than 8 cassettes and has any suitable workpiece holding capacity in combination with the cassette(s). The magazine 105 includes a frame 601 that contains and supports the cassettes 102 as a unitary assembly. In one aspect the frame forms a cavity configured to be sealed with a door or cover and into which the cassettes are inserted for storage in any suitable environment of the cavity (such as for example, a vacuum environment, atmospheric environment, etc.). In other aspects the frame may not have a sealable cavity. The frame 601 includes any suitable kinematic features 610-612 (and/or automated handling features AF positioned in a known relationship with the kinematic features 610-612) that interface with corresponding kinematic features of the transport shuttle 120MS, as described above, for locating the magazine relative to the transport shuttle 120MS and/or for the automated loading of the magazine into, for example, the chamber 120C using any suitable automated magazine transport. In one aspect the kinematic features are pins and recesses but in other aspects the kinematic features are any suitable locating features. In one aspect the kinematic features 610-612 are also configured so that the magazine 105, when loaded on the transport shuttle 120MS has only a single predetermined orientation. In one aspect the frame 601 includes any suitable identifying indicia 620, that is/are substantially similar to the barcodes, human readable indicia, RFID, transponder and telemetry devices describe above, for the manual or automated identification of the magazine 105.

As described above, the magazine 105 includes one or more cassette holding stations 600. Each cassette holding station 600 includes sides 600T that conform to the cross section of the cassette and cover assembly so that the cassette and cover assembly can be inserted into the magazine 105 in only a single predetermined orientation. As also noted above, the cover 590 of each cassette 102 includes a locking member 597 that engages a corresponding locking feature of the magazine 105 for retaining the cover 590 (and the cassette 102) within the magazine 105. For exemplary purposes only, the frame 601 forms a track 670 into which a retaining or latch plate 604 is inserted. The track 670 is positioned on the frame 601 so that the longitudinal side 592 of the cover is positioned adjacent the track when the cover and cassette assembly is inserted into a respective cassette holding station 600. The track 670 includes one or more bearing surface 601LS and opposing retaining members 671. The one or more bearing surface 601LS and the respective retaining members 671 are spaced apart so that the retaining plate 604 can be inserted between the one or more bearing surface 601LS and the respective retaining members 671. The retaining plate 604 includes a handle 604H configured to allow sliding manipulation of the retaining plate 604 for insertion and removal of the retaining plate to and from the track 670. The retaining plate 604 also includes locking members 604L that engage the locking members 597 of the covers 590 when the retaining plate 604 is inserted into the track 670. For example, the retaining plate 604 is slid or otherwise inserted in the direction of arrow 699 into the track 670 between the one or more bearing surface 601LS and the respective retaining members 671. The locking members 601L of the retaining plate 604 face the direction of insertion 699 while the locking members 597 of the covers 590 face a direction opposite the direction of insertion 699 so that when the retaining plate 604 is fully inserted into the track (as will be described below) the locking members 597 substantially simultaneously engage the opposing locking members 601L.

In one aspect the retaining plate 604 includes one or more resilient member 680 and the frame 601 includes one or more detents 681 and cam members 682. The resilient member 680 is configured to engage the cam member 682 when moving in the direction of arrow 699 (e.g. during insertion of the retaining plate in the track) so that the resilient member 680 passes over the cam 682 to engage the detent 681 for maintaining the retaining plate 604 in a closed state (e.g. the covers are securely held by the retaining plate) when the resilient member 680 is engaged with the detent 681. The resilient member is biased towards the bearing surface 601LS so that the resilient member 680 engages the detent 681 substantially preventing removal of the retaining plate 604 from the track 670. The retaining plate 604 includes a slot or channel 683 into which a release tool (not shown) is inserted to lift the resilient member 680 over the detent 681 and cam member 682 allowing passage of the resilient member 680 over the detent 681 and cam member 682 for removing the retaining plate 604 from the track 670 and/or releasing of the covers 590 from the frame magazine 105. In one aspect the frame 601 also includes another detent 681' and cam 682' and the retaining plate 604 includes another resilient member 680' configured to substantially prevent the retaining plate 604 from moving more than one cassette pitch P when, for example, the resilient member 680 and the detent 681 are disengaged. As may be realized, the retaining plate 604 includes a slot or channel 683', similar to slot or channel 683, into which the release tool (not shown) may be inserted to lift the resilient member 680' over the detent 681' and cam member 682' allowing passage of the resilient member 680' over the detent 681' and cam member 682' for removing the retaining plate 604 where the retaining plate 604 is completely removed from the track 670.

The covers 590, cassettes 102 and magazines 105 are constructed of any suitable materials. In one aspect the covers 590, cassettes 102 and magazines 105 are constructed from a vacuum environment compatible material for use in vacuum environments. In other aspects the covers 590, cassettes 102 and magazines 105 are configured for use in any suitable environment.

Figure 8:
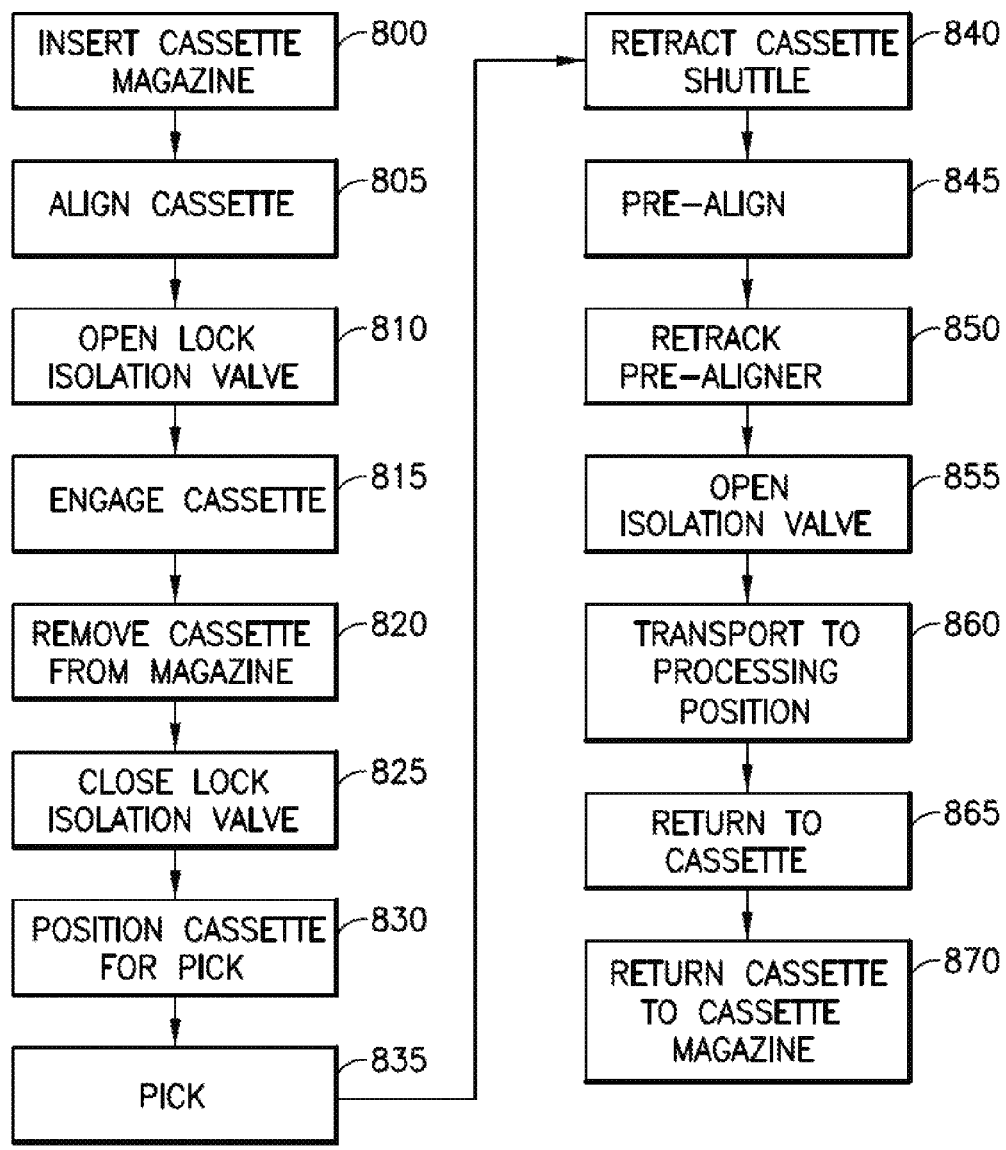
FIG. 8 is a flow diagram of an operation of the automatic specimen loading system of FIG. 1A-1D in accordance with aspects of the disclosed embodiment.

Referring now to FIGS. 1A (1A-1,1A-2) and 7A-7F an exemplary operation of the automated transport and positioning system 100 will be described in accordance with an aspect of the disclosed embodiment. The chamber 125C is pumped to a pressure substantially equal to a pressure of the process module PM and a magazine 105 holding one or more cassettes 102 is inserted into the sealable chamber 120C of the load lock 120 (FIG. 8, Block 800). For example, the door 120D is opened, and the magazine 105 is kinematically placed on the transport shuttle 120MS in any suitable manner, such as manually or with any suitable transport automation. The door 120D is closed to seal or otherwise isolate the sealable chamber 120C. The load lock is pumped to a pressure compatible with or substantially equal to the pressure within the chamber 125C and the transport shuttle 120MS is moved to align a predetermined cassette 102A over the valve V2G (FIG. 8, Block 805). The valve V2G is opened so that the interior of the chamber 120C is in communication with the interior of the chamber 125C (FIG. 8, Block 810). The cassette shuttle 126 moves in the direction of arrow 700 to kinematically engage the predetermined cassette 102A (FIG. 8, Block 815). The cassette shuttle 126 moves in the direction of arrow 701 to remove the cassette 102A from the magazine 105 (and its respective cover 590) such that a predetermined workpiece is located within a range of motion of the workpiece positioning unit 104 (FIG. 8, Block 820). As may be realized, in one aspect, the positioning of the cassette 102A (and the workpieces therein) relative to the workpiece positioning unit 104 corresponds to a predetermined batch workpiece processing sequence (defined by or in the data structure DS—see FIG. 1A) of the batch of workpieces held on one or more cassettes 102 of the magazine 105 held on the magazine shuttle 120MS. The valve V2G is closed (FIG. 8, Block 825).

The workpiece positioning unit 104 moves in one or more of the directions 703, 704, 705 (e.g. X, Y and tilt) for positioning the end effector 101 to pick a workpiece 400 from the cassette 102 (FIG. 8, Block 830) and picks the workpiece from the cassette 102 (FIG. 8, Block 835). The cassette shuttle 126 moves further in the direction of arrow 701 to move the cassette to a buffered position (FIG. 8, Block 840) and the workpiece positioning unit 104 moves in one or more of the directions 702, 704, 705 to place the workpiece on the pre-aligner stage 103 for aligning the workpiece to a predetermined orientation (FIG. 8, Block 845). As may be realized, in one aspect, data obtained by the pre-aligner stage 103 regarding the alignment of the workpiece 400 is communicated to the controller 199 in any suitable manner for inclusion in the data structure DS. In one aspect the pre-aligner stage 103 is retracted in the direction of arrow 701 such as when the pre-aligner stage is movably mounted to the frame 140F independent of the cassette shuttle 126 (FIG. 8, Block 850). In other aspects where the pre-aligner stage 103 is mounted to the cassette shuttle 126 (so that the pre-aligner stage and cassette shuttle move as a unit) the cassette shuttle may be retracted after alignment of the workpiece. In still other aspects the pre-aligner stage 103 is stationary along the Z axis and may not be retracted (e.g. the pre-aligner stage is positioned to allow workpiece positioning unit 104 access to the process module PM). The valve V1G is opened to allow access to the process module through port 125P (FIG. 8, Block 855).

The workpiece positioning unit 104 moves in one or more of the directions 703, 704, 705 (e.g. X, Y and tilt) for positioning the workpiece 400 within the process module PM for processing (FIG. 6, Block 860) while, in one aspect, being held by the end effector 101 or, in other aspects, on a positioning stage PS of the processing module PM. For example, where the workpiece 400 is processed on and positioned by (e.g. during processing) the positioning stage PS, the workpiece positioning unit 104 places the workpiece 400 on the positioning stage PS so that the positioning stage PS positions the workpiece within the processing module PM for processing. In one aspect, workpiece processing instructions are communicated to the process module (and/ or an operator of the process module) by the controller 199 from the data structure DS to effect movement of the workpiece within the process module (either, in one aspect, through movement of the end effector on which the workpiece is located or, in another aspect, through movement of the positioning stage PS on which the workpiece is located) and the processing of the workpiece 400 by the process module PM. As may be realized, the automated transport and positioning system 100 and in particular the workpiece positioning unit 104 has a workpiece/specimen picking position, outside of and sharing a common atmosphere with the objective lens chamber 8CH (described above) and the drive section of the automated transport and positioning system 100 effects movement of the end effector from the picking position (e.g. workpiece holding station 176) to, for example, the tomography inspection position (e.g. processing location 177) with multiple independent degree of freedom tomography inspection positioning of the specimen in one move.

Figure 7A:
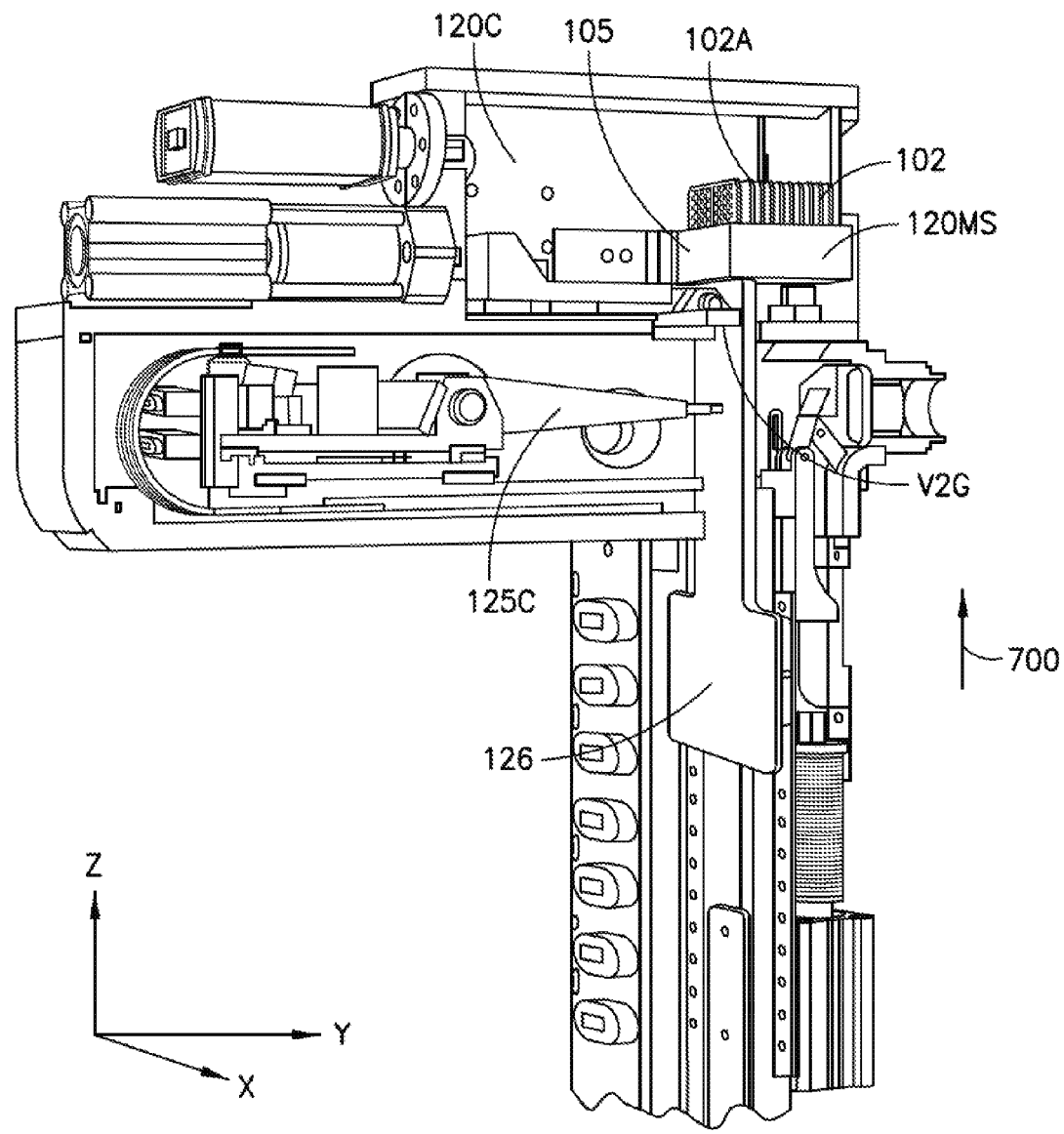
FIGS. 7A-7F are schematic illustrations showing an operation of the automatic specimen loading system of FIG. 1A (1A-1,1A-2) in accordance with aspects of the disclosed embodiment.
Figure 7B:
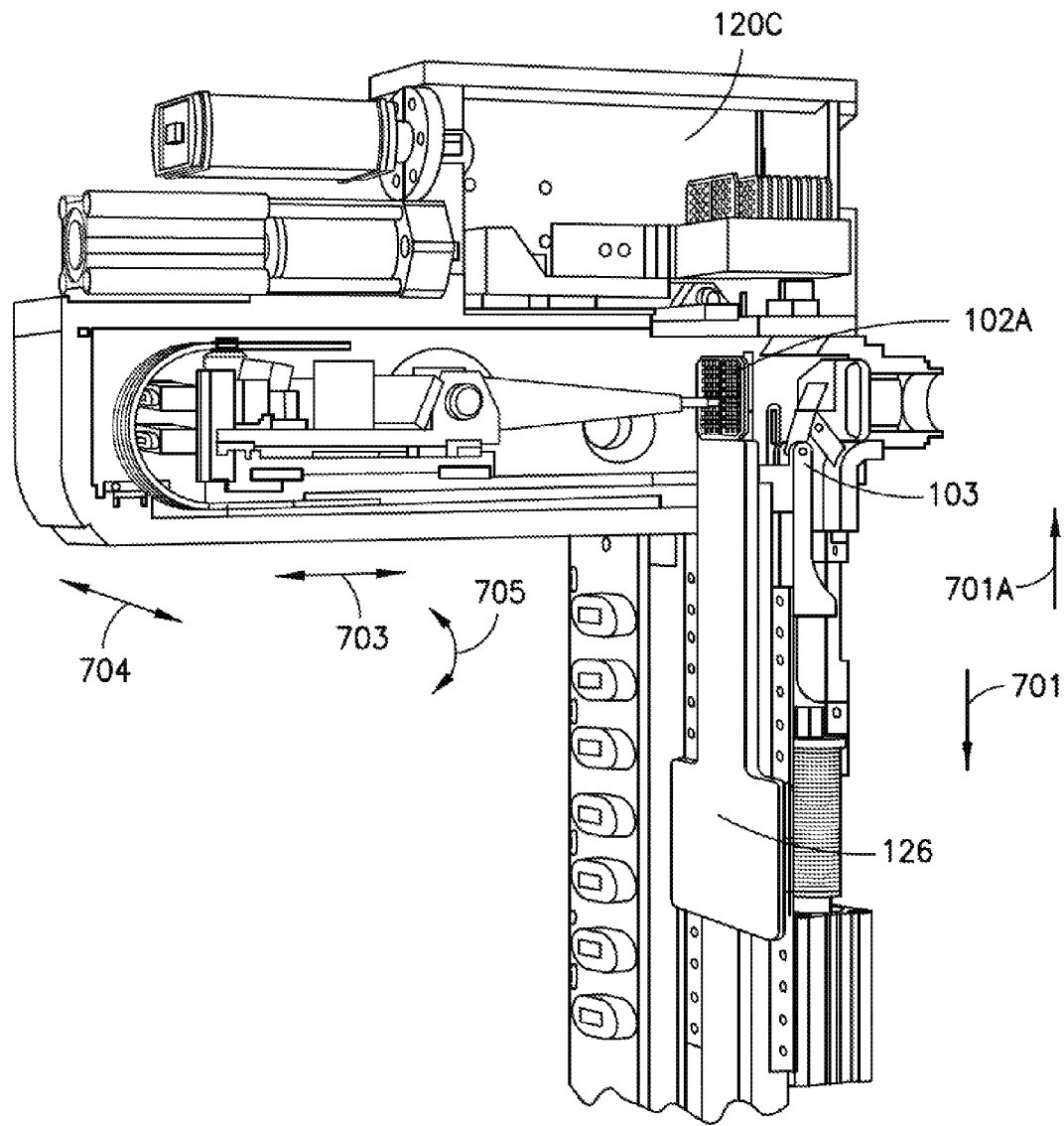
Figure 7C:
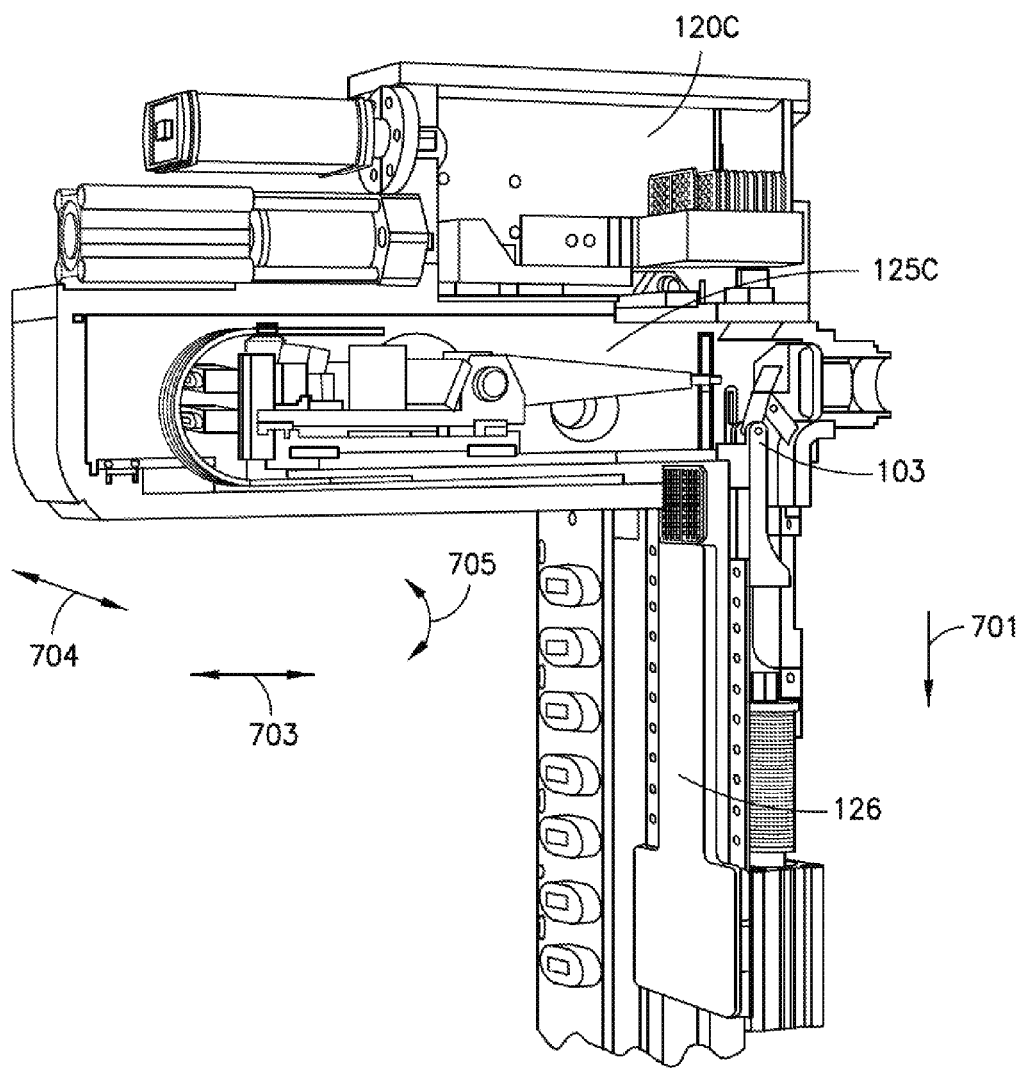
Figure 7D:
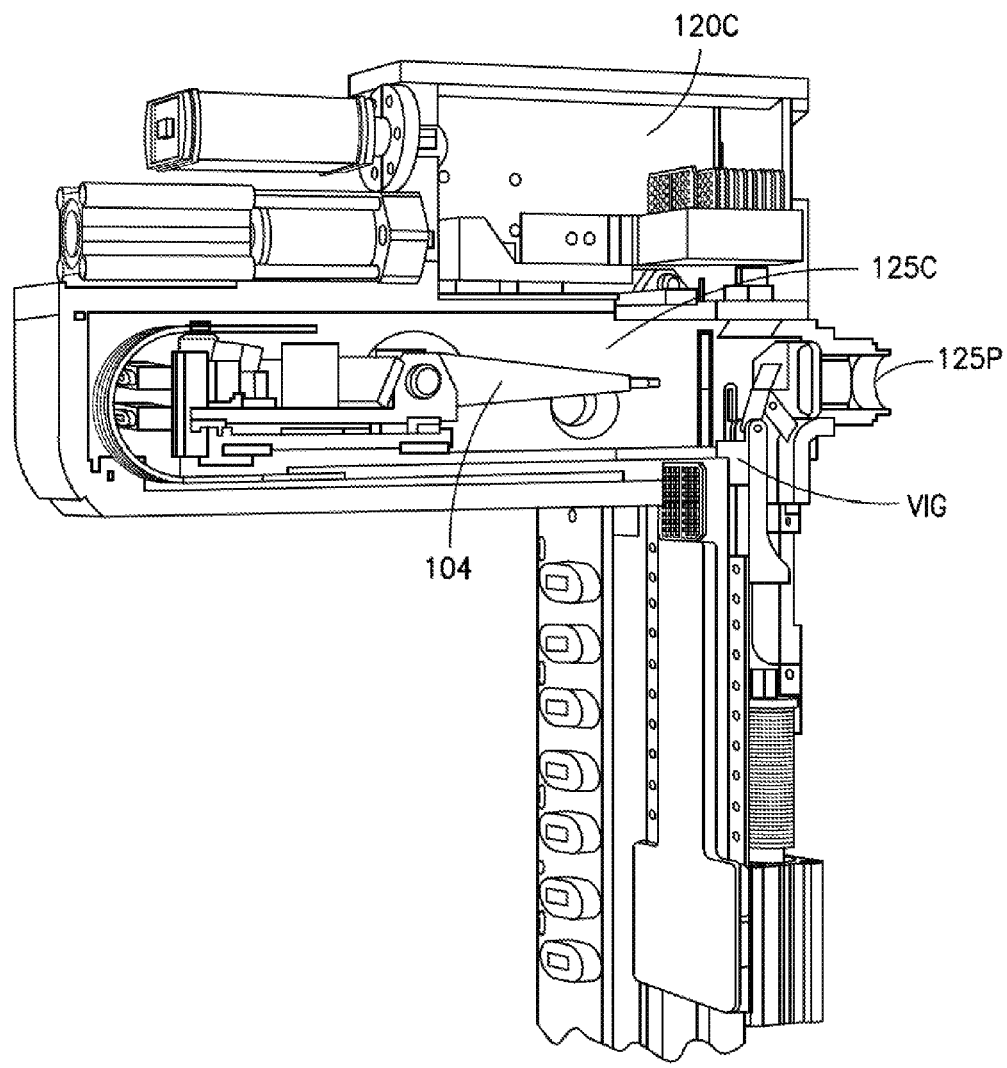
Figure 7E:
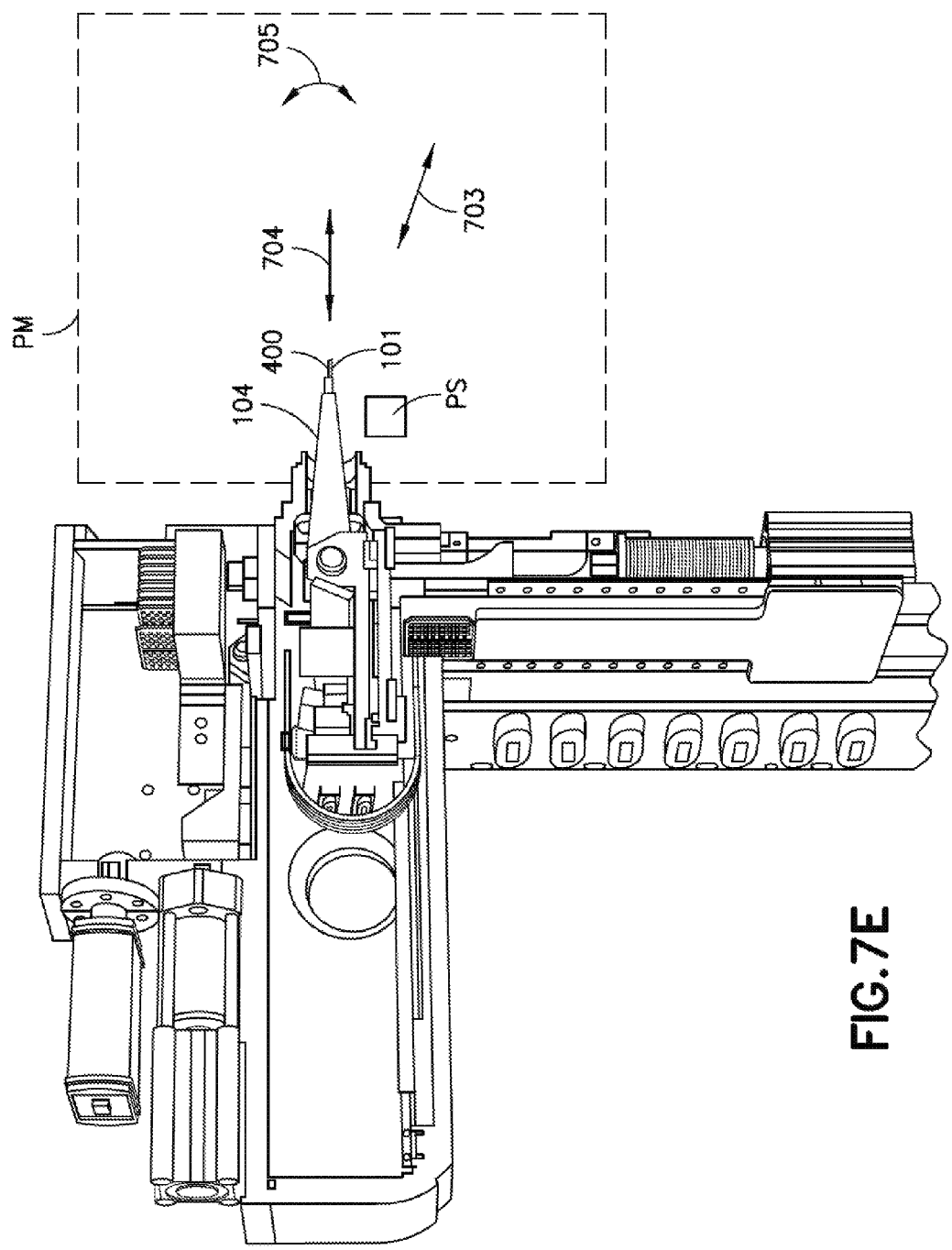
Figure 7F:
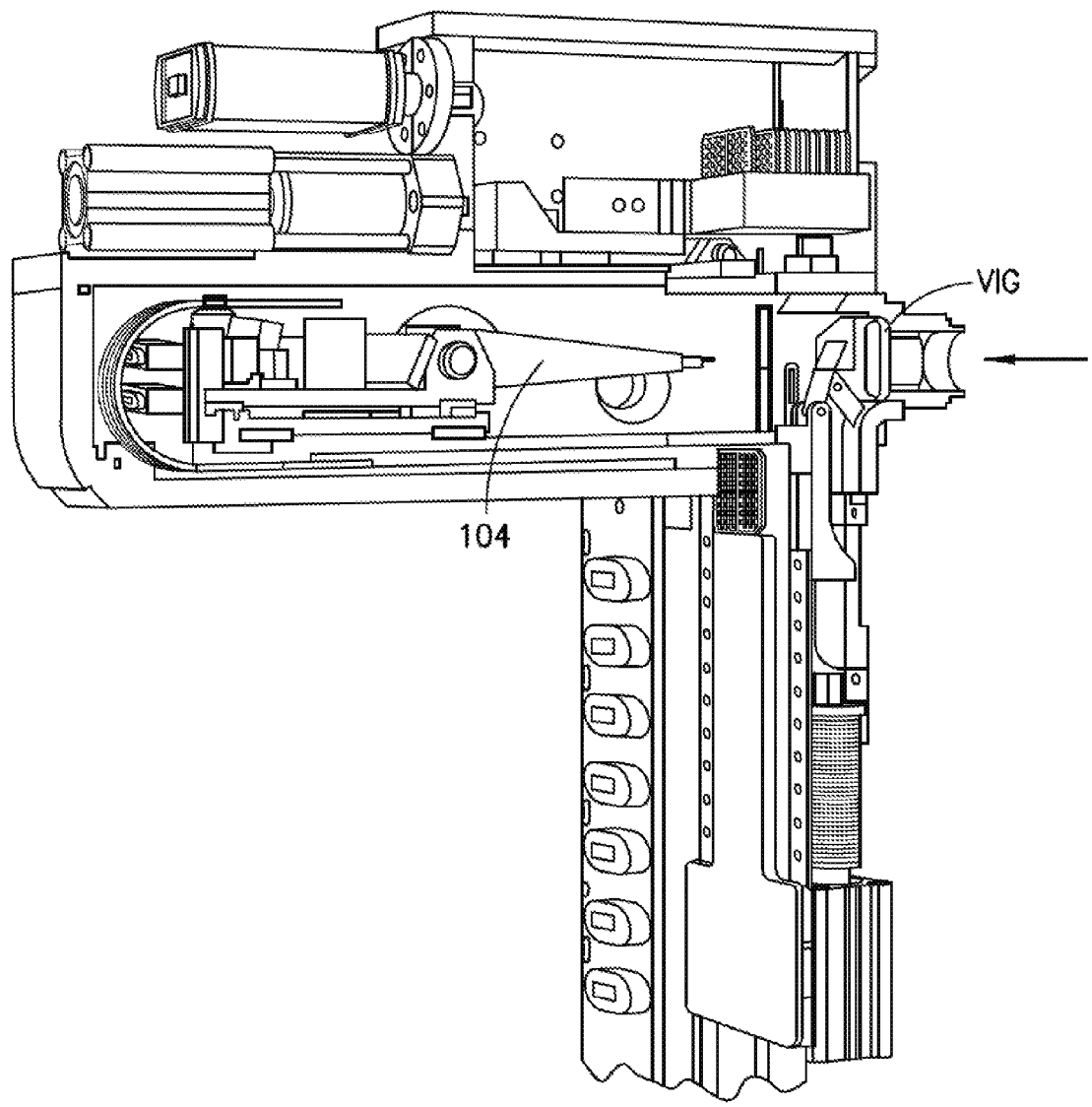

In one aspect, processing data obtained during the processing of the workpiece 400 is communicated by the processing module PM to the controller for inclusion in the data structure DS. The workpiece positioning unit 104 retracts from the process module PM and the valve V1G is closed (FIG. 7F). The cassette shuttle 126 moves in the direction of arrow 701A to position cassette 102 so that the workpiece positioning unit 104 returns the workpiece 400 to the pocket 500 in the cassette 102 from which the workpiece was taken (FIG. 8, Block 865). As may be realized, in one aspect additional workpieces held by the cassette 102 are processed, such as in the predetermined batch workpiece processing sequence, before the cassette 102 is returned to the magazine 105. The valve V2G is opened and the cassette shuttle 126 returns the cassette 102 to the magazine 105, the valve V2G is closed and the transport shuttle 120MS moves to a predetermined position for removal of the magazine from the chamber 120C (FIG. 8, Block 870). In other aspects the transport shuttle 120MS aligns a different cassette 102 with the valve V2G for processing of another workpiece (or multiple workpieces, e.g. a batch of workpieces held by the different cassette) and/or for continuing the processing of a batch of workpieces that is defined in more than one cassette 102.

Figure 9:
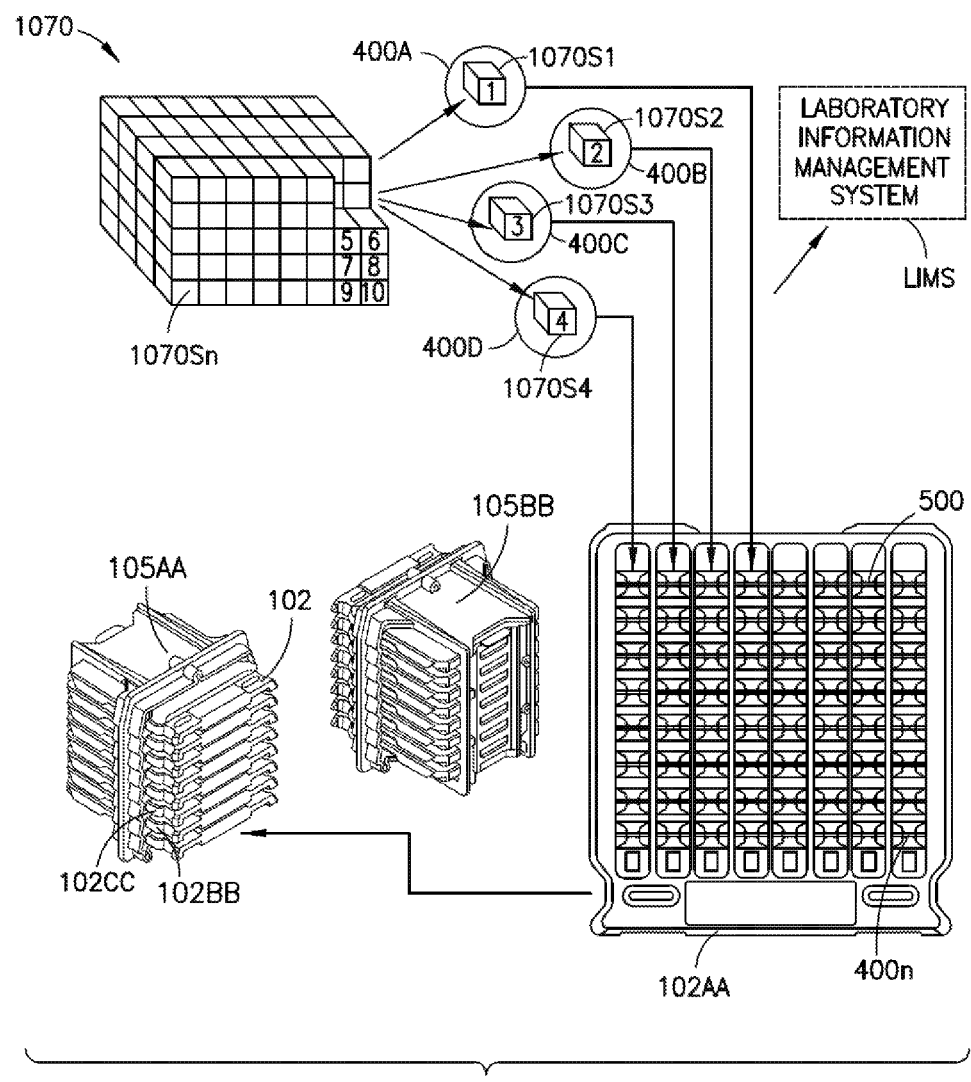
FIG. 9 is a schematic illustration of a portion of a process of the processing system in accordance with aspects of the disclosed embodiment.

Referring to FIG. 9, as noted above, the controller 199 includes a data structure DS that effects tracking and analysis of specimens located on one or more workpieces. In one aspect, workpieces 400A-400n are arranged or otherwise placed within respective pockets 500 of a cassette 102AA in a predetermined ordered sequence, where the ordered sequence corresponds to, for example, one or more of a predetermined arrangement of an array of workpieces 400 in the array of pockets 500, a structure STR of a specimen/structure 1070 the samples 1070S1-1070Sn on the workpieces were taken from or any other suitable criteria. In one aspect, the predetermined ordered sequence of workpieces (and hence a predetermined ordered sequence of specimens located on the workpieces) is defined coincident with loading of each workpiece in an array of workpieces in a cassette 102. As can be seen in FIG. 7B, the structure or specimen 1070 is divided into samples 1070A-1070n where those samples 1070A-1070n are placed on respective workpieces 400A-400n. Those workpieces 400A-400n are placed in one or more cassettes 102AA in a predetermined ordered sequence that embodies, e.g. the structure of the specimen 1070. As may also be realized, in one aspect, the ordered sequence of samples 1070S1-1070Sn or workpieces 400A-400n (e.g. a batch of samples) spans more than one cassette 102AA-102CC such as when one or more cassettes 102 are held within a magazine 105AA and the batch of samples 1070A-1070n or workpieces 400A-400n to be processed includes one or more of the cassettes 102AA-102CC in the magazine 105AA (e.g. the magazine 105AA holds one or more batches where the batches are identified by one or more of a workpiece identifying indicia and a cassette identifying indicia and correspond to, for example, a common structure or specimen). In another aspect the batch of samples including the ordered sequence of samples 1070A-1070n spans multiple magazines 105AA-105BB. In one aspect, the batch(es) (e.g. the workpieces/samples and/or cassettes included in the batches) are defined in a data structure DS (as described in greater detail below) by the workpiece identifying indicia and/or cassette identifying indicia (e.g. the batch to which a workpiece/sample belongs is included in the identifying indicia of a respective workpiece/sample). In one aspect the data structure is resident or embodied in a memory 199M of the controller 199 (for inclusion in, for example, the laboratory information management system LIMS) and is implemented as any suitable database such as, for example, an XML database, a relational database, an object-relational database, or any other database or data structure suitable for storing information as described herein.

In one aspect, the controller 199 includes a neural network and/or a state machine that are configured to create and maintain the data structure DS while in other aspects the controller includes any suitable processing/processor configured to create and maintain the data structure DS. In one aspect the neural network and/or state machine is/are configured to control operations and a process flow of the automated transport and positioning system 100 (e.g. such as routing of automated transports, which workpieces are delivered to which process modules and in which order, etc.) based on information in the data structure DS. The data structure, as described herein, includes data regarding where the workpieces 400 have been throughout, for example, a laboratory or other facility from the time the samples are placed on workpieces to obtaining final results of analysis of the samples as well as detailed data regarding the processes performed on the samples. In one aspect the controller 199 includes a user interface UI configured to allow a user to view the results of the analysis or any other data within the data structure DS including a location of a sample within the laboratory or other facility.

In one aspect the data structure DS includes information pertaining to a batch of workpieces/specimens that are processed through the automated transport and positioning system 100, process module PM or any other suitable laboratory equipment configured to store, transport and/or analyze the workpiece/specimen. As may be realized, any suitable structure or specimen (e.g. source material), such as a biological structure, metallurgical structure, semiconductor structure, etc.) is divided into samples in any suitable manner where each sample is mounted to a respective workpiece 400 in any suitable manner. As each sample is associated with a workpiece 400 (e.g. a sample is mounted to the workpiece), as each workpiece is associated with a cassette 102, as each cassette is associated with a magazine 105 and at each processing step of the workpiece 400 the data structure DS is updated so that the data structure DS associates one or more predetermined characteristic/physical attribute of the sample with the unique identifier of the workpiece 400. As may be realized, the data structure DS also associates samples taken from a common structure with each other so that the individual samples (which are associated with the workpieces) are tracked and analyzed as whole so that an automatic determination of a characteristic of the structure is made with respect to the structure as whole. As may be realized, the vision system (including the sensors described herein) identify the workpieces 400, cassettes 102 and magazines 105 throughout processing so that the processing steps and other information gathered is associated with the corresponding workpiece (and specimen thereon) in the data structure DS (and in the laboratory information management system LIMS) as described in, for example, U.S. patent application Ser. No. 14/538,327 entitled "Workpiece Holder for Workpiece Transport Apparatus" and filed on Nov. 11, 2014, and United States patent application Ser. No. 14/538,332 entitled "Specimen Sample Holder for Workpiece Transport Apparatus" filed on Nov. 11, 2014 the disclosures of which are previously incorporated herein by reference in their entireties.

Figure 10:
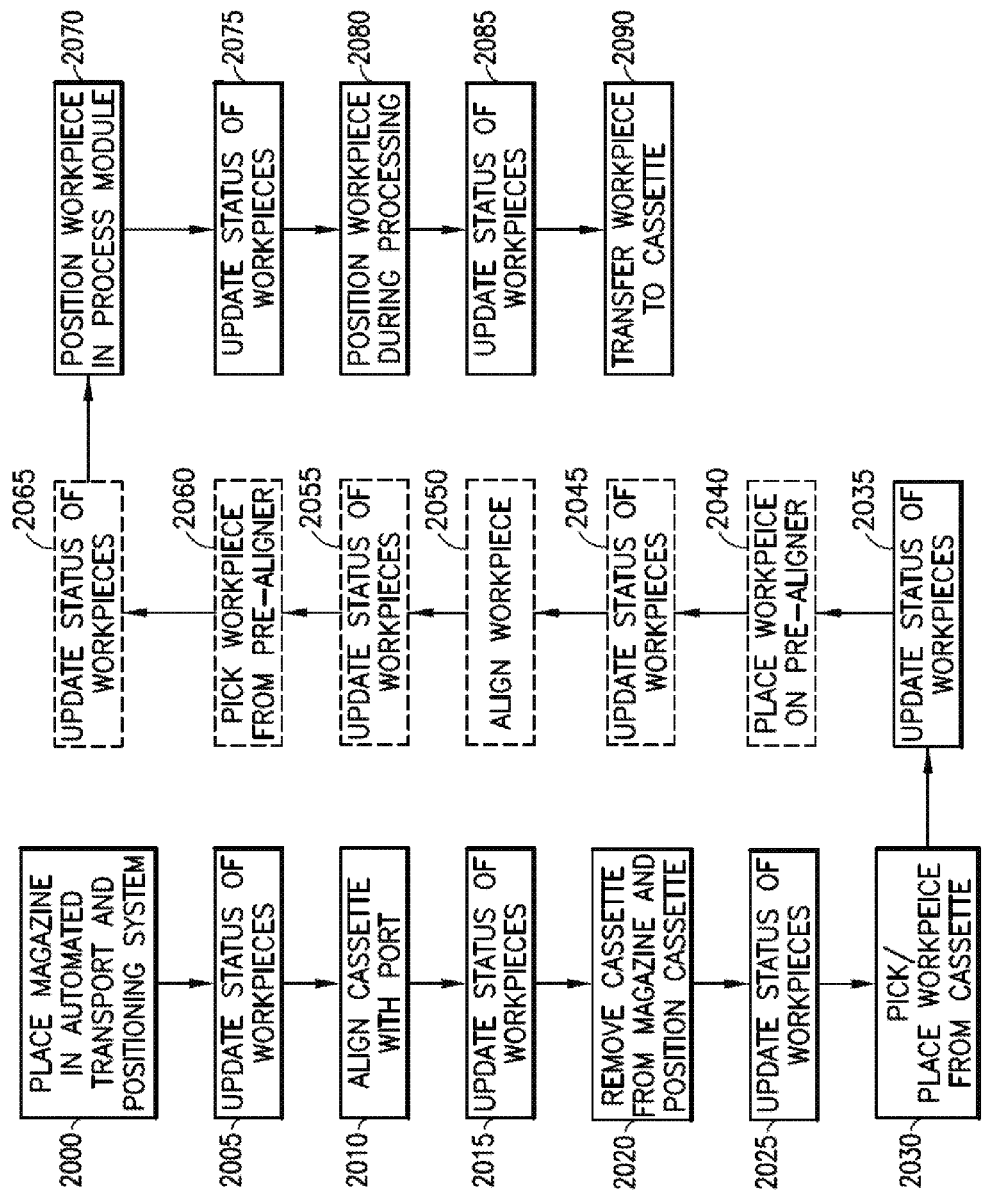
FIG. 10 is a flow diagram of an operation of the automatic specimen loading system of FIG. 1A (1A-1,1A-2)-1D in accordance with aspects of the disclosed embodiment.
Figure 11:
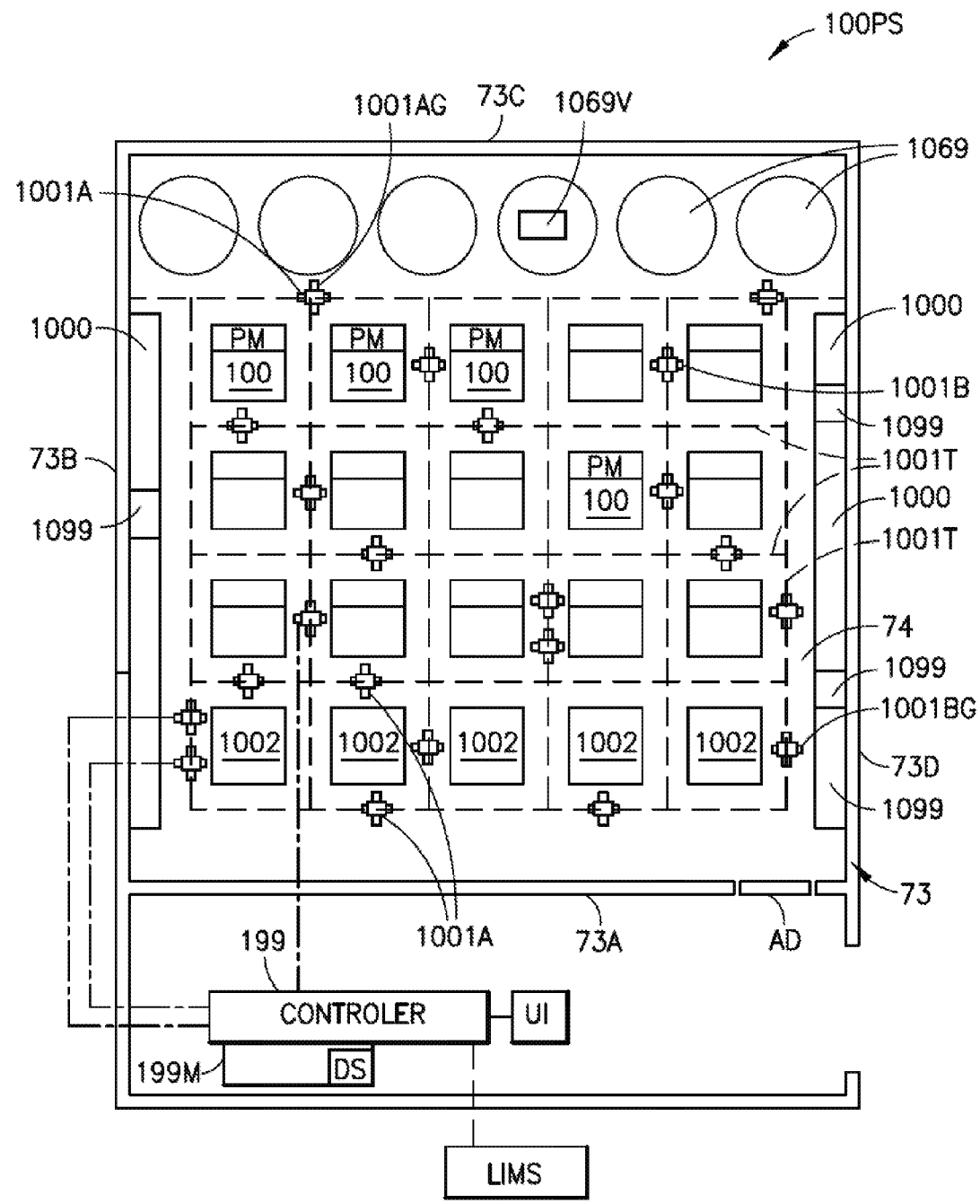
FIG. 11 is a schematic illustration of a processing system in accordance with aspects of the disclosed embodiment.

Referring also to FIG. 1, as may be realized, the movement of the workpieces 400 (and specimen samples thereon) throughout the workpiece processing system or facility 100PS is effected by one or more drive axes of one or more transports, such as the drive axes (e.g. drives or motors) A1L, A2L, A3L, A4L, A5L, A6L, A7R, A8R, A15R of the automated transport and positioning system 100 described above. Each of the drive axes A1L, A2L, A3L, A4L, A5L, A6L, A7R, A8R, A15R provides data to the controller 199 regarding the position of the workpieces 400 (and the specimen samples thereon) to effect updating the status (e.g. location status, processing status, sequence status within a batch of workpieces, orientation status, etc.) of the workpiece in the data structure DS and/or laboratory information management system LIMS (which in one aspect includes the data structure DS). For example, the magazine 105 is placed within the load lock 120 in any suitable manner (such as by an automated transport or manually) and any suitable scanner, such as scanner CAM4 reads the identifying indicia of the magazine 105 (FIG. 10, Block 2000) and sends suitable signals to the controller 199 for updating a status of the workpieces 400 disposed within the magazine 105 as being located within the load lock 120 (FIG. 10, Block 2005). The drive axis A1L moves the magazine 105 to align a cassette 102 within the magazine 105 with, for example, the port 120P (FIG. 10, Block 2010). In one aspect, the drive axis A1L sends suitable encoder or other position data to the controller 199 indicating that a predetermined cassette 102 is aligned with the port 120P where the controller 199 updates a status (e.g. within the data structure DS) of the workpieces 400 in the predetermined cassette 102 as being, for example, positioned for loading into the sealable chamber 125C (FIG. 10, Block 2015). In one aspect, any suitable scanner such as scanner CAM1 reads identifying indicia of the cassette and sends suitable identification data to the controller 199 for updating a status of the workpieces within the cassette. As may be realized, in one aspect, the data sent to the controller 199 by the drive axes A1L, A2L, A3L, A4L, A5L, A6L, A7R, A8R, A15R (and/or the data sent by the sensors CAM1-CAM5) to effect updating the data structure DS is also entered into the laboratory information management system LIMS in any suitable manner (e.g. the controller and data structure are in one aspect incorporated into the laboratory information management system LIMS or connected to the laboratory information management system LIMS in any suitable manner such as through a wired or wireless connection).

The drive axis A2L moves the cassette shuttle 126 to pick/place the predetermined cassette 102 from the magazine 105 through the port 120P (FIG. 10, Block 2020). The drive axis A2L (and a drive axis of a gripper of the cassette shuttle) sends suitable encoder or other position data to the controller 199 (e.g. to update a status of the workpiece(s) in the data structure DS) indicating that the predetermined cassette 102 (and the workpieces located therein) are gripped by the cassette shuttle 126 and are positioned in the Z direction at a predetermined position so that one or more workpieces 400 can be removed from the cassette 102 (FIG. 10, Block 2025). In one aspect one or more sensors, such as sensor CAM2 and/or sensor 281 on the end effector 101 verify the position of and/or effect identification of (e.g. for tracking the processing of one or more workpieces) the cassette 102/workpieces 400 and/or, as will be described below, effect automatic positioning of the end effector and automatic capture of the workpiece by the end effector. One or more of the drive axes A3L, A4L, A5L, A6L, A7R, A15R effect movement of the end effector 101 for picking/placing a workpiece 400 from the cassette 102 (FIG. 10, Block 2030). In a manner similar to that described above, the end effector 101 is positioned to pick/place a predetermined workpiece from a pocket 500 of the cassette 102 such that any suitable encoder or other position data is sent to the controller 199 (e.g. for updating the data structure DS) by one or more of the drive axes A3L, A4L, A5L, A6L, A7R indicating that the predetermined workpiece 400 is picked/placed from/to the cassette and a position of the predetermined workpiece 400 in, for example, one or more of the X, Y and Z directions (FIG. 10, Block 2035). As noted above, in one aspect, the end effector sensor 281 and/or off end effector sensor CAM2 verifies at least the pick/place of the predetermined workpiece 400 relative to the cassette 102. In one aspect the sensor 281 or sensor CAM2 identifies the workpiece being picked for updating process information for the workpiece in the data structure DS. In one aspect, the controller 199 associates electron microscopy data of the workpieces 400 (and the specimens thereon) with identifying indicia of the workpiece 400. In one aspect the identifying indicia of each workpiece 400 is related to a predetermined grid/workpiece batch scanning sequence of specimens effected by the process module PM where the workpieces are arranged in an array of workpieces in a cassette 102. IN one aspect the predetermined grid/workpiece batch scanning sequence is automatically determined with a loading of the cassette 102 (e.g. a sequence of workpiece processing) and/or magazine 105 (e.g. a sequence of cassette processing and a sequence of workpiece processing in each cassette) in the automated transport and positioning system 100. In one aspect the identifying indicia of the workpiece 400 is representative of a source material configuration (see FIG. 9) from which the specimens on a batch of workpieces are made.

In one aspect, the sensor 281 on the end effector 101 and/or the off end effector sensor(s) CAM1-CAM5 provides the controller 199 relative position data between the end effector 101 and a predetermined target (e.g. such as the workpiece 400 to be gripped, a workpiece holding location such as a pocket 500 of the cassette 102 and/or pre-aligner stage 103, a position of the end effector 101/workpiece within the process module PM, etc.) The controller 199 is configured to direct movement of the end effector 101 (e.g. as described herein) based on the relative positioning data such as by making a relative position determination between the end effector 101 and the target so that the end effector is automatically moved/positioned (e.g. changing a relative position between the end effector and target) to effect an automatic capture/release of, for example, the workpiece 400 with the end effector 101 and/or automatic placement of the workpiece 400 at a predetermined position with the end effector 101. As may be realized, the relative position data, in one aspect, effects changing a status (e.g. process and/or positional status) of a workpiece 400 in the data structure DS. For example, the one or more of the sensor(s) 281, CAM1-CAM5 views the pocket 500 of the cassette 102 holding the predetermined workpiece 400 as well as the end effector 101. The controller 199 makes a determination as to the relative position between the workpiece 400 and/or pocket 500 and the end effector and based on the relative position the controller 199 sends suitable control commands to the drive axes A3L, A4L, A5L, A6L, A7R, A15R to effect movement of the end effector for picking/placing the predetermined workpiece from/to the cassette 102. As may be realized, in one aspect the relative position determination between the end effector and the workpiece, workpiece holding location or process location effects movement of the end effector as described herein while in other aspects movement of the end effector is effected in any suitable manner such as through drive axis encoder data.

Once the predetermined workpiece 400 is removed from the cassette 102, as described above, the workpiece is, in one aspect, placed on the pre-aligner stage 130 by the end effector 101 in a manner similar to that described above (FIG. 10, Block 2040). Here the drive axes drive axes A3L, A4L, A5L, A6L, A7R, A15R sends suitable encoder or other position data to the controller 199 indicating that the predetermined workpiece is placed on the pre-aligner stage 103 so that a status of the workpiece is updated in the data structure DS (FIG. 10, Block 2045). The drive axis A8R of the pre-aligner effects alignment of the workpiece 400 (FIG. 10, Block 2050) and sends suitable encoder or other position data to the controller 199 indicating that the predetermined workpiece is oriented in a predetermined process orientation and the status of the workpiece 400 is updated in the data structure DS (FIG. 10, Block 2055). As may be realized, the vision system(s), such as sensors 281 and/or CAM1-CAM5, in one aspect, verify the position of (and/or identify) the workpiece 400 and/or provide position data (in lieu of or in addition to the drive axis data) to the controller for updating the status of the workpiece in the data structure DS. The controller 199 commands the drive axes A3L, A4L, A5L, A6L, A7R, A15R to effect picking the workpiece 400 from the pre-aligner stage (FIG. 10, Block 2060) and the status of the workpiece is updated, based on data provided by the drive axes and/or vision system (FIG. 10, Block 2065).

The controller 199 commands the drive axis A2L of the cassette shuttle 126 to move the cassette 102 in the Z direction so that the workpiece positioning unit 104 has access to the process module PM. The controller 199 commands the opening of port 125P and commands the drive axes A3L, A4L, A5L, A6L, A7R, A15R to effect automatic positioning of the end effector 101 within the process module PM so that the workpiece held on the end effector is positioned in a predetermined process position within the process module PM (FIG. 10, Block 2070). In a manner similar to that described above, the drive axes A3L, A4L, A5L, A6L, A7R, A15R and/or vision system (such as sensors 281 and/or CAM1-CAM5) send suitable encoder or other position data to the controller 199 indicating that the predetermined workpiece 400 is located at a predetermined location in the process module PM so that a status of the workpiece is updated in the data structure DS (FIG. 10, Block 2075).

In one aspect, the movement of the workpiece 400 with the workpiece positioning unit 104 within the process module is effected automatically with relative position data in a manner similar to that described above and/or with data received in the controller 199 from the drive axes A3L, A4L, A5L, A6L, A7R, A15R. As may be realized, the workpiece is moved within the process module during processing in any suitable manner to effect imaging of the specimen sample on the workpiece (FIG. 10, Block 2080) where the status of the workpiece is updated within the data structure DS based on the movement (FIG. 10, Block 2085). In one aspect, the status of the workpiece (e.g. the position and imaging status) is substantially continuously updated during processing. In one aspect, the sensor 281 and/or sensor CAM5 verifies a position of (and/or identifies) the workpiece 400 in the processing chamber for updating a status of the workpiece 400 in the data structure DS. After processing the predetermined workpiece is transferred back to the cassette 102 so that other workpieces in the cassette are processed (FIG. 10, Block 2090). The cassette is returned to the magazine and the magazine is removed from the load port 120. As may be realized at each step in the processing of the workpiece (including removal of the workpiece 400, cassette 102 and magazine 105 from the automated transport and positioning system 100 and subsequent storage or removal of the workpiece from a respective cassette) the status of one or more workpieces in the data structure DS is updated in the manner described herein.

In one aspect the data structure DS provides a series of, for example, data points (formed from the process/analysis data obtained during sample analysis as described above) related to the sequenced order of a batch of samples for a common structure 1070. The controller 199 is, in one aspect, configured to provide an automated determination of a characteristic (e.g. a chemical makeup, a physical makeup, a status or health of biological tissue, a structural integrity of the structure, etc.) of the structure 1070 by analyzing the data points of each sample and providing a conclusion of the overall results for the analysis of the structure 1070 associated with the sequenced order of the batch of samples. As may be realized, the tracking of the samples of the structure 1070, with the data structure DS, from the creation of the samples and placement of the samples on a respective workpiece 400 to the conclusion of overall results for the structure (e.g. comprised of the samples) maintains the integrity of the overall structure 1070 during the automated analysis of each sample of the structure 1070.

Referring to FIGS. 1D, 1E, 1H, 6A-6E and 11 in one aspect, the automated transport and positioning system 100 is part of or integrated in workpiece processing system 100PS. The workpiece processing system is, in one aspect, located within any suitable facility or enclosure 73 that has for example walls 73A, 73B, 73C, 73D connected to each other by a floor 74 and a ceiling/roof (not shown). An access door AD is provided for the enclosure 73 to allow operator access into the enclosure 73 for any suitable reasons. The workpiece processing system or facility 100PS includes, for exemplary purposes only, one or more sample preparation modules 1000, one or more workpiece sequencer modules 1099, one or more automated magazine loaders 1002, one or more automated transport and positioning systems 100 (and the respective processing modules PM), one or more storage modules 1069 and one or more automated transports 1001 all of which are, in one aspect connected to the controller 199 in any suitable manner (e.g. such as through a wired or wireless connection). In one aspect the one or more automated transports 1001 form front loading automation that loads/removes workpieces 400 and/or cassettes 102 to/from one or more workpiece sequencer modules 1099, loads/removes cassettes and/or magazines 105 to one or more automated magazine loaders 1002 and loads/removes magazines 105 to/from one or more automated transport and positioning systems 100 as described in, for example, United States patent application Ser. No. 14/538,327 entitled "Workpiece Holder for Workpiece Transport Apparatus" filed on Nov. 11, 2014, and United States patent application Ser. No. 14/538,332 entitled "Specimen Sample Holder for Workpiece Transport Apparatus" filed on Nov. 11, 2014 the disclosures of which are incorporated herein by reference in their entireties.

The one or more automated transports 1001 include magazine transport units 1001A and cassette transport units 1001B that are configured to travel along a common set of tracks 1001T. In other aspects, there is a set of tracks for the magazine transport units 1001A that are separate and distinct from a set of tracks for the cassette transport units 1001B. In one aspect the magazine transport units 1001A include any suitable gripper 1001AG for gripping the automated handling features AF of the magazines 105 (see e.g. FIGS. 4A-4E) and transporting the magazines 105 (with or without cassettes 102 located therein) between the automated magazine loaders 1002, the automated transport and positioning systems 100 and the storage modules 1069 where kinematic features 610-612 of the magazine locate the magazine 105 in the automated transport and positioning systems 100 and the storage modules 1069. In one aspect, the automated transport shuttle 120MS of the automated transport and positioning system 100 has an overhead transport interface position that, for example, aligns the automated transport shuttle 120MS with the door 120D disposed on a top of the chamber 125C. As noted above, the automated transport shuttle includes kinematic features KFF (FIG. 1D) that interface with kinematic features 610-612 of the magazine 105 for kinematically locating the magazine 105 relative to the automated transport shuttle 120MS. As also described above, the magazine includes automated handling features AF that are in known relationship with the kinematic features 610-612. The automated handling features AF are configured to interface with the gripper 1001AG of, for example, magazine transport units 1001A. The magazine transport units 1001A transport a magazine 105 to a predetermined automated transport and positioning system 100 and align the magazine with the door 120D on the top of the chamber 125C so that when the magazine 105 is lowered through the door 120D, by a magazine transport unit 1001A, the kinematic features 610-612 of the magazine are substantially aligned with the kinematic features KFF of the transport shuttle 120MS.

The cassette transport units 1001B include any suitable gripper 1001BG for gripping the automated handling/kinematic features 510, 511 of the cassettes 102 (see e.g. FIGS. 3A-3F) and transporting the cassettes 102 between the workpiece sequencer modules 1099 and the automated magazine loaders 1002 the where kinematic features 510 of the cassettes 102 are positioned relative to a datum surface, such as a side of the cassette for locating the cassette 102 in the workpiece sequencer modules 1099 and the automated magazine loaders 1002. In one aspect, a common automated transport unit is configured to grip both the automated handling features AF of the magazines 105 and the cassettes automated handling/kinematic features 510, 511 of the cassettes 102 for transporting either one of the magazines 105 and cassettes 102 between any suitable locations of the workpiece processing system 100PS. In one aspect, the one or more automated transports 1001 include any suitable transport for transporting workpieces between the sample preparation modules 1000 and the workpiece sequencer modules 1099. In one aspect the automated transports 1001 are an overhead material handling system (e.g. a gantry system) while in other aspects one or more of the automated transports 1001 are conveyors or any other suitable mechanized transport. As may be realized, the transport of the cassettes 102 and magazines 105 can also be performed manually.

In accordance with one or more aspects of the disclosed embodiment an automated workpiece processing apparatus includes a processing section including a processing module configured for processing a workpiece at a process location; a transport module including a multistage shuttle, the multistage shuttle having a first shuttle stage having multiple degrees of freedom of motion, a second shuttle stage having multiple degrees of freedom of motion independent of the first stage, and an end effector connected to at least one of the first and second shuttle stages, the end effector being configured to hold the workpiece and transport the workpiece into and out of the processing module, the end effector having a range of motion, defined by a combination of the first and second stage multiple degrees of freedom of motions, extending from a workpiece holding station outside the processing module to the processing location inside the processing module for positioning the workpiece at the processing location so that the end effector defines a processing stage of the processing module; and an automated loading and transport section including a load port module through which workpieces are loaded into the automated loading and transport section, the automated loading and transport section being communicably connected to the transport module.

In accordance with one or more aspects of the disclosed embodiment at least one degree of freedom of movement of each of the first and second shuttle stage share a common direction.

In accordance with one or more aspects of the disclosed embodiment the at least one degree of freedom of movement of the first shuttle stage and the at least one degree of freedom of movement of the second shuttle stage are configure for a differential movement along the common direction to effect capture of a workpiece with the end effector.

In accordance with one or more aspects of the disclosed embodiment the automated workpiece processing apparatus further includes a second transport shuttle separate and distinct from the multistage shuttle, the second transport shuttle being configured to transport workpieces between a loading station of the automated loading and transport section and the transport module.

In accordance with one or more aspects of the disclosed embodiment the automated workpiece processing apparatus further includes a third transport shuttle distinct from the multistage shuttle and the second transport shuttle, the third transport shuttle being configured to transport workpieces between the second transport shuttle and the multistage shuttle.

In accordance with one or more aspects of the disclosed embodiment at least one of the first and second shuttle stages includes a tilt axis degree of freedom movement.

In accordance with one or more aspects of the disclosed embodiment the multistage shuttle is configured for operation in a vacuum environment.

In accordance with one or more aspects of the disclosed embodiment the multistage shuttle is configured for operation in an atmospheric environment.

In accordance with one or more aspects of the disclosed embodiment a motion resolution of the multistage shuttle is 0.5 micron.

In accordance with one or more aspects of the disclosed embodiment the end effector includes an integral imaging sensor configured for imaging the workpiece.

In accordance with one or more aspects of the disclosed embodiment an automated workpiece processing apparatus includes a processing section including a processing module configured for processing a workpiece at a process location; and a transport module including a multistage shuttle, the multistage shuttle having a first shuttle stage having multiple degrees of freedom of motion, a second shuttle stage having multiple degrees of freedom of motion independent of the first stage and an end effector connected to at least one of the first and second shuttle stages, the end effector being configured to hold the workpiece and transport the workpiece into and out of the processing module, the end effector having a range of motion, defined by a combination of the first and second stage multiple degrees of freedom of motions, extending from a workpiece holding station outside the processing module to the processing location inside the processing module for positioning the workpiece at the processing location so that the end effector defines a processing stage of the processing module.

In accordance with one or more aspects of the disclosed embodiment the automated workpiece processing apparatus further includes a load lock module communicably connected to the transport module, the load lock module being configured to provide loading and unloading of workpieces to and from the transport module.

In accordance with one or more aspects of the disclosed embodiment the load lock module includes a sealable chamber configured to cycle between an atmosphere of the transport module and an atmosphere external to the transport module.

In accordance with one or more aspects of the disclosed embodiment the atmosphere of the transport module is substantially similar to an atmosphere of the processing module.

In accordance with one or more aspects of the disclosed embodiment the automated workpiece processing apparatus further includes a second transport shuttle separate and distinct from the multistage shuttle, the second transport shuttle being configured to transport workpieces between a loading station of the load lock module and the transport module.

In accordance with one or more aspects of the disclosed embodiment the automated workpiece processing apparatus further includes a third transport shuttle separate and distinct from the multistage shuttle and the second transport shuttle, the third transport shuttle being configured to transport workpieces between the second transport shuttle and the multistage shuttle.

In accordance with one or more aspects of the disclosed embodiment at least one degree of freedom of movement of each of the first and second shuttle stage share a common direction.

In accordance with one or more aspects of the disclosed embodiment the at least one degree of freedom of movement of the first shuttle stage and the at least one degree of freedom of movement of the second shuttle stage are configured for a differential movement along the common direction to effect capture of a workpiece with the end effector.

In accordance with one or more aspects of the disclosed embodiment at least one of the first and second shuttle stages includes a tilt axis degree of freedom movement.

In accordance with one or more aspects of the disclosed embodiment the multistage shuttle is configured for operation in a vacuum environment.

In accordance with one or more aspects of the disclosed embodiment the multistage shuttle is configured for operation in an atmospheric environment.

In accordance with one or more aspects of the disclosed embodiment an automated loading apparatus for an electron microscope includes a frame configured to removably couple to a port of the electron microscope; a transport module connected to the frame, the transport module including a multistage shuttle, the multistage shuttle having a first shuttle stage having multiple degrees of freedom of motion, a second shuttle stage having multiple degrees of freedom of motion independent of the first stage, and an end effector connected to at least one of the first and second shuttle stages, the end effector being configured to hold the workpiece and transport the workpiece into and out of the electron microscope through the port, the end effector having a range of motion, defined by a combination of the first and second stage multiple degrees of freedom of motions, extending from a workpiece holding station outside the electron microscope to a processing location inside the electron microscope for positioning the workpiece at the processing location so that the end effector defines a processing stage of the electron microscope; and an automated loading and transport section connected to the frame and being communicably connected to the transport module, the automated loading and transport section including a load port module through which workpieces are loaded into the automated loading and transport section.

In accordance with one or more aspects of the disclosed embodiment at least one degree of freedom of movement of each of the first and second shuttle stage share a common direction.

In accordance with one or more aspects of the disclosed embodiment the at least one degree of freedom of movement of the first shuttle stage and the at least one degree of freedom of movement of the second shuttle stage are configured for a differential movement along the common direction to effect capture of a workpiece with the end effector.

In accordance with one or more aspects of the disclosed embodiment the automated loading apparatus includes a second transport shuttle separate and distinct from the multistage shuttle, the second transport shuttle being configured to transport workpieces between a loading station of the automated loading and transport section and the transport module.

In accordance with one or more aspects of the disclosed embodiment the second transport shuttle is configured to transport magazines configured to hold one or more cassettes, where the cassettes are configured to hold one or more workpieces.

In accordance with one or more aspects of the disclosed embodiment the automated loading apparatus further includes a third transport shuttle distinct from the multistage shuttle and the second transport shuttle, the third transport shuttle being configured to transport workpieces between the second transport shuttle and the multistage shuttle.

In accordance with one or more aspects of the disclosed embodiment at least one of the first and second shuttle stages includes a tilt axis degree of freedom movement.

In accordance with one or more aspects of the disclosed embodiment the multistage shuttle is configured for operation in a vacuum environment.

In accordance with one or more aspects of the disclosed embodiment the multistage shuttle is configured for operation in an atmospheric environment.

In accordance with one or more aspects of the disclosed embodiment a motion resolution of the multistage shuttle is 0.5 micron.

In accordance with one or more aspects of the disclosed embodiment the end effector includes an integral imaging sensor configured for imaging the workpiece.

In accordance with one or more aspects of the disclosed embodiment the workpiece comprises a specimen grid.

In accordance with one or more aspects of the disclosed embodiment an automated workpiece processing apparatus includes a process module configured for processing a workpiece at a process location within the process module; a transport module having at least one workpiece holding location and being connected to the process module with an opening allowing transport of the workpiece from the transport module to process module through the opening; a workpiece positioning stage with a workpiece gripper disposed to stably hold the workpiece on the stage and configured so that the positioning stage holds the workpiece at the process location in the process module during processing; and a drive section operably connected to the workpiece positioning stage and configured to actuate the workpiece positioning stage so that the positioning stage has at least three degrees of freedom of motion that positions the workpiece at the process location and transports the workpiece to and from the process location and the at least one workpiece holding location in the transport module through the opening; wherein the at least one workpiece holding location is at least a two dimensional array of workpiece holding locations arranged in rows and columns, and wherein the drive section effects the three degrees of freedom of motion at the process location and workpiece transport to each workpiece holding location of the array with an actuator having at least two common drive axes for positioning motion and transport.

In accordance with one or more aspects of the disclosed embodiment each location is arranged so that it holds at least one workpiece.

In accordance with one or more aspects of the disclosed embodiment the drive section actuates the workpiece positioning stage to access each workpiece holding location of the array.

In accordance with one or more aspects of the disclosed embodiment the automated workpiece processing apparatus further includes a loader configured to load and unload workpiece arrays in the at least one workpiece holding location of the transport module.

In accordance with one or more aspects of the disclosed embodiment the drive section is connected to the loader and actuates the loader to load and unload workpiece arrays.

In accordance with one or more aspects of the disclosed embodiment the drive section effects range of motion loading the workpiece to the at least one workpiece holding location, accessing the workpiece at each location of the array at the at least one workpiece holding location, transporting the workpiece to the processing module and providing three degrees of freedom of motion at the process location with no more than six drive axes.

In accordance with one or more aspects of the disclosed embodiment at least one drive axis has gross and fine positioning actuation.

In accordance with one or more aspects of the disclosed embodiment the workpiece gripper is an active gripper actuated by the drive section actuator, and at least one drive axis effecting at least one of the three degrees of freedom of motion at the process location is shared for actuation of the gripper.

In accordance with one or more aspects of the disclosed embodiment a method for processing a workpiece with an automated workpiece processing apparatus includes transporting a workpiece held on an end effector into and out of a processing module where the end effector is connected to a transport module including a multistage shuttle having a first shuttle stage having multiple degrees of freedom of motion and a second shuttle stage having multiple degrees of freedom of motion independent of the first stage and an end effector connected to at least one of the first and second shuttle stages, where the end effector has a range of motion, defined by a combination of the first and second stage multiple degrees of freedom of motions, extending from a workpiece holding station outside the processing module to the processing location inside the processing module for positioning the workpiece at the processing location so that the end effector defines a processing stage of the processing module; and automatically loading the workpiece onto the end effector with an automated loading and transport section including a load port module through which workpieces are loaded into the automated loading and transport section, the automated loading and transport section being communicably connected to the transport module.

In accordance with one or more aspects of the disclosed embodiment at least one degree of freedom of movement of each of the first and second shuttle stage share a common direction.

In accordance with one or more aspects of the disclosed embodiment the method further includes effecting capture of a workpiece with the end effector by a differential movement of the at least one degree of freedom of movement of the first shuttle stage and the at least one degree of freedom of movement of the second shuttle stage along the common direction.

In accordance with one or more aspects of the disclosed embodiment the method further includes transporting workpieces between a loading station of the automated loading and transport section and the transport module with a second transport shuttle separate and distinct from the multistage shuttle.

In accordance with one or more aspects of the disclosed embodiment the method further includes transporting workpieces between the second transport shuttle and the multistage shuttle with a third transport shuttle distinct from the multistage shuttle and the second transport shuttle.

In accordance with one or more aspects of the disclosed embodiment the method further includes providing a tilt axis in at least one of the first and second shuttle stages.

In accordance with one or more aspects of the disclosed embodiment the multistage shuttle is configured for operation in a vacuum environment.

In accordance with one or more aspects of the disclosed embodiment the multistage shuttle is configured for operation in an atmospheric environment.

In accordance with one or more aspects of the disclosed embodiment a motion resolution of the multistage shuttle is 0.5 micron.

In accordance with one or more aspects of the disclosed embodiment the method further includes imaging the workpiece with an imaging sensor integral to the end effector.

In accordance with one or more aspects of the disclosed embodiment a method for an automated workpiece processing apparatus includes stably holding a workpiece on a workpiece positioning stage with a workpiece gripper so that the positioning stage holds the workpiece at a process location in a process module during processing; and actuating the workpiece positioning stage with a drive section operably connected to the workpiece positioning stage so that the positioning stage has at least three degrees of freedom of motion that positions the workpiece at the process location and transports the workpiece to and from the process location and at least one workpiece holding location in a transport module through an opening connecting the process module with the transport module; wherein the at least one workpiece holding location is at least a two dimensional array of workpiece holding locations arranged in rows and columns, and wherein the drive section effects the three degrees of freedom of motion at the process location and workpiece transport to each workpiece holding location of the array with an actuator having at least two common drive axes for positioning motion and transport.

In accordance with one or more aspects of the disclosed embodiment each location is arranged so that it holds at least one workpiece.

In accordance with one or more aspects of the disclosed embodiment the method further includes actuating the workpiece positioning stage with the drive section to access each workpiece holding location of the array.

In accordance with one or more aspects of the disclosed embodiment the method further includes loading and unloading, with a loader, workpiece arrays in the at least one workpiece holding location of the transport module.

In accordance with one or more aspects of the disclosed embodiment the drive section is connected to the loader and the method includes actuating the loader to load and unload workpiece arrays.

In accordance with one or more aspects of the disclosed embodiment the method further includes effecting a range of motion for loading the workpiece to the at least one workpiece holding location with the drive section; accessing the workpiece at each location of the array at the at least one workpiece holding location; and transporting the workpiece to the processing module and providing three degrees of freedom of motion at the process location with no more than six drive axes.

In accordance with one or more aspects of the disclosed embodiment at least one drive axis has gross and fine positioning actuation.

In accordance with one or more aspects of the disclosed embodiment the workpiece gripper is an active gripper actuated by the drive section actuator, the method further comprises actuating the gripper by sharing at least one drive axis effecting at least one of the three degrees of freedom of motion at the process location.

In accordance with one or more aspects of the disclosed embodiment an electron microscope automated specimen holding stage includes a casing having at least a portion of which is sealed and configured to hold a sealed atmosphere therein; a specimen holder connected to the casing and having an effector that engages and holds a specimen and support member that supports the effector from the casing, wherein at least a portion of the specimen holder is disposed within the sealed portion of the casing; a coupling connected to the casing and configured for coupling the casing to an electron microscope scanning chamber so that the sealed portion is in communication with the electron microscope scanning chamber with the effector of the specimen holder located inside the electron microscope scanning chamber; and a drive section connected to and depending from the casing, and having an actuation motor, coupled to the effector, located outside the sealed portion, wherein the actuation motor moves the effector in the electron microscope scanning chamber.

In accordance with one or more aspects of the disclosed embodiment the actuation motor moves the effector in the electron microscope scanning chamber during electron microscope imaging of the specimen held by the effector.

In accordance with one or more aspects of the disclosed embodiment the actuation motor effects at least one degree of freedom of a specimen positioning stage of the electron microscope.

In accordance with one or more aspects of the disclosed embodiment the actuation motor moves the effector along at least one axis so that the specimen holding stage complements specimen positioning of a specimen positioning stage of the electron microscope.

In accordance with one or more aspects of the disclosed embodiment the specimen holder is a fast stage compared to the specimen positioning stage of the electron microscope, the actuation of the fast stage being consistent with and enabling high through-put scanning with the electron microscope.

In accordance with one or more aspects of the disclosed embodiment high through-put scanning has an imaging rate greater than 2 images/second.

In accordance with one or more aspects of the disclosed embodiment the electron microscope automated specimen holding stage further includes a specimen holder fast settling system effecting settling of the effector when actuated with the actuation motor consistent with electron microscope scanning with imaging frame rates in excess of 2 images/second.

In accordance with one or more aspects of the disclosed embodiment the coupling connects the casing to a closable port of the electron microscope scanning chamber and the effector is held by the support member in the electron microscope scanning chamber through the port.

In accordance with one or more aspects of the disclosed embodiment the actuation motor is coupled to the effector by the support member, the actuation motor and effector being located respectively substantially at opposite ends of the support member.

In accordance with one or more aspects of the disclosed embodiment the support member engages the casing at an end of the support member proximate the effector.

In accordance with one or more aspects of the disclosed embodiment the casing has an opening through which the effector and at least a portion of the support member project out of the casing, and wherein the support member and casing engage each other with a bearing proximate the casing opening.

In accordance with one or more aspects of the disclosed embodiment the electron microscope automated specimen holding stage further includes a rolling bearing having an axis of freedom coincident with the drive axis of the actuation motor and engaging the support member and casing proximate the effector end of the support member with the effector.

In accordance with one or more aspects of the disclosed embodiment the supporting member has at least one vibration damping element seated thereon.

In accordance with one or more aspects of the disclosed embodiment the electron microscope automated specimen holding stage further includes a bellows that seals the supporting member to the casing and the bellows isolates the effector end of the support member from the actuation motor.

In accordance with one or more aspects of the disclosed embodiment an electron microscope automated specimen holding stage including an end effector configured to hold a specimen sample holder; an imaging system configured to detect the specimen sample holder and determine a relative position between the specimen sample holder and the end effector; and an end effector drive that effects automatic positioning and automatic specimen sample holder capture with the end effector.

In accordance with one or more aspects of the disclosed embodiment the automatic positioning includes a changing of a relative position between the end effector and the specimen sample holder.

In accordance with one or more aspects of the disclosed embodiment the imaging system is configured to determine a relative position between the specimen sample holder held on the end effector and a specimen sample holder holding or processing station.

In accordance with one or more aspects of the disclosed embodiment the imaging system images a predetermined characteristic of the specimen sample holder where the predetermined characteristic relates the specimen sample holder and a specimen sample held on the specimen sample holder.

In accordance with one or more aspects of the disclosed embodiment the predetermined characteristic is a unique identification indicia of the sample and/or sample holder, with error correction characters.

In accordance with one or more aspects of the disclosed embodiment an electron microscope includes a frame; an electron microscopy column connected to the frame, the frame defining an objective lens chamber of the electron microscopy column; and an automated specimen transport and positioning system connected to the frame, the automated transport and positioning system comprising, a specimen support with an end effector, configured to hold and position the specimen for tomography inspection in the objective lens chamber, and a drive section operably connected to the support and having multiple drive axes disposed to effect multiple independent degree of freedom motion of the end effector, wherein the automated transport and positioning system has a specimen picking position, outside of and sharing a common atmosphere with the objective lens chamber, and the drive section effects movement of the end effector from the picking position to the tomography inspection position with multiple independent degree of freedom tomography inspection positioning of the specimen in one move.

In accordance with one or more aspects of the disclosed embodiment the multiple independent degree of freedom motion includes at least three degrees of freedom.

In accordance with one or more aspects of the disclosed embodiment the multiple independent degree of freedom motion includes at least one linear axis traverse and rotation about at least two axes angled relative to each other.

In accordance with one or more aspects of the disclosed embodiment the drive section is configured to effect an automatic picking of the specimen with the end effector.

In accordance with one or more aspects of the disclosed embodiment the automated transport and positioning system has an integral casing with the objective lens chamber, and the casing forms a transport chamber having a common atmosphere with the objective lens chamber.

In accordance with one or more aspects of the disclosed embodiment the drive section effects motion of the end effector with micron level resolution and repositioning to different tomography inspection positions in less than about 100 milliseconds.

In accordance with one or more aspects of the disclosed embodiment an electron microscope includes an automated specimen holding stage having an end effector configured to hold a specimen grid; an imaging system configured to detect the specimen grid and determine a readable grid data storage medium connected to a frame of the grid embodying a unique predetermined characteristic corresponding to the grid, wherein the grid data storage medium is representative of another predetermined characteristic of the specimen held in the specimen holding receptacle of the grid; and a processor communicably connected to the end effector and imaging system, and configured to register the predetermined characteristic of the grid from data of the grid data storage medium read by the imaging system, and register grid related data defining the other predetermined characteristic of the grid.

In accordance with one or more aspects of the disclosed embodiment the electron microscope further includes an end effector drive that effects, with the controller, automatic positioning and automatic specimen grid capture with the end effector.

In accordance with one or more aspects of the disclosed embodiment the automatic positioning includes a changing of a relative position between the end effector and the specimen sample holder.

In accordance with one or more aspects of the disclosed embodiment the imaging system is configured to determine a relative position between the specimen grid held on the end effector and a specimen grid holding or processing station.

In accordance with one or more aspects of the disclosed embodiment the imaging system images a predetermined characteristic of the specimen sample holder where the other predetermined characteristic of the grid relates the specimen grid and a specimen sample held on the specimen grid.

In accordance with one or more aspects of the disclosed embodiment the predetermined characteristic is a unique identification indicia of the grid, with error correction characters.

In accordance with one or more aspects of the disclosed embodiment the other predetermined characteristic is unique and different than the predetermined characteristic of the specimen grid.

In accordance with one or more aspects of the disclosed embodiment the processor associates electron microscopy data of a specimen on the specimen grid with the predetermined characteristic.

In accordance with one or more aspects of the disclosed embodiment the other predetermined characteristic is related to a predetermined grid batch scanning sequence of specimens effected by the electron microscope.

In accordance with one or more aspects of the disclosed embodiment the predetermined grid batch scanning sequence is automatically determined with loading of a grid batch cassette in an automated transport and positioning unit of the electron microscope.

In accordance with one or more aspects of the disclosed embodiment the other predetermined characteristic is representative of a source material configuration from which grid specimens disposed on a batch of specimen grids are made.

It should be understood that the foregoing description is only illustrative of the aspects of the disclosed embodiment. Various alternatives and modifications can be devised by those skilled in the art without departing from the aspects of the disclosed embodiment. Accordingly, the aspects of the disclosed embodiment are intended to embrace all such alternatives, modifications and variances that fall within the scope of the appended claims. Further, the mere fact that different features are recited in mutually different dependent or independent claims does not indicate that a combination of these features cannot be advantageously used, such a combination remaining within the scope of the aspects of the invention.

What is claimed is:

1. An automated loading apparatus for an electron microscope, the automated loading apparatus comprising:
a frame configured to removably couple to a port of the electron microscope;
an automated transport module connected to the frame, the automated transport module including a multistage shuttle and a drive section configured to effect operation of the multistage shuttle, the multistage shuttle having
a first shuttle stage having multiple degrees of freedom of motion,
a second shuttle stage having multiple degrees of freedom of motion independent of the first stage, and
an end effector dependent from at least one of the first and second shuttle stages, the end effector being configured to hold the workpiece and transport the workpiece into and out of the electron microscope through the port, the end effector having a common support member connected to and dependent from both the first and second shuttle stages with a range of motion of the end effector and the common support, defined by a combination of the first and second stage multiple degrees of freedom of motions in total, extending from a workpiece holding station outside the electron microscope to a processing location inside the electron microscope for positioning the workpiece at the processing location so that the end effector defines a scan workpiece stage of the electron microscope so that the electron microscope scans the workpiece, seated on the end effector, coincident with workpiece scan motion effected by end effector motion of the workpiece from motion of the common support member; and
an automated loading and transport section connected to the frame and being communicably connected to the transport module, the automated loading and transport section including a load port module through which workpieces are loaded into the automated loading and transport section.

2. The automated loading apparatus of claim 1, wherein at least one degree of freedom of movement of each of the first and second shuttle stage share a common direction.

3. The automated loading apparatus of claim 2, wherein the at least one degree of freedom of movement of the first shuttle stage and the at least one degree of freedom of movement of the second shuttle stage are configured for a differential movement along the common direction to effect capture of a workpiece with the end effector.

4. The automated loading apparatus of claim 1, wherein the automated loading apparatus includes a first transport shuttle separate and distinct from the multistage shuttle, the first transport shuttle being configured to transport workpieces between a loading station of the automated loading and transport section and the transport module.

5. The automated loading apparatus of claim 4, wherein the first transport shuttle is configured to transport magazines configured to hold one or more cassettes, where the cassettes are configured to hold one or more workpieces.

6. The automated loading apparatus of claim 4, further comprising a second transport shuttle distinct from the multistage shuttle and the first transport shuttle, the second transport shuttle being configured to transport workpieces between the first transport shuttle and the multistage shuttle.

7. The automated loading apparatus of claim 1, wherein at least one of the first and second shuttle stages includes a tilt axis degree of freedom movement.

8. An electron microscope automated specimen scan holding stage comprising:
a casing having at least a portion of which is sealed and configured to hold a sealed atmosphere therein;
a specimen holder connected to the casing and having an effector that engages and holds a specimen and support member that supports the effector from the casing, wherein at least a portion of the specimen holder is disposed within the sealed portion of the casing;
a coupling connected to the casing and configured for coupling the casing to an electron microscope scanning chamber of an electron microscope so that the sealed portion is in communication with the electron microscope scanning chamber with the effector of the specimen holder located inside the electron microscope scanning chamber; and
a drive section connected to and depending from the casing, and having an actuation motor, coupled to the effector, located outside the sealed portion, wherein the actuation motor moves the effector in the electron microscope scanning chamber effecting specimen scan movement of the electron microscope automated specimen scan holding stage, wherein the electron microscope scans the specimen, seated on the electron microscope automated specimen scan holding stage, coincident with specimen scan movement effected by specimen holder effector movement of the specimen from the actuation motor.

9. The electron microscope automated specimen holding stage of claim 8, wherein the actuation motor moves the effector in the electron microscope scanning chamber during electron microscope imaging of the specimen held by the effector.

10. The electron microscope automated specimen holding stage of claim 8, wherein the actuation motor effects at least one degree of freedom of a specimen positioning stage of the electron microscope.

11. The electron microscope automated specimen holding stage of claim 10, wherein the specimen holder is a fast stage compared to the specimen positioning stage of the electron microscope, the actuation of the fast stage being consistent with and enabling high through-put scanning with the electron microscope, wherein enabling of the high through-put scanning with the electron microscope is based on fast stage actuation motions and setting.

12. The electron microscope automated specimen holding stage of claim 11, wherein high through-put scanning has an imaging rate greater than 2 images/second.

13. The electron microscope automated specimen holding stage of claim 8, further comprising a specimen holder fast settling system effecting settling of the effector when actuated with the actuation motor consistent with electron microscope scanning with imaging frame rates in excess of 2 images/second.

14. The electron microscope automated specimen holding stage of claim 8, wherein the supporting member has at least one vibration damping element seated thereon.

15. The automated loading apparatus of claim 5, further comprising at least one camera located in line of sight of the automated loading and transport section, the at least one camera being configured to record cassette and magazine identifying indicia embodied on the cassettes and magazines.

16. The automated loading apparatus of claim 15, wherein the at least one camera being configured to record location information of the workpieces in the cassettes, the location information configured for tracking of the workpieces.

17. The automated loading apparatus of claim 1, wherein the electron microscope further comprises an electron microscope processing stage inside the electron microscope, the electron microscope processing stage being configured for positioning the workpiece at the processing location.

18. The automated loading apparatus of claim 17, wherein the end effector being configured for transferring the workpiece to the electron microscope processing stage for positioning of the workpiece at the processing location.

19. The automated loading apparatus of claim 1, wherein the workpieces loaded through the load port module into the automated loading and transport section are positioned in a cassette, the cassette being configured for holding one or more workpiece batches of one or more workpieces.

20. The automated loading apparatus of claim 19, wherein another cassette holding other of the one or more workpiece batches of the one or more workpieces is loaded into the load port while the end effector is in a processing module atmosphere.

* * * * *